United States Patent
Beckley

(10) Patent No.: US 11,573,225 B2
(45) Date of Patent: Feb. 7, 2023

(54) SYSTEM FOR EVALUATING URINE FOR THE PRESENCE OR ABSENCE OF PREGNANEDIOL GLUCURONIDE AND OTHER HORMONES AND ANALYTES

(71) Applicant: MFB Fertility, Inc., Erie, CO (US)

(72) Inventor: Amy Beckley, Erie, CO (US)

(73) Assignee: MFB Fertility, Inc., Erie, CO (US)

( * ) Notice: Subject to any disclaimer, the term of this patent is extended or adjusted under 35 U.S.C. 154(b) by 0 days.

(21) Appl. No.: 17/317,212

(22) Filed: May 11, 2021

(65) Prior Publication Data

US 2021/0293809 A1    Sep. 23, 2021

Related U.S. Application Data

(63) Continuation of application No. 16/732,823, filed on Jan. 2, 2020, now Pat. No. 11,061,026, which is a
(Continued)

(51) Int. Cl.
*G01N 33/558* (2006.01)
*G01N 33/74* (2006.01)
(Continued)

(52) U.S. Cl.
CPC ......... *G01N 33/558* (2013.01); *G01N 21/255* (2013.01); *G01N 21/293* (2013.01);
(Continued)

(58) Field of Classification Search
CPC ........... G01N 33/558; G01N 33/54387; G01N 33/54388; G01N 33/54389; G01N 33/689;
(Continued)

(56) References Cited

U.S. PATENT DOCUMENTS 3,335,638 A    8/1967  John
4,094,647 A    6/1978  Deutsch et al.
(Continued)

FOREIGN PATENT DOCUMENTS

CA    3043270 A1    6/2018
CN    104697938 B   4/2018
(Continued)

OTHER PUBLICATIONS

Bouchard et al., (2019). "Pilot Evaluation of a New Urine Progesterone Test to Confirm Ovulation in Women Using a Fertility Monitor," Front. Public Health, 7:184, 4 pages.
(Continued)

*Primary Examiner* — Christopher L Chin
(74) *Attorney, Agent, or Firm* — Morrison & Foerster LLP

(57) ABSTRACT

Various aspects of the system and methods described herein rely upon the operation of lateral flow assays specially configured to evaluate a bodily fluid for at least the presence or absence of pregnanediol glucuronide at a threshold selected from the range inclusive of 1 μg/mL-10 μg/mL. The results from the lateral flow assays are optionally interpreted in association with an application operating upon a mobile device or a system for the collection, interpretation and storage of results. The interpretations are useful in accordance with facilitating diagnoses and treatments associated with medical conditions related to the generated interpretations of the lateral flow assays.

17 Claims, 47 Drawing Sheets

Related U.S. Application Data continuation of application No. 16/544,554, filed on Aug. 19, 2019, and a continuation of application No. 16/381,229, filed as application No. PCT/US2018/068027 on Dec. 28, 2018, and a continuation of application No. 15/900,794, filed on Feb. 20, 2018, now abandoned, said application No. 16/544,554 is a continuation-in-part of application No. 15/974,229, filed on May 8, 2018, said application No. 17/317,212 is a continuation of application No. PCT/US2020/040600, filed on Jul. 2, 2020, and a continuation-in-part of application No. 17/308,149, filed on May 5, 2021, now Pat. No. 11,131,665, which is a continuation of application No. 16/732,766, filed on Jan. 2, 2020, now Pat. No. 11,029,321, said application No. PCT/US2018/068027 is a continuation of application No. 15/900,794, filed on Feb. 20, 2018, now abandoned.

(60) Provisional application No. 63/112,051, filed on Nov. 10, 2020, provisional application No. 63/023,116, filed on May 11, 2020, provisional application No. 62/720,953, filed on Aug. 22, 2018, provisional application No. 62/611,467, filed on Dec. 28, 2017, provisional application No. 62/503,223, filed on May 8, 2017, provisional application No. 62/460,307, filed on Feb. 17, 2017.

(51) Int. Cl.
*G01N 21/64* (2006.01)
*G01N 33/68* (2006.01)
*G01N 33/76* (2006.01)
*G06T 7/11* (2017.01)
*G06T 7/90* (2017.01)
*G01N 21/25* (2006.01)
*G01N 21/29* (2006.01)
*G01N 33/53* (2006.01)
*G01N 21/17* (2006.01)

(52) U.S. Cl.
CPC ....... *G01N 21/6428* (2013.01); *G01N 33/689* (2013.01); *G01N 33/74* (2013.01); *G01N 33/743* (2013.01); *G01N 33/76* (2013.01); *G06T 7/11* (2017.01); *G06T 7/90* (2017.01); *G01N 33/5308* (2013.01); *G01N 2021/1765* (2013.01); *G06T 2207/20132* (2013.01)

(58) Field of Classification Search
CPC .. G01N 33/743; G01N 33/76; G01N 2333/59; B01L 2300/0825; G06T 7/0012
USPC ....... 422/400, 401, 420, 421, 425, 426, 430; 435/287.7, 287.9, 805, 810, 970, 973; 436/169, 170, 514, 518, 530, 810
See application file for complete search history.

(56) References Cited

U.S. PATENT DOCUMENTS

| | | |
|---|---|---|
| 4,168,146 A | 9/1979 | Grubb et al. |
| 4,235,601 A | 11/1980 | Deutsch et al. |
| 4,361,537 A | 11/1982 | Deutsch et al. |
| 4,376,110 A | 3/1983 | David et al. |
| 4,450,239 A | 5/1984 | Chatterton |
| 4,703,017 A | 10/1987 | Campbell et al. |
| 4,775,636 A | 10/1988 | Moeremans et al. |
| 4,855,240 A | 8/1989 | Rosenstein et al. |
| 4,857,453 A | 8/1989 | Ullman et al. |
| 4,861,711 A | 8/1989 | Friesen et al. |
| 4,943,522 A | 7/1990 | Eisinger et al. |
| 4,952,517 A | 8/1990 | Bahar |
| 5,158,869 A | 10/1992 | Pouletty et al. |
| 5,252,496 A | 10/1993 | Kang et al. |
| 5,424,193 A | 6/1995 | Pronovost et al. |
| 6,156,271 A | 12/2000 | May |
| 6,319,676 B1 | 11/2001 | Nazareth et al. |
| 6,352,862 B1 | 3/2002 | Davis et al. |
| 6,451,619 B1 | 9/2002 | Catt et al. |
| 6,699,722 B2 | 3/2004 | Bauer et al. |
| 6,924,153 B1 | 8/2005 | Boehringer et al. |
| 7,144,742 B2 | 12/2006 | Boehringer et al. |
| 7,943,395 B2 | 5/2011 | Wei et al. |
| 9,063,091 B2 | 6/2015 | Tsai et al. |
| 9,206,254 B2 | 12/2015 | Decourtye et al. |
| 9,386,221 B2 | 7/2016 | Kauniskangas et al. |
| 9,787,815 B2 | 10/2017 | Erickson et al. |
| 9,939,385 B2 | 4/2018 | Nazareth et al. |
| 11,029,321 B2 | 6/2021 | Beckley |
| 11,061,026 B2 | 7/2021 | Beckley |
| 11,131,665 B1 | 9/2021 | Beckley |
| 2004/0253142 A1 | 12/2004 | Brewster et al. |
| 2005/0130311 A1* | 6/2005 | Coley et al. ........... G01N 33/74 436/65 |
| 2006/0008896 A1 | 1/2006 | Nazareth et al. |
| 2006/0121626 A1 | 6/2006 | Imrich |
| 2009/0137478 A1 | 5/2009 | Bernstein et al. |
| 2009/0228303 A1 | 9/2009 | Faulkner et al. |
| 2010/0312137 A1 | 12/2010 | Gilmour et al. |
| 2012/0321519 A1 | 12/2012 | Brown |
| 2013/0065321 A1 | 3/2013 | Nazareth et al. |
| 2013/0273563 A1 | 10/2013 | Ehrenkranz |
| 2015/0094227 A1 | 4/2015 | McCarthy et al. |
| 2015/0304555 A1 | 10/2015 | Ehrenkranz |
| 2015/0338387 A1 | 11/2015 | Ehrenkranz |
| 2016/0139156 A1 | 5/2016 | Lakdawala |
| 2016/0167042 A1 | 6/2016 | Tyrrell et al. |
| 2016/0178607 A1 | 6/2016 | Husheer et al. |
| 2016/0188937 A1 | 6/2016 | Tyrrell et al. |
| 2016/0210427 A1 | 7/2016 | Mynhier et al. |
| 2017/0007215 A1 | 1/2017 | Salvme |
| 2017/0011194 A1 | 1/2017 | Arshad et al. |
| 2017/0327023 A1 | 11/2017 | Leurck et al. |
| 2018/0088136 A1 | 3/2018 | Saji et al. |
| 2018/0106799 A1 | 4/2018 | Brenner et al. |
| 2018/0129722 A1 | 5/2018 | Bormann et al. |
| 2018/0196037 A1 | 7/2018 | Polwart et al. |
| 2018/0321251 A1 | 11/2018 | Beckley |
| 2018/0366232 A1 | 12/2018 | Dvorak et al. |
| 2019/0027251 A1 | 1/2019 | Pulitzer et al. |
| 2019/0212353 A1 | 7/2019 | Yang et al. |
| 2020/0078781 A1 | 3/2020 | Beckley |
| 2020/0141953 A1 | 5/2020 | Beckley |
| 2020/0141954 A1 | 5/2020 | Beckley |
| 2020/0152038 A1 | 5/2020 | Herbst et al. |
| 2021/0055310 A1 | 2/2021 | Beckley |
| 2021/0293800 A1 | 9/2021 | Beckley |
| 2021/0389311 A1 | 12/2021 | Beckley |
| 2022/0146408 A1 | 5/2022 | Koudele et al. |

FOREIGN PATENT DOCUMENTS

| | | |
|---|---|---|
| EP | 158746 A2 | 10/1985 |
| EP | 276152 A1 | 7/1988 |
| EP | 306772 A1 | 3/1989 |
| EP | 451800 A1 | 10/1991 |
| EP | 0656118 B1 | 6/1995 |
| EP | 1066530 A1 | 1/2001 |
| EP | 2788764 A1 | 10/2014 |
| EP | 2839264 A1 | 2/2015 |
| EP | 2861991 A1 | 4/2015 |
| EP | 2861991 B1 | 4/2015 |
| EP | 3052944 A1 | 8/2016 |
| GB | 2204398 B | 8/1991 |
| WO | WO-1994004924 A1 | 3/1994 |
| WO | 1995016920 A1 | 6/1995 |
| WO | 9839657 A1 | 9/1998 |
| WO | WO-2006010072 A2 | 1/2006 |
| WO | 2007/049157 A2 | 5/2007 |
| WO | WO-2013188860 A1 | 12/2013 |

(56) References Cited

FOREIGN PATENT DOCUMENTS

| WO | WO-2015049510 A1 | 4/2015 |
|---|---|---|
| WO | 2016/115608 A1 | 7/2016 |
| WO | WO-2016142610 A1 | 9/2016 |
| WO | 2016/166415 A1 | 10/2016 |
| WO | 2017/058827 A1 | 4/2017 |
| WO | 2017/180909 A1 | 10/2017 |
| WO | WO-2017198204 A1 | 11/2017 |
| WO | WO-2018236792 A1 | 12/2018 |
| WO | WO-2019023926 A1 | 2/2019 |
| WO | WO-2019133920 A1 | 7/2019 |
| WO | WO-2019246361 A1 | 12/2019 |
| WO | WO-2021034412 A1 | 2/2021 |

OTHER PUBLICATIONS

Indiegogo, (2017). "At Home Ovulation Double Check Test," available online at <https://www.indiegogo.com/projects/at-home-ovulation-double-check-test#/>, 14 pages.

International Search Rport and Written Opinion for International Patent Application No. PCT/US2021/72306 dated Feb. 3, 2022, 10 pages.

Ecohard et al., (2013). "Use of urinary pregnanediol 3-glucuronide to confirm ovulation," Steroids, 78:1035-1040.

Hermanson, (1996). "Chapter 20: Antibody Modification and Conjugation," Bioconjugate Techniques, p. 878.

Koczula et al., (2016). "Lateral flow assays," Essays in Biochemistry, 60:111-120.

Maggio, "Enzyme Immunoassay", CRC Press 1980, 54-70.

Merriam-Webster, (2020). "Definition: base unit," Available online at <https://www.merriam-webster.com/dictionary/base unit>, 10 pages.

Pauillac et al., (1998). "An improved method for the production of antibodies to lipophilic carboxylic hapten using small amount of hapten-carrier conjugate," Journal of Immunological Methods, 220:105-114.

Santoro et al., (2012). "Reproductive Hormones and the Menopause Transition," Obstet Gynecol Clin North Am., Author manuscript available online at <https://www.ncbi.nlm.nih.gov/pmc/articles/PMC3197715/>, 15 pages.

Su et al., (2013). "Hormone changes associated with the menopausal transition," Minerva Ginecol., Author manuscript available online at <https://www.ncbi.nlm.nih.gov/pmc/articles/PMC3823936/>, 9 pages.

Vyjayanthi et al., (1995). "Binding characteristics of bovine serum albumin-afloxin B1 to polystyrene microtiter plates: Importance of hapten to carrier protein molar ratio," Indian Journal of Experimental Biology, 33:329-332.

Youtube, (2018). "Testing progesterone at home: MFB Proov test," Available online at <https://m.youtube.com/watch?v=zjMR9FDQip0>.

Extended European Search Report and Written Opinion received for European Patent Application No. 18895132.1 dated Sep. 9, 2021, 12 pages.

Su et al., (2017). "Detection of ovulation, a review of currently available methods," Bioeng Transl Med., 16:238-246.

MFB Fertility, Inc. (2017). "Ovulation Double Check, Catalog # MFB-01," retrieved online from <https://nebula.wsimg.com/9d9ad3495de83e7be3d53247867b8966?AccessKeyId=DA50EDF93F4AF80A8854&disposition=0&alloworigin=1>, 2 pages.

Unpublished U.S. Appl. No. 17/636,755, filed Jul. 2, 2020 titled "Systems and Methods for Menstrual Cycle Testing," (Copy not submitted herewith pursuant to the waiver of 37 C.F.R. § 1.98(a)(2)(iii)).

Mesen, T.B., et al., "Progesterone and the Luteal Phase: A Requisite to Reproduction," Obstetrics and Gynecology Clinics of North America, Mar. 2015, vol. 42, No. 1, pp. 135-151; p. 3, 4th paragraph; p. 4, 3rd paragraph; p. 6, 5th paragraph; p. 7, 2nd paragraph; p. 9, 2nd paragraph; DOI: 10.1016/j.ogc.2014.10.003.

MFB Fertility Inc., "How do Ovulation Double Check Tests Work," Oct. 2, 2017 [retrieved on Feb. 25, 2019]. Retrieved from the internet; timestamps 0:07-0:45, 1:00-2:30.

Munro, C.J., et al., "Relationship of Serum Estradiol and Progesterone Concentrations to the Excretion Profiles of Their Major Urinary Metabolites as Measured by Enzyme Immunoassay and Radioimmunoassay," Clinical Chemistry, Jun. 1991, vol. 37, No. 6, pp. 838-844; p. 840, 2nd column, 3rd paragraph; Table 2.

PCT International Search Report with attached Written Opinion of the International Searching Authority for International Application No. PCT/US18/68027, dated Mar. 26, 2019, 16 pages.

R. Leiva, M. McNamara-Killan, H. Niezgoda, et al., Pilot observational prospective cohort study on the use of a novel home-based urinary pregnanediol 3-glucuronide (PDG) test to confirm ovulation when used as adjunct to fertility awareness methods (FAMs) stage 1. BMJ Open 2019.

S. Kerrigan and W. Phillips, Comparison of ELISAs for Opiates, Methamphetamine, Cocaine Metabolite, Benzodiazepines, Phencyclidine, and Cannabinoids in Whole Blood and Urine. Clinical Chemistry 47:3 540-547 (2001).

GooglePlay, "DaysyView" Valley Electronics, Aug. 20, 2015, p. 1, Paragraphs 1 and 3 (5 pages).

PCT International Search Report with attached Written Opinion of the International Searching Authority for International Application No. PCT/US20/40600, dated Nov. 20, 2020, 13 pages.

\* cited by examiner

Color Intensity Key

| | Color Intensity (RGB) | Analyte Concentration µg/mL |
|---|---|---|
|  | 170 | 5.9 |
|  | 160 | 5.2 |
|  | 150 | 4.8 |
|  | 140 | 3.9 |
|  | 130 | 3.7 |
|  | 120 | 3.5 |
|  | 110 | 3 |
|  | 100 | 0 |

Triggering a purchase and delivery of additional lateral flow assay tests following the usage of a quantity of lateral flow assay tests correlative to one menstrual cycle — 2024

Fig. 19
(cont'd)

Following the earlier of the occurrence of a lateral flow assay indicating a positive result for the presence of LH at a threshold within a series of previously taken diagnostic tests within the same menstrual cycle or the passage from the onset of menstruation in the same menstrual cycle of a number of days corresponding to the length of the subject woman's average menstrual cycle less 10 days, commencing testing for PdG by utilization of a diagnostic test configured to detect at least the presence or absence of PdG at a threshold once daily on a daily basis —3007

Fig. 21
(cont'd)

Suggesting a telemedicine consultation with a healthcare professional following the identification of one or more trends associated with the undesirable absence of at least one hormone or hormonal analyte as indicated on one or more appropriately configured diagnostic test(s) during a specified timeframe —— 4015

Fig. 22
(cont'd)

Depicting the result onto a display featuring a calendar with the result displayed on in association with the date the diagnostic test was performed — 4025

Fig. 23
(cont'd)

| Healthcare Providor: | Dr. Jane Johnson | | |
|---|---|---|---|
| Jurisidction of License: | Colorado, California | edit | |
| Areas of Specialization: | OBGYN, Fertility Counseling | edit | |

7061
7060

Choose Available Times for Telemedic Consultations:

Monday, June 17
Tuesday, June 18
Wednesday, June 19
Thursday, June 20

| 9:00 AM ☐ | 9:30 AM ☐ | 10:00 AM ☑ | 10:30 AM ☑ |
| 9:00 AM ☐ | 9:30 AM ☐ | 10:00 AM ☐ | 10:30 AM ☐ |
| 9:00 AM ☑ | 9:30 AM ☐ | 10:00 AM ☑ | 10:30 AM ☐ |
| 9:00 AM ☐ | 9:30 AM ☐ | 10:00 AM ☐ | 10:30 AM ☑ |

SYSTEM FOR EVALUATING URINE FOR THE PRESENCE OR ABSENCE OF PREGNANEDIOL GLUCURONIDE AND OTHER HORMONES AND ANALYTES

CROSS-REFERENCE TO RELATED APPLICATIONS

This application is a continuation of U.S. patent application Ser. No. 16/732,823 filed on Jan. 2, 2020, now U.S. Pat. No. 11,061,026, issued Jul. 13, 2021, claiming priority to U.S. patent application Ser. No. 16/544,554 filed on Aug. 19, 2019 claiming the benefit of U.S. Provisional Patent Application 62/720,953 filed on Aug. 22, 2018, Ser. No. 16/381,229 filed on Apr. 11, 2019 which is a national stage application of PCT Application PCT/US18/68027 filed on Dec. 28, 2018 claiming the benefit of U.S. Provisional Patent Application 62/611,467 filed Dec. 28, 2017, and Ser. No. 15/974,229 filed on May 8, 2018 claiming the benefit of U.S. Provisional Patent Application 62/503,223 filed May 8, 2017 and separately claiming priority to U.S. patent application Ser. No. 15/900,794 filed on Feb. 20, 2018, now abandoned, which claims the benefit of U.S. Provisional Patent Application 62/460,307 filed on Feb. 17, 2017; and PCT Patent Application PCT/US20/40600 filed on Jul. 2, 2020; each of which is hereby incorporated by reference in its entirety with priority claimed thereto. This application claims the benefit of U.S. Provisional Patent Applications 63/023,116 filed on May 11, 2020 and 63/112,051 filed on Nov. 10, 2020, each of which is hereby incorporated by reference in its entirety with priority claimed thereto. This application is a continuation-in-part of U.S. patent application Ser. No. 17/308,149 filed on May 5, 2021, now U.S. Pat. No. 11,131,665, issued Sep. 28, 2021, claiming priority to U.S. patent application Ser. No. 16/732,766 filed on Jan. 2, 2020, now U.S. Pat. No. 11,029,321, issued Jun. 8, 2021, each of which is hereby incorporated by reference in its entirety with priority claimed thereto.

FIELD OF THE INVENTION

The present invention relates to the field of hormone diagnostics. More specifically, the present invention relates to urine based lateral flow assays for the detection of progesterone and methods of digital quantification thereof.

BACKGROUND OF THE INVENTION

Others have unsuccessfully attempted to create a urine-based test to provide information regarding progesterone levels by detecting and quantitating pregnanediol glucuronide (PdG) in a context other than in a lab environment, such as for at home for use by a non-expert user. Such attempts have proven fruitless due to inaccuracies associated with the tests with regard to the precision of detection and measurement of PdG. Further, the proper chemistry to enable the creation of such a test remains to be discovered. Specifically, it has yet to have been discovered how to create a progesterone test visible to the naked eye despite years of effort. Currently, progesterone tests remain limited to use within a lab environment. Colorimetric lab-grade electronic readers are used to detect differences in color otherwise imperceptible to the naked eye. Such lab-based tests determine concentrations to a high accuracy, often with the assistance of lasers. To create a test allowing one to visually review the results with the naked eye or without the assistance of laboratory-grade equipment, an alternative solution is needed. Previous attempts to create a lateral flow assay for detecting progesterone metabolites in urine, including the inventive matter disclosed in U.S. Pat. No. 6,924,153 granted on Aug. 2, 2005, the inventive matter disclosed in United Kingdom Patent Application Publication No. GB 2,204,398 A as published on Nov. 9, 1988, and similar prior art items, were unsuccessful due to the technical difficulties and inappropriate selection of component antibodies (namely the selection of component antibodies of improper isotypes) and type of carrier proteins. In certain cases, such difficulties also were associated with the development antigen and antibody chemistries of such ratios, component parts and/or elements to specifically produce visual results readable to the naked eye. Other prior art matter, for instance the subject matter disclosed in PCT/FR2016/050506 published on Mar. 4, 2016, only discloses Bovine Serum Albumin (BSA) without modification as the carrier protein, which is a commonly used carrier protein and inadequate without modification for usage in a urine-based progesterone or PdG testing solution intended to display results visible and discernable to the naked eye. Among other challenges associated with the solution disclosed in PCT/FR2016/050506, its disclosure of BSA as the carrier protein results in a testing solution lacking the ability to adequately bind to colloidal gold, due to its insufficient binding ratio, hereby resulting in a test delivering results that are problematically imperceptible to the naked eye to the necessary usable perception level. Moreover, these and other prior art solutions have failed to produce a product that reliably and reproducibly produced enough color intensity to deliver clear and easily interpreted test results to users with minimal training and a lack of specialized equipment. Therefore, a need remains for a lateral flow assay for detecting progesterone metabolites in urine that reliably and reproducibly delivers enough color intensity to portray clear and easily interpreted test results to users with minimal training and a lack of specialized equipment.

Prior art solutions are associated with challenges stemming from problematic antibody selection and incorporation, often due to the selection and incorporation of improperly chosen antibodies and antibody isotypes. A problem associated with prior art solutions is that the specifically chosen antibodies with such solutions are undesirably cross-reactive. In certain cases, chosen antibodies have suboptimal affinities for the application of a PdG test. The chosen antibodies in prior art solutions are outside of a desired detection range. For instance, the chosen antibodies in prior art solutions have resulted in a test that is not sensitive enough to allow a user to distinguish a positive and negative result. Sensitivity in such context may derive from suboptimal levels of affinity, avinity and specificity. In prior art tests where suboptimal sensitivity results from suboptimal specificity, the chosen antibody having a particular antibody isotype binds on items other than a PdG target. A problem with prior art tests having a particular suboptimal combination antibody, antibody isotype and/or carrier protein, is that the antibody and the conjugate do not bind with the precision necessary to produce a viable, reproducible test result useful to detect the presence of PdG. A further problem associated with such prior art tests is the lack of a system configured to collect, interpret and store the results of such tests.

BRIEF SUMMARY OF THE INVENTION

It is the object of the present invention to address several challenges in previous attempts to create a lateral flow assay to reproducibly and effectively detect PdG in urine. The present invention is an in-home lateral flow assay lateral flow assay that can be used to monitor PdG levels in urine, which correlate with progesterone levels in serum (hereinafter "PdG lateral flow assay"). The present invention has arrived at a specifically configured combination of elements to create a preferred embodiment of a lateral flow assay comprised of anti-pregnanediol glucuronide (PdG) antibodies of a specific isotype, namely IgG1, IgG1 Kappa, IgG2b or IgG3, conjugated to label; PdG conjugated specifically to a globulin or Bovine Serum Albumin as carrier protein covalently linked to bind to PdG antigens at 8-32 molecules per carrier protein; the membrane of the lateral flow assay providing a perceptible result for the presence or absence of PdG at or above a PdG threshold of 3-20 µg/ml; and in certain embodiments of the invention, a system for the tracking, interpretation and storage of results associated with such lateral flow assay incorporating a mobile device and an application as described herein.

BRIEF DESCRIPTION OF THE DRAWINGS

FIG. 26 depicts an exemplary graphical user interface associated with the scheduler.

DETAILED DESCRIPTION

Technical specifications associated with the novel construction of the preferred embodiments of a lateral flow assay test configured to evaluate for the presence or absence of at least pregnanediol glucuronide at a threshold are found within the following patent applications, with the benefit of priority claimed to each application: U.S. patent application Ser. No. 16/544,554 filed on Aug. 19, 2019; U.S. Provisional Patent Application 62/720,953 filed on Aug. 22, 2018; PCT Patent Application PCT/US18/68027 filed on Dec. 28, 2018; U.S. patent application Ser. No. 16/381,229 filed on Apr. 11, 2019; U.S. patent application Ser. No. 16/732,766 filed on Jan. 2, 2020, now U.S. Pat. No. 11,029,321, issued Jun. 8, 2021; U.S. patent application Ser. No. 15/900,794 filed on Feb. 20, 2018, now abandoned; U.S. patent application Ser. No. 15/974,229 filed on May 8, 2018; U.S. patent application Ser. No. 16/732,823 filed on Jan. 2, 2020, now U.S. Pat. No. 11,061,026, issued Jul. 13, 2021; and U.S. patent application Ser. No. 17/308,149 filed on May 5, 2021, now U.S. Pat. No. 11,131,665, issued Sep. 28, 2021, each of which are incorporated by reference herein with the benefit of priority claimed thereto. More specifically, the referenced applications describe generally a lateral flow assay comprising a sample pad, a conjugate pad saturated with an anti-PdG conjugated to a label, and a membrane comprising a testing zone. The preferred embodiment of the present invention incorporates such disclosures with a specific configuration discovered to solve persistent problems faced by prior art solutions.

In embodiments of the invention herein, the lateral flow assay comprises a sample pad, a conjugate pad saturated with monoclonal anti-pregnanediol glucuronide antibodies of an isotype selected from the group consisting of IgG1, IgG1 Kappa, IgG2a, IgG2b, and/or the IgG2c conjugated to a label in a concentration selected from within a range inclusive of 1-10 ug/mL, a membrane comprising a testing zone comprising PdG conjugated to a globulin or Bovine Serum Albumin covalently linked to bind to PdG antigens at 8-32 molecules per carrier protein, and the membrane providing a perceptible result for the presence of PdG at or above a PdG threshold of 3-20 µg/ml as indicated by the perceptible absence of the label in the first testing zone following the operation of the lateral flow assay and the absence of PdG at or above a PdG threshold of 3-20 µg/ml as indicated by the presence of the perceptible label in the testing zone following the operation of the lateral flow assay, as described further herein. Embodiments of the invention further comprise a system incorporating such a lateral flow assay in association with fertility tracking and the collection, interpretation and storage of results of at least one lateral flow assay configured as described above.

Figure 1:
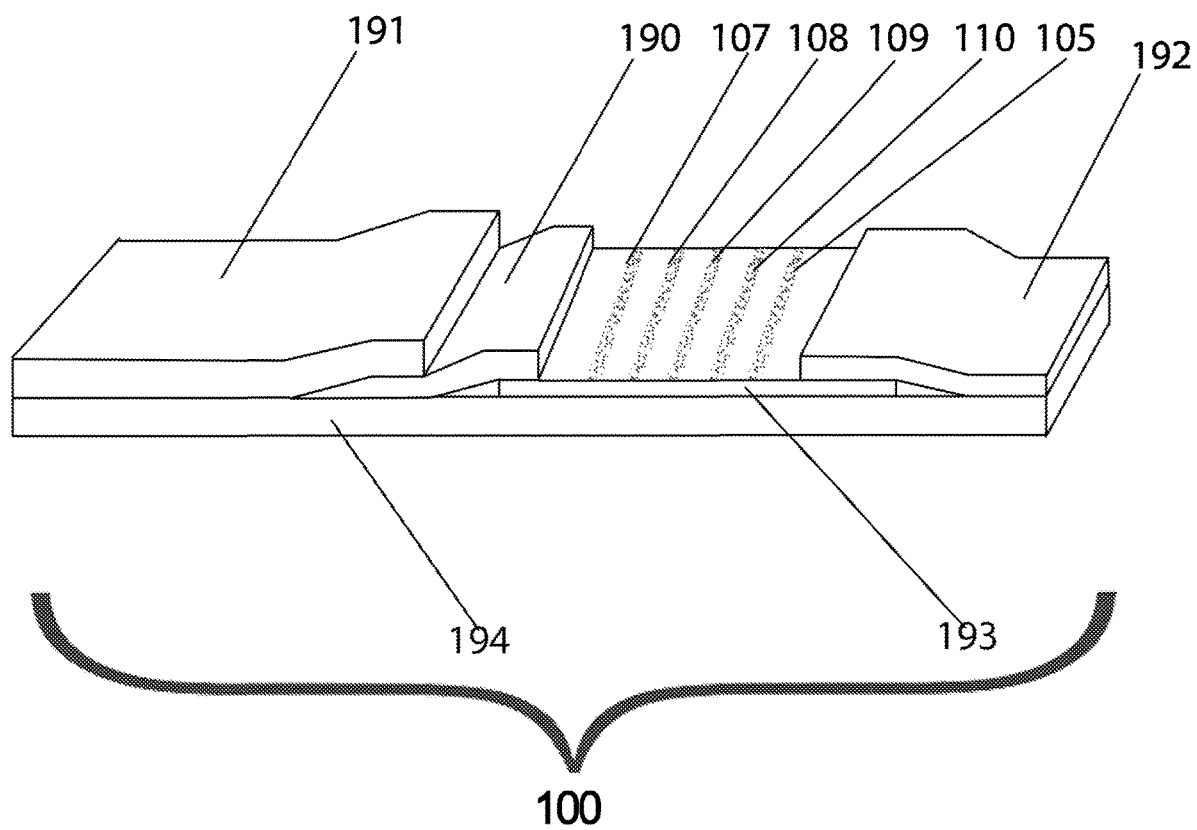
FIG. 1 depicts a configuration of an embodiment of the diagnostic test featuring four testing zones and four corresponding result indication lines associated with aspects of the invention, and specifically the location of the result indication lines associated with an exemplary configuration of the diagnostic test.

The preferred embodiment of the present invention comprises a testing system to detect the presence of PdG optimized for perceptible detection of a result via naked eye visualization or visualization following the application of fluorescent light in other than a laboratory context. The present inventor has recognized that in embodiments of the invention, the combination of mouse anti-PdG IgG1, IgG1 Kappa, IgG2a, IgG2b, and/or the IgG2c antibody conjugated to a label, such as colloidal gold and/or latex beads, and PdG conjugated to a globulin or Bovine Serum Albumin covalently linked to bind to PdG antigens at 8-32 molecules per carrier protein create sufficient binding partners for application to the conjugate pad of the lateral flow assay. Resultantly, the preferred embodiment of the invention comprises a visual test readable by the layperson in a context outside of a laboratory environment, optionally constructed as depicted in FIG. 1.

The preferred embodiment of the invention relies on the certain reagents being able to interact with other reagents to produce color in the testing zone of the membrane. Specifically, in the absence of PdG hormone in the urine sample, the following reagents must interact in order for the test results to be useful. In the preferred embodiment, the label, optionally colloidal gold, colored latex beads or a fluorescent label, must be conjugated to the anti-PdG antibody of an isotype selected from the group consisting of IgG1, IgG1 Kappa, IgG2a, IgG2b, and the IgG2c. in embodiments of the invention, the label conjugated anti-PdG antibody must interact with the PdG conjugated to a globulin or Bovine Serum Albumin covalently linked to bind to PdG antigens at 8-32 molecules per carrier protein. Moreover, the PdG conjugated to a globulin or Bovine Serum Albumin covalently linked to bind to PdG antigens at 8-32 molecules per carrier protein must bind the nitrocellulose membrane. The present inventor has recognized that for these embodiments to function as intended, these interactions between and among the label conjugated anti-PdG antibody and the PdG conjugated to a globulin or Bovine Serum Albumin covalently linked to bind to PdG antigens at 8-32 molecules per carrier protein are strong enough and stable enough to form and stay bound during urine sample application and lateral flow of urine across the reaction zone to solve the problems faced by the suboptimal prior art mechanisms.

The present inventor has discovered that since PdG is a small hormone metabolite, in order to strongly bind to the surface of a membrane, PdG requires a carrier protein covalently linked to bind to PdG antigens at 8-32 molecules per carrier protein, such as a globulin or Bovine Serum Albumin covalently linked to bind to PdG antigens at 8-32 molecules per carrier protein. However, the present inventor has discovered that, for the preferred embodiment of the invention to function as intended, not only does the strong carrier protein need to bind the nitrocellulose membrane, but the strong carrier protein also needs to bind the PdG and present it to the anti-PdG antibody. Prior to the embodiments of the invention as disclosed herein, other attempts in the prior art have failed to include an optimal combination of a strong carrier protein able to bind the PdG and present it to the anti-PdG antibody. The present inventor has discovered that in the case PdG and a carrier protein covalently linked to bind to PdG antigens at 8-32 molecules per carrier protein, such a ratio in the case where colloidal gold is a label, allows for the colloidal gold conjugated anti-PdG antibody to bind with both enough affinity and avidity to produce a bright enough color in the testing zone for typical users to distinguish visually.

The present inventor has further recognized that saturation of the conjugate pad of the lateral flow assay with monoclonal anti-pregnanediol glucuronide (anti-PdG) antibodies of an isotype selected from the group consisting of IgG1, IgG1 Kappa, IgG2a, IgG2b, and IgG2c conjugated to a label in a concentration selected from within a range inclusive of 1-10 ug/mL, with a membrane of the lateral flow assay comprising a testing zone comprising PdG conjugated to a globulin or Bovine Serum Albumin covalently linked to bind to PdG antigens at 8-32 molecules per carrier protein, enables the incorporation of a testing zone within the membrane of the lateral flow assay providing a perceptible result for the presence of PdG at or above a PdG threshold of 3-20 µg/ml as indicated by the perceptible absence of the label in the first testing zone following the operation of the lateral flow assay and the absence of PdG at or above a PdG threshold of 3-20 µg/ml as indicated by the presence of the perceptible label in the testing zone following the operation of the lateral flow assay as described elsewhere herein.

The present inventor has discovered a unique combination of specific elements to allow for the detection of pregnanediol glucuronide (PdG) formulated such as to enable the creation of a pregnanediol glucuronide (PdG) urine test. In embodiments of the invention Bovine Gamma Globulin (BGG) or Bovine Serum Albumin (BSA conjugated to PdG is combined with a mouse anti-PdG antibody of IgG1, IgG1 Kappa, IgG2a or IgG2c isotype. In an alternative embodiment of the invention, ovalbumin (OVA) is utilized as the carrier protein conjugated to PdG, which is combined with a mouse anti-PdG antibody of IgG1, IgG1 Kappa, IgG2a or IgG2c isotype at a binding ratio of 8-32 PdG antigens per carrier protein. In an alternative embodiment of the invention, keyhole limpet hemocyanin (KLH) is utilized as the carrier protein conjugated to PdG, which is combined with a mouse anti-PdG antibody of IgG1, IgG1 Kappa, IgG2a or IgG2c isotype at a binding ratio of 8-32 PdG antigens per carrier protein. The present inventor has recognized the above-mentioned carrier proteins (BGG, BSA, OVA, and KLH) advantageously either inherently exhibit or may be modified to achieve the preferred binding ratio of 8-32 PdG antigens per carrier protein without the need for the attachment or connection of a carbon or polyethylene glycol in accordance with the teachings elsewhere herein. The present inventor has recognized that such a specific combination uniquely allows for the label, optionally colloidal gold or a fluorescent label, to be conjugated to the anti-PdG antibody of one of the specific isotypes mentioned above, and for the colloidal gold conjugated anti-PdG antibody to interact with the PdG-BGG or PdG-BSA conjugate. Other combinations have been attempted, and have failed to allow the label to function to produce the color needed to allow the test results to be viewable visually by the naked and untrained (layperson) eye. The present inventor has noted that the utilization of BGG or BSA conjugated to PdG allows for anti-PdG antibody, specifically of the IgG2b isotype or the IgG1 Kappa isotype, to bind in such a manner that the label is carried at a concentration sufficient for perception via naked eye visualization or fluorescent detection. The present inventor notes that Globulins evidence the preferable binding ratio of 8-32 PdG antigens per carrier protein, which favor presentation of a visual result perceptible to the naked eye or to a reader. The present inventor also notes that Bovine Serum Albumin, with modification (optionally by increasing the incubation time, i.e. from 6.5 hours to a much longer time, for example 24 hours, or by increasing the amount of the PDG sulfo-Nhydroxysuccinimide ester), the conjugation ratio may be increased such that the preferable binding ratio of 8-32 PdG antigens per carrier protein in the PdG-carrier protein conjugate may be achieved with the use of Bovine Serum Albumin as the carrier protein, which favors presentation of a visual result perceptible to the naked eye or to a reader. It is therefore a teaching of embodiments of the invention to comprise a carrier protein demonstrating the binding ratio of 8-32 PdG antigens per carrier protein. The present inventor has recognized the benefit associated with embodiments of the invention described herein that a PdG test may be producible allowing the results to be visually interpreted with the naked eye. The present inventor has recognized the benefit associated with embodiments of the invention that a PdG test may be producible allowing the results to be visually interpreted with the naked eye.

The present inventor has discovered that because PdG is a small hormone metabolite, in order to strongly bind to the surface of a membrane, PdG requires a strong carrier protein, which is a teaching of an embodiment of the invention. However, the present inventor has discovered that, for the preferred embodiment of the invention to function as intended, not only does the strong carrier protein need to bind the nitrocellulose membrane of the lateral flow assay, but the strong carrier protein also needs to bind the PdG and present it to the anti-PdG antibody, which is a teaching of an embodiment of the invention.

Such teachings as disclosed herein, solve the challenges associated with suboptimal prior art teachings, which lacked the ideal combination of a strong carrier protein able to bind the PdG and present it to the anti-PdG antibody.

In accordance with teachings of the invention, the lateral flow assay relies on the certain reagents being able to interact with other reagents to produce color in the testing zone of the membrane. Specifically, in the absence of PdG hormone in the urine sample, the following reagents must interact in order for the test results to be useful. First, in the preferred embodiment, colloidal gold must be conjugated to the immunologically active anti-PdG antibody of one of the specific IgG isotypes described elsewhere herein. In alternative embodiments, as a replacement for colloidial gold in other embodiments described herein, an alternative visual dye such as latex beads may be utilized to a similar effect. Further, in embodiments of the invention, the colloidal gold conjugated anti-PdG antibody must interact with the PdG-carrier protein conjugate. Moreover, the PdG-carrier protein must bind a nitrocellulose membrane. The present inventor has recognized that for these embodiments to function as intended, these interactions between and among the colloidal gold conjugated anti-PdG antibody and the PdG-carrier protein conjugate, must be strong enough and stable enough to form and stay bound during urine sample application and lateral flow of the fluid across the reaction zone to solve the problems faced by the suboptimal prior art mechanisms described elsewhere herein. The disclosures in this paragraph constitute teachings of an embodiment of the invention.

In association with teachings of the invention, the lateral flow assay is configured to comprise a conjugate of a carrier protein demonstrating the binding ratio of 8-32 PdG antigens per carrier protein, optionally a Globulin carrier protein, with PdG. Such PdG-carrier protein conjugate is combined with a mouse anti-PdG antibody of one the class of the IgG isotypes in an embodiment. The class of Ig isotypes includes IgG1, IgG2b, IgG1 Kappa, IgG2a or IgG2c isotype as contemplated in association with embodiments of the invention. The conjugation of a carrier protein to PdG, and the combination of the PdG-conjugated carrier protein with a mouse anti-PdG antibody of Ig isotype is accomplished in accord with general conjugation procedures as well-known by those skilled in the art. In embodiments of the invention, one carrier protein is conjugated to eight or more PdG molecules. In the preferred embodiment, the one carrier protein is conjugated to no more than thirty-two PdG molecules. The present inventor has discovered that such a ratio allows for the colloidal gold conjugated anti-PdG antibody to bind with both enough affinity and avidity to produce a bright enough color in the test reaction zone for typical users to distinguish visually. The present inventor has discovered the specific property of Globulin enabling such combination. In embodiments of the invention, as Globulin inherently exhibits the optimal number of active sites optimally spaced, the inclusion of Globulin results in a lesser amount of steric hindrance, and therefore embodiments of the invention are enabled to receive and bind PdG at sufficient ratios. However, in accordance with the teachings herein, the present inventor has recognized that Bovine Serum Albumin, Ovalbumin or Keyhole Limpet Hemocyanin may also achieve the optimal ratio wherein one carrier protein is conjugated to eight or more PdG molecules and no more than thirty two PdG molecules. Therefore, Globulin, Bovine Serum Albumin, Ovalbumin or Keyhole Limpet Hemocyanin is useful as the carrier protein in association the preferred embodiment of the invention to function as intended. In the preferred embodiment of the invention, therefore, PdG is conjugated to a Globulin, Bovine Serum Albumin, Ovalbumin or Keyhole Limpet Hemocyanin. In embodiments of the invention, the testing zone is configured to comprise a progesterone metabolite, optionally pregnanediol (PdG), conjugated to a Globulin, Bovine Serum Albumin, Ovalbumin or Keyhole Limpet Hemocyanin carrier protein at a concentration of a value selected from the range of 0.5 pg/ml-2 pg/ml within the testing zone. In an embodiment of the invention, the Globulin carrier protein consists of Bovine Gamma Globulin (BGG). The present inventor has recognized that the application of the PdG-carrier protein conjugate at the concentration levels described above, when applied to the lateral flow assay in conjunction with the application of the anti-PdG of a specified IgG isotype, optionally IgG1 Kappa or IgG2b, conjugated to a label of the specific concentration levels described herein, accomplishes the proper ratio of those specific binding partners to enable the lateral flow assay to detect for the presence of PdG in a sample of urine applied to the lateral flow assay at the pre-defined thresholds described above and further visually indicate that the sample of urine contains PdG above the pre-defined threshold or visually indicate that the sample of urine does not contain PdG above the pre-defined threshold. During a configuration step associated with conjugating in an embodiment, PdG is conjugated to a specified Globulin, Bovine Serum Albumin, Ovalbumin or Keyhole Limpet Hemocyanin as a carrier protein, and, separately, a mouse anti-PdG antibody chosen from the group of isotypes including IgG1, IgG1 Kappa, IgG2a, IgG2b or IgG2c is conjugated to colloidal gold. In the configuring step, to create the lateral flow assay, the PdG-Globulin, PdG-Bovine Serum Albumin, PdG-Ovalbumin or PdG-Keyhole Limpet Hemocyanin conjugate is impregnated or striped onto the nitrocellulose membrane in the testing zone of the lateral flow assay. Colloidal gold conjugated anti-PdG antibody is applied or soaked into the receiving zone of the lateral flow assay. When a fluid sample containing PdG is applied, the free PDG will bind to the anti-PDG antibody and travel to the testing zone of the lateral flow assay. Any unbound anti-PDG antibody will bind to the testing zone area and produce a colored line. In this type of competitive assay format, the absence of color (optionally a fluorescent) in the testing zone indicates a positive test result for the presence of a progesterone metabolite, and the presence of color (optionally a fluorescent) in the testing zone indicates a negative result for the presence of a progesterone metabolite. the membrane providing a perceptible result for the presence of PdG at or above a PdG threshold of 3-20 μg/ml as indicated by the perceptible absence of the label in the first testing zone following the operation of the lateral flow assay and the absence of PdG at or above a PdG threshold of 3-20 μg/ml as indicated by the presence of the perceptible label in the testing zone following the operation of the lateral flow assay.

Utilization of a Globulin, Bovine Serum Albumin, Ovalbumin or Keyhole Limpet Hemocyanin conjugated to PdG allows for anti-PdG antibody of an immunologically active IgG isotype, to bind in such a manner that colloidal gold is carried at a concentration sufficient for naked eye visualization, and is therefore a teaching of embodiments of the invention. The present inventor notes that Globulins, Bovine Serum Albumin, Ovalbumin or Keyhole Limpet Hemocyanin (in the case of the latter three carrier proteins, when modified as described herein) generally evidence the preferable binding ratio of 8-32 PdG antigens per carrier protein, which favor presentation of a visual result perceptible to the naked eye or to a reader, and is therefore a teaching of embodiments of the invention. The inventor notes, however, that non-Globulin carrier proteins (especially Bovine Serum Albumin, Ovalbumin and Keyhole Limpet Hemocyanin) may bind to PdG in accordance with the preferable binding ratio of 8-32 PdG antigens per carrier protein. For example, as described in U.S. Pat. No. 7,144,742 dated Dec. 5, 2006 and incorporated by reference, while not inclusive or descriptive of a method of modifying a BSA conjugate to achieve the desired PdG antigen-carrier protein ratio, a method of Conjugation of Pregnanediol Glucuronide to Bovine Serum Albumin (PDG-BSA Conjugate) is described. Bovine Serum Albumin, 40 mg, (Armour) was dissolved in 3.96 ml 0.10 M sodium bicarbonate sodium carbonate buffer, pH 9.0, and chilled in ice water. The dimethylformamide solution of PDG sulfo-N-hydroxysuccinimide ester, 848 mg, was added slowly with rapid stirring over 10 minutes to give an opalescent solution. The solution was incubated at 18-25° C. for 6.5 hours. It was them applied to a 40 cm3 column containing Sephadex G-25 (Pharmacia) equilibrated with PBS buffer to separate the conjugated protein from unconjugated PDG, dimethylformamide, and reaction products. The conjugate was stored frozen at −20° C. Additionally, the present inventor has recognized that in accordance with mechanisms known by those skilled in the art, (for instance in the example associated with a PdG-BSA conjugate, increasing the incubation time, i.e. from 6.5 hours to a much longer time, for example 24 hours, or by increasing the amount of the PDG sulfo-Nhydroxysuccinimide ester), the conjugation ratio may be increased such that the preferable binding ratio of 8-32 PdG antigens per carrier protein in the PdG-carrier protein conjugate may be achieved with the use of Bovine Serum Albumin (or Ovalbumin or Keyhole Limpet Hemocyanin) as the carrier protein. The present inventor has recognized the benefit associated with the embodiments of the invention as described herein in that a PdG test may be producible allowing the results to be visually interpreted with the naked eye. In alternative embodiments of the invention, the carrier protein comprises one of the following human, non-human, or plant globulins: vicilin, legumin, casein, Alpha 1-antichymotypsin, seruam amylid A, Alpha 1-lipoprotein, Haptogolulin, Alphy 2-antiplasmin, Protein C, Angiotensinogen, cortisol binding protein, beta-2 microglobulin, plasminogen, angiostatins, sexhormone-binding protein, transferrin, fibronectin, microglobulin, gamma globulin, thyroglobulin, 11S globulin family, 7S family of globulins. In various embodiments, the Globulin serving as the carrier protein derives from a plant or animal source, including an animal source such as human, mouse, rat, bovine, equine, goat, or rabbit. The present inventor has discovered that while Globulin carriers more generally inherently demonstrate the favorable conjugation ratio of 8-32 antigens per one carrier protein, it may still be advantageous to modify the carrier protein-PdG ratio as described herein, and also that other non-Globulin carrier proteins such as Bovine Serum Albumin, Ovalbumin or Keyhole Limpet Hemocyanin may be present in a PdG-carrier protein conjugate modified as described herein and still accomplish better than Globulins generally the favorable ratio of 8-32 antigens per one carrier protein in accordance with mechanisms to increase conjugation ratios as known in the art.

It is a further teaching of the invention that in order for the preferred embodiment of the invention to function as intended, the specifically chosen anti-PdG antibody needs to be monoclonal, due to the nature of the PdG antigen presentation on the PdG-carrier protein conjugate. In order for the embodiments of the invention to function as intended, the specifically chosen anti-PdG antibody must incorporate one of the following isotypes: IgG1, IgG1 Kappa, IgG2a, IgG2b, or IgG2c. The present inventor has discovered that isotypes other than IgG1, IgG1 Kappa, IgG2a, IgG2b, or IgG2c, including but not limited to IgM, IgS, and IgE anti-PdG antibody isotypes, remain unable to effectively bind the colloidal gold (or other visual label) and produce a strong enough color signal on the reaction zone due to their size and structure in accordance with the teachings of the preferred embodiment invention. Since the colloidal gold must bind the 1 g region of the anti-PdG antibody, the present inventor has discovered that the IgG1, IgG1 Kappa, IgG2a, IgG2b, and IgG2c isotypes of the anti-PdG antibody sufficiently bind colloidal gold and are therefore incorporated into embodiments of the invention. As a result, the IgG1, IgG1 Kappa, IgG2a, IgG2b and IgG2c isotypes of the anti-PdG antibody therefore produce the strongest color in accordance with teachings of embodiments of the invention. In the preferred embodiment of the invention, the IgG2b or the IgG1 Kappa isotype is included in the invention, as the present inventor has recognized that the IgG2b or the IgG1 Kappa isotype performs slightly better when producing color. Therefore, the preferred embodiment of the invention incorporates the IgG2b or the IgG1 Kappa isotype of the anti-PdG antibody. Alternative embodiments of the invention incorporate the IgG2a, IgG2c or non-IgG1 Kappa IgG1 isotypes of the anti-PdG antibody.

As referred to herein, a monoclonal anti-PdG antibody as described herein, and more specifically a monoclonal anti-PdG antibody having the necessary binding affinity for PdG such that when used in association with the invention as described herein it is capable of yielding a detection threshold of PdG of 3-20 µg/mL, has been deposited in accordance with the provisions of the Budapest Treaty at the American Type Culture Collection (ATCC), located at the following address: 10801 University Boulevard, Manassas, Va. 20110 USA on Apr. 23, 2021. The accession number of the deposit is Patent Deposit Number PTA-127054. The deposited material is a biological material specifically identified in the application, namely a monoclonal anti-PdG antibody as specifically referred to herein.

Fertility Tracking System

An embodiment of the invention comprises a lateral flow assay, optionally the lateral flow assay as described elsewhere herein, and various components to capture an image of the lateral flow assay including an optical device (optionally a camera associated with a smartphone or mobile device), a computing device (optionally a smartphone or mobile device), an application, storage, a graphical user interface, and a calendar.

In various embodiments, to retrieve the observable positive result on the membrane of a lateral flow assay, an optical reader utilized in association with a computing device is used. In various embodiments, the optical reader may comprise the camera of a smart phone. In various embodiments of the invention, a base unit 4001 associated with a lateral flow assay as described herein comprises the optical reader. In an example, the optical reader is configured to capture an image of the lateral flow assay as described herein and detect result indication line within a testing zone, the result indication line configured to provide a optical, visual and/or fluorescent result for the presence or absence of PdG at a threshold. The present inventor has recognized that by presenting at least 8 PdG molecules to each of the label-conjugated anti-PdG antibodies, optionally to generate a fluorescent result via fluorescent label-conjugated anti-PdG antibodies, this results in the efficient binding and reactivity from the PdG-carrier protein and antibody, and thereby enables the proper functionality of the result indication line as a perceptible result, whether visual, optical, or fluorescent, relevant to the presence or absence of PdG at a threshold in an applied fluid associated with the preferred embodiment of the diagnostic test 100.

In an embodiment, the application is programmed to associate the indication detectable in association with a result indication lines on the lateral flow assay each located at the distances as specified above, or at alternative distances in accordance with the specific configuration of the lateral flow assay, from at least one end of the lateral flow assay. Each specific indication present at a distance, optionally in association with a color intensity as described elsewhere herein, is pre-associated with an interpretation for the presence or absence of a specific hormone or analytes, optionally at a threshold or in association with a pre-determined concentration, in accordance with the teachings elsewhere herein. It is a teaching of an embodiment that the manufacturing processes associated with such lateral flow assays are so configured to reproduce lateral flow assays in a standardized manner such that the digital reader 670 and/or application, optionally in association with other elements of the system, may be preprogrammed with the one distance or plurality of distances from one end of the lateral flow assay, and the association of the one distance or plurality of distances from one end of the lateral flow assay each with a distinct hormone or analyte. Additionally, the digital reader 670 and/or the application in an embodiment is additionally pre-programmed with the color intensity, with is optionally determined in advance by spiking a sample of male urine with the specific threshold of hormone or analyte and detecting the color intensity displayed in a testing zone following the application of the sample to the lateral flow assay to establish the color intensity associated with the threshold to indicate the presence or absence of such hormone or analyte for subsequent use in association with configuring the system. In an embodiment, a Diagnostic Test Key is preconfigured within the digital reader 670, application and/or smartphone 600, optionally in association with other elements of the system, via coding and computer programming mechanisms as well understood by those skilled in the art. In one example of the above, a smartphone featuring a camera is utilized to photograph and identify the shape of the diagnostic test 100 consisting of a lateral flow assay and calculate the distance from one end with preprogrammed dimensions of the lateral flow assay, and optionally via the use of the Pythagorean Theorem, to determine the dimensions of the lateral flow assay and location of the result indication line, optionally by calculating the color intensity in each testing zone and comparing it to the pre-programmed color intensity of the threshold, or optionally by detecting the HEX or RGB color number displayed on each result indication line and comparing it to a pre-programmed HEX color number, RGB color number or other color identifier associated with a specific quantity of hormone or hormone analyte optionally in comparison to the HEX color number, RGB color number or other color identifier associated with one or more colors displayed on the color intensity key and/or the Diagnostic Test Key 200 and associated with a quantity of the PdG indicated by the result indication line within the testing zone of the lateral flow assay.

It is a teaching of an embodiment of the invention to utilize the color intensity correlation to the threshold to facilitate the collection and digitization of a result of the diagnostic test 100 optionally consisting of a lateral flow assay in accordance with the teachings elsewhere herein, and to pre-program the application and/or digital reader 670, optionally in association with the other elements of the system, by use of such color intensity or color intensities of the one or more result indication lines associated with the presence of PdG and/or other hormones or analytes in an applied fluid and optionally each associated with a specific distance from one end of the lateral flow assay, to preconfigure and enable functioning of the system in accordance with coding and computer programming mechanisms as well understood by those skilled in the art. In an example, the Diagnostic Test Key 200 is configured to incorporate such color intensity or color intensities to a threshold or thresholds of different hormones and/or analytes, optionally at specified locations on the lateral flow assay.

In an embodiment, prior to capturing a photograph of a diagnostic test, the application is configured to detect a predominantly white area of the photograph of a diagnostic test and to check whether the RGB values correspond to an range of white values corresponding to acceptable levels of brightness in the environment where the diagnostic test was photographed. In such embodiment, if the RGB value detected in the predominantly white area of the photograph of the diagnostic test falls outside the range of acceptable levels of brightness in the environment where the diagnostic test was photographed, the application may be configured to instruct the user to re-photograph the test in an environment with the requisite brightness levels. In another embodiment, the application may be configured to analyze the sharpness of the photograph of the diagnostic test and instruct the user to re-take the photograph of the diagnostic test if the sharpness does not meet or exceed the requisite sharpness level. In exemplary embodiments, the sequence of the testing zones is detected and interpreted with the assistance of one or more digital readers 670, in association with methods as well understood by those in the art, such as those described in PCT Patent Application PCT/CN2017/085010 filed on May 19, 2017 and corresponding U.S. patent application Ser. No. 16/302,085 filed on May 29, 2019, and PCT Patent Application PCT/US2018/038173 filed on Jun. 20, 2019 claiming priority to U.S. Patent Application 62/688,970, each of which is incorporated by reference.

Figure 2:
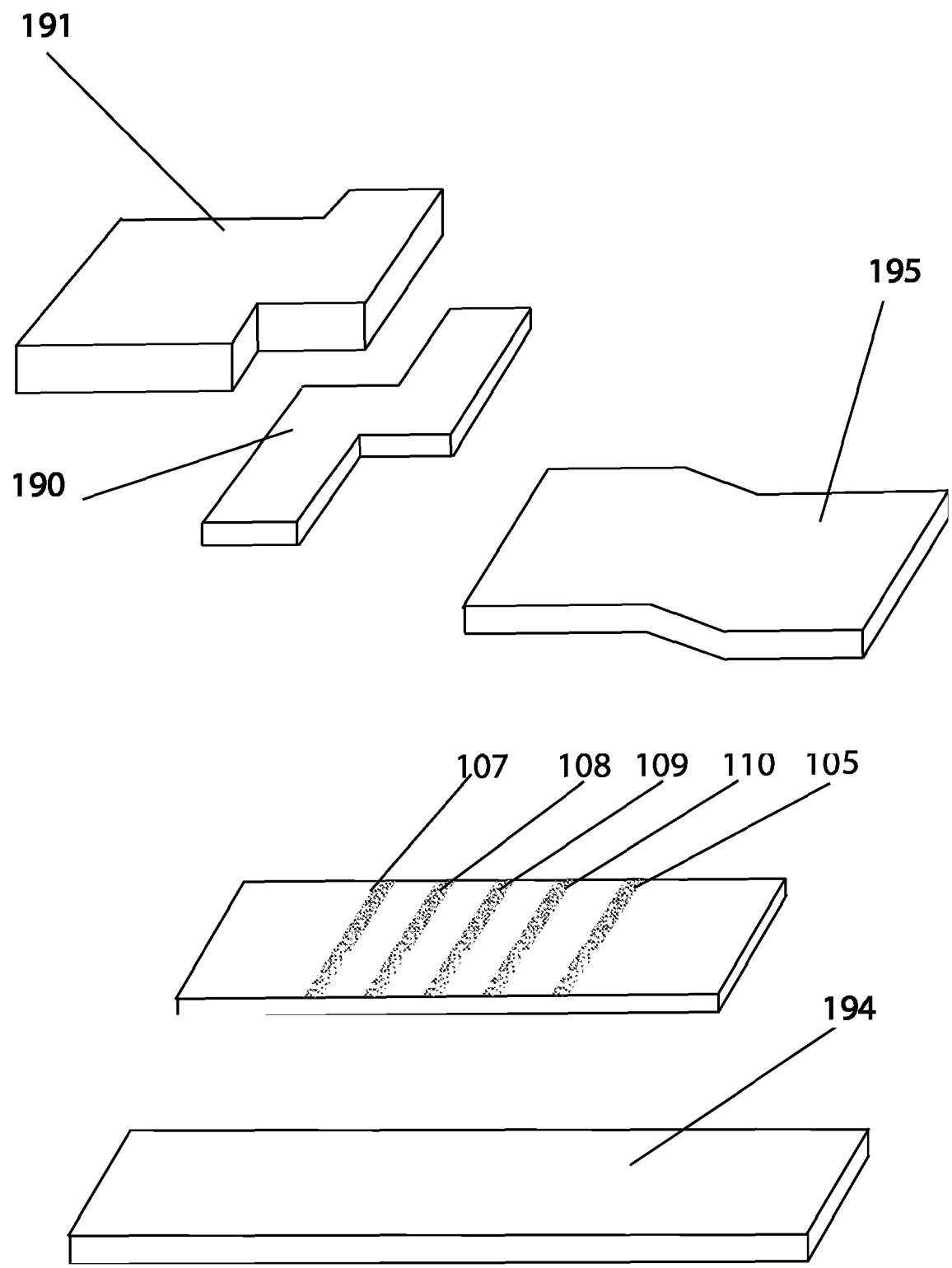
FIG. 2 depicts an exploded view of an embodiment of the diagnostic test featuring four testing zones and four corresponding result indication lines associated with aspects of the invention, and specifically the location of the result indication lines associated with an exemplary configuration of the diagnostic test.

In one exemplary embodiment, as depicted in FIGS. 1 and 2, the second result indication line 108 is configured to provide an indication for the presence or absence of luteinizing hormone at a threshold, the first result indication line 107 is configured to provide an indication for the presence or absence of progesterone glucuronide and the control line 105 is configured to provide a visual indication upon the application of any fluid, to ensure that the fluid has passed through each of the testing zones and each of the result indication lines present within the diagnostic test 100 from the fluid application zone. In various embodiments, the control line 105 is the most distal from the fluid application zone, and must pass through the one or more testing zones and the one or more result indication lines to provide a visual indication that the lateral flow assay has been performed correctly. Each analyte and/or hormone tested in each testing zone of a diagnostic test 100 as indicated by a corresponding result indication line, and/or the control line 105, optionally corresponds to a different label to produce a distinct color (such as colloidal gold, a fluorescent and/or latex beads).

Figure 3:
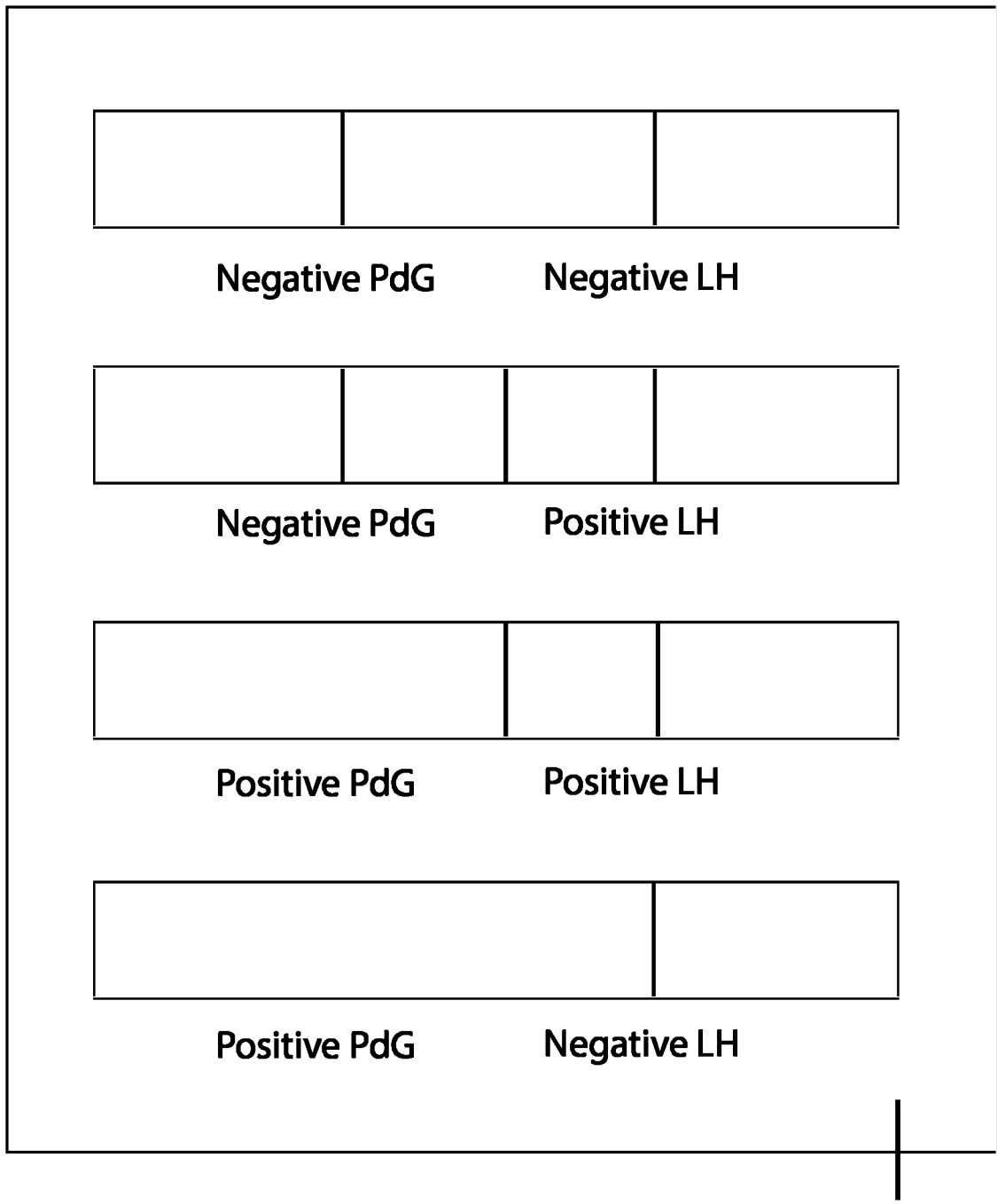
FIG. 3 depicts an exemplary diagnostic test key corresponding to an embodiment of the diagnostic test configured to evaluate specifically for the presence or absence of PdG at a threshold and the presence or absence of LH at a threshold.
Figure 4:
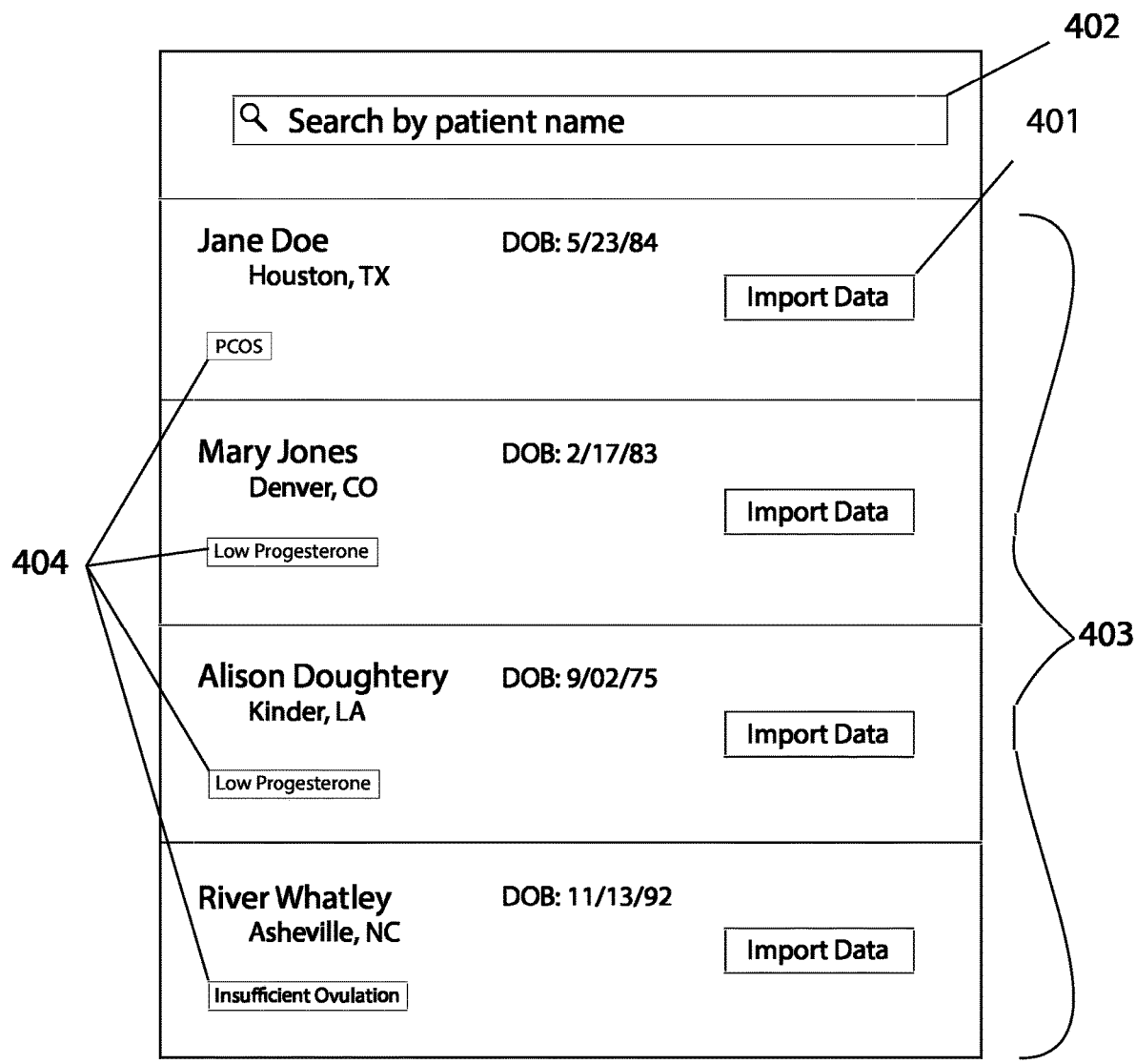
FIG. 4 depicts an exemplary graphical user interface of the Healthcare Professional-Facing Application specifically configured to display a list of one or more patients and provide the capability to search for a patient.

As illustrated by FIG. 1 in an example, the first result indication line 107 appears on the lateral flow assay at a distance selected from within the range of 25-45 mm from the end at which a fluid is applied and the second result indication line 108 appears at a specified and differentiated distance on the lateral flow assay from a distance range selected from the range including 28-50 mm from the end at which a fluid is applied. In an embodiment, the third result indication line 109 appears on the lateral flow assay at a distance selected from within the range of 35-55 mm and the fourth result indication line 110 appears at a specified and differentiated distance on the lateral flow assay from a distance range selected from the range including 38-58 mm from the end at which a fluid is applied. In various embodiments, the control line 105 is located distal from the end at which a fluid is applied at a distance selected from the range of 2-10 mm from the edge of the testing zone located most distal from the end at which a fluid is applied. In an embodiment, the first result indication line 107 appears on the lateral flow assay at a distance of 29 mm from the end at which a fluid is applied, the second result indication line 108 appears on the lateral flow assay from a distance range of 32 mm from the end at which a fluid is applied. In an embodiment, the specific sequence of the each result indication line (or the locations thereof, for example, in the absence of an indicated line where the absence of an indicated line at the location of a result indication line signifies a result) on the diagnostic test 100 and the control line 105 is associated with a specific sequence of hormones and/or analytes tested by the diagnostic test 100 and correlates to information provided in association with a Diagnostic Test Key 200 which optionally is included within system embodiments of the invention, or pre-programmed on a digital reader 670 or an application for use in association with associating the each result indication line with a specific hormone or hormone analyte. In an embodiment, the sequence of each result indication line depicted in association with a Diagnostic Test Key 200 is utilized as an alternative to distinct color labeling of each analyte and/or hormone tested to provide a representation of which distinct analyte and/or hormone is indicated on each result indication line of a diagnostic test 100. In an embodiment, the presence or absence of result indication lines in a pre-defined sequence is programmed and/or coded in association with a application which may be utilized to detect the presence or absence of each hormone as a result of the specific indications of a diagnostic test 100. The present inventor has recognized the importance of external mechanisms such as the application and/or Diagnostic Test Key 200 in association with the utilization of the preferred embodiment of the diagnostic test 100, as some hormones or analytes such as PdG are associated with the absence of a visual indication line to indicate a positive result, whereas distinct hormones or analytes such as LH are associated with the presence of a visual indication line to indicate a positive result. Further, especially due to the possibility that the presence of one line may indicate a positive result and the presence of a separate and distinct line on the same strip may indicate a negative result, for instance as indicated on a printed Diagnostic Test Key 200 embodiment illustrated by FIG. 3, an external mechanism such as a printed Diagnostic Test Key 200, an application, or a Diagnostic Test Key coded into a application is transformative in facilitating layperson understanding of the visual results indicated on a diagnostic test 100. In an embodiment, the Diagnostic Test Key 200 comprises a printed card featuring a graphical depiction of each possible visual result of the diagnostic test, and what each possible visual result of the diagnostic test indicates, in an embodiment as depicted in FIG. 3. In an embodiment, the Diagnostic Test Key 200 comprises a digitized graphic, or a virtual representation generated in association with coded instructions, for utilization in association with an application, optionally the Patient-Facing Application, as described elsewhere herein and/or a digital reader 670 as described elsewhere herein. In an embodiment, the Diagnostic Test Key 200 comprises a digitized map of the correlation of the presence or absence of a specified color intensity (optionally represented by HEX or RGB codes) at a of specified location measured from one end of the lateral flow assay on a photographed lateral flow assay corresponding to the presence or absence of a hormone or analyte in a tested bodily fluid. In an embodiment, the Diagnostic Test Key 200 comprises multiple correlations of the presence or absence of a specified color intensity at a of specified location directed to a single lateral flow assay. In an example, configuration of the Diagnostic Test Key 200 comprising a digitized map may be made available to the Patient Facing Application in association with the other components of the system described herein and in accordance with computer application configuration mechanisms (i.e. code) as is well understood in the art. In an exemplary embodiment, a result indication line configured to provide a result for the presence or absence of PdG at a threshold in an applied fluid sample and a separate result indication line configured to provide a result for the presence or absence of LH at a threshold in an applied fluid sample is depicted in association with the Diagnostic Test Key, an example of which as shown on FIG. 3. In an example, the Diagnostic Test Key 200 depicts a diagnostic test 100 at least featuring a result indication line configured to provide an indication with regard to an applied fluid sample for the presence or absence of PdG at a threshold whereby the absence of a visual line, or the presence of a visual line below a specified color intensity, indicates the presence of PdG at the threshold in the applied fluid sample. In an example, the Diagnostic Test Key 200 depicts a diagnostic test 100 further comprising a result indication line configured to provide an indication with regard to an applied fluid sample for the presence or absence of LH at a threshold whereby the presence of a visual line, or the presence of a visual line above a specified color intensity, indicates the presence of LH at the threshold in the applied fluid sample. In an embodiment of the invention the Diagnostic Test Key 200 depicts at least one printed graphical representation of a diagnostic test 100 at a similar scale to the diagnostic test 100 with exemplary results depicted thereon alongside a verbal description of the exemplary results. It will be appreciated by those skilled in the art that a variety of diagnostic tests for uses in association with a variety of contexts may be collected, read and interpreted by the application, for example either by color labeling or by the sequence of the hormones and/or analytes being tested on the diagnostic test 100.

In various embodiments of the invention, a diagnostic test 100 consisting of a lateral flow assay further comprises a visual label configured to display or not display a specific color based indicating the presence or absence of a hormone or hormonal analyte within a fluid sample placed into contact with the lateral flow assay. In an example, the presence or absence of a color at a specified intensity provides an indication of the presence or absence of a hormone or hormonal analyte within a fluid sample placed into contact with the lateral flow assay. In an example of the diagnostic test, the labels (such as colloidal gold) are varied, with a separate and distinct label configured to attach to a separate and distinct hormone or analyte. In such example, the present inventor has recognized the advantage that the diagnostic test 100 is configured to provide a different color for each distinct hormone and analyte indicating either the presence or absence of each hormone analyte at a threshold following application of urine to the diagnostic test. In an embodiment, the diagnostic test 100 is configured as a lateral flow assay comprising a conjugate pad 190 (the conjugate pad also optionally referred to as the "receiving zone") comprising anti-PdG antibody-collodial gold conjugate placed to form a testing zone, and at least one other conjugate placed within another testing zone. In an embodiment, the at least one other conjugate comprises anti-LH antibody-conjugated with a different label, optionally differently colored latex beads. In various embodiments, the configurations of the diagnostic test 100 featuring a different color representing an indication of the presence or absence of a distinct hormone or analyte are as described in U.S. patent application Ser. No. 16/381,229 filed Apr. 11, 2019, and PCT Application No. PCT/US18/68027, filed Dec. 28, 2018, each of which are incorporated by reference with priority claimed thereto.

In accordance with such teachings and the components of the system as described elsewhere herein, the method of use of the system comprises the step of determining a result from a lateral flow assay test configured to detect for at least one additional hormone or hormonal analyte (other than PdG) from the group consisting of: the presence or absence of luteinizing hormone at a threshold at a threshold, the presence or absence of and human chorionic gonadotropin at a threshold, the presence of E3G in a concentration correlating to a color intensity, and the presence of FSH in a concentration correlating to a color intensity 2009.

In various embodiments of the invention, a positivity scale 5685 is useful in association with interpreting the results of the diagnostic test 100 in certain examples. The positivity scale 5685 in the preferred embodiment comprises a line chart featuring various colors or various shades of the same color each color or shade corresponding to a value on the diagnostic test 100. The present inventor has recognized the advantage of such positivity scale 5685 to provide a visual and relative indication to an observer of how close to a certain value the diagnostic test 100 actually is. In one example, the positivity scale 5685 is useful in providing an indication of how close to a threshold, indicating a positive or negative result, the result indicated upon a diagnostic test 100 actually is. In various examples, a value indication 5689 is displayed along the positivity scale to give a relative sense to the user of how far from the threshold of the diagnostic test as indicated in association with the positivity scale 5685 by a threshold indicator 5687 the result of the diagnostic test actually is.

In an embodiment of the invention, the positivity scale 5685 forms an element of the graphical user interface of an application, optionally the Patient Facing Application described herein, running on a smart device, such as a smartphone optionally running the iOS operating system or the Android OS operating system. In such example, the positivity scale 5685 is useful in associating a color value assigned by the application to a color indicated on the diagnostic test 100 as photographed by a camera of the smart device, and depicting that color value on some point along the positivity scale 5685. In one example, if the color value corresponds to a quantity of a detected hormone or analyte in a fluid applied to the diagnostic test 100, the color value may be indicated on or near the positivity scale depicted within the graphical user interface along with an estimation of the quantity of the detected hormone or analyte present in the fluid applied to the diagnostic test 100, an example of which is depicted in FIG. 1.

Various embodiments of the invention comprise an application configured to operate on a smart device, optionally the Patient-Facing Application as referenced herein. As utilized in association with the description of a Patient-Facing Application, the term "application" is synonymous with a computer program. In an embodiment, the term "application" means a computer program designed to run on a computing device, such as a smartphone. It is to be understood that the term "patient" when used in association with the terms "Patient-Facing Application" and/or "patient user" is a term of convenience and not necessarily literally intended to refer to or designate any user as a patient. Rather, the term "patient" in these contexts refers to persons that are not healthcare professionals, persons seeking health information or healthcare services, or persons not intended to use the associated features and components in the context of providing healthcare services. In alternative embodiments, the term "application" refers to a computer program designed to run on an alternative computing device such as a personal computer.

The application comprises a Patient-Facing Application in various embodiments. The Patient-Facing Application in an embodiment incorporates a patient profile. The patient profile displayed to a patient user via a graphical user interface allows for the patient user to input demographic information associated with the patient. In an example, the patient profile is made accessible to a patient validated and logged into the Patient-Facing Application (referred to herein as the "patient user") in association with methods and mechanisms readily understood by those skilled in the art. In an example, the patient user consists of the subject woman of a diagnostic test configured to detect for at least the presence or absence of pregnanediol glucuronide at a specific threshold. Optionally, the patient may manually input other electronic personal health information or otherwise import or link to the patient's electronic personal health information, optionally by importing a continuity of care document or continuity of care record. In an example, the patient profile allows for the input of desired characteristics of healthcare professionals that the patient would like to interact with, optionally demographic information or jurisdictions of licensure. In an example, the patient profile allows for the input of the conditions that the patient seeks treatment for. In an example, the patient profile is populated with conditions associated with the patient automatically upon receiving and/or interpreting the results of diagnostic tests relevant to the patient. In an example, the results of the diagnostic tests 100 relevant to the patient are collected in accordance with other mechanisms of the system, optionally the calendar date that the results of the diagnostic tests 100 were collected. In various embodiments, information is input into the patient profile by the patient in association with input output mechanisms and/or operating system mechanisms associated with the computer device associated with the system as well understood by those skilled in the art.

In the preferred embodiment, an application, optionally the Patient-Facing Application, features an element to allow a patient to engage a ePHI exporter to export information relevant to that patient only. It is an aspect of the invention that the ePHI exporter can deliver the patient's electronic personal health information (ePHI) to a destination associated with a healthcare professional of the patient's choosing. In an example, the ePHI exporter when activated via the graphical user interface of an application, optionally the Patient-Facing Application, packages any information relevant to a patient into an interoperable format, such as HL7, a clinical document architecture, a continuity of care document or continuity of care record, structured product labeling, clinical context object workgroup, a format relevant to the fast healthcare interoperability resources, a format relevant to the services aware interoperability framework, Arden syntax, formats associated with the Trusted Exchange Framework and Common Agreement and/or other similar interoperable format to allow the interoperable export of information relevant to that patient's profile. In an example, the patient profile provides an element to allow the patient to provide consent to release the relevant patient user's ePHI to one specific healthcare professional or a plurality of specified healthcare professionals.

In the preferred embodiment, an application, optionally the Patient-Facing Application, is further configured to record and store the indicated result for the presence or absence of PdG at a pre-defined threshold and optionally the presence or absence of one or more additional hormones or hormone analytes at a pre-defined threshold of each diagnostic test 100 performed on a fluid sample of the patient. In various embodiments, it is a teaching of an embodiment for the system to instruct the patient user to conduct multiple diagnostic tests 100 each taken once every day for a number of consecutive days, optionally in association with the display of one or more interpretation(s) 607. In various embodiments, optionally in association with the above teachings, it is beneficial for the application to associated and record the calendar date that the diagnostic test, optionally consisting of a lateral flow assay, was performed, and store the results of the diagnostic test in association with the calendar date.

Figure 5:
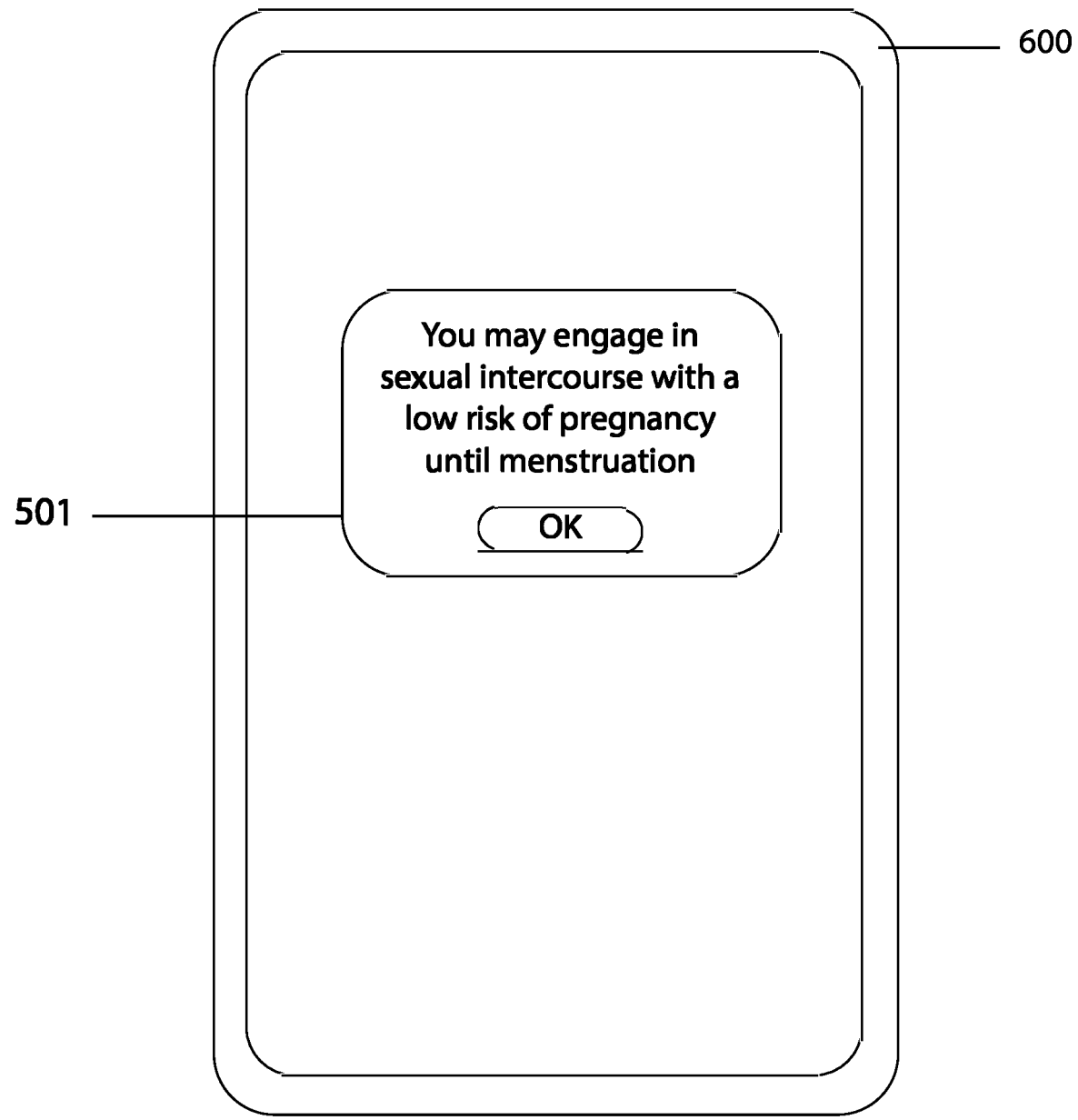
FIG. 5 depicts an exemplary smartphone and an exemplary unique message.

The application, optionally the Patient-Facing Application, is optionally configured to display any of a variety of a limited subset of unique messages 501, an example of which is depicted by FIG. 5, each corresponding to an interpretation 607 of results indicated on a diagnostic test 100 captured in the application, optionally the Patient-Facing Application, following the generation of the interpretation 607 of the results in association with the computing device, processor, camera and/or other components as described elsewhere herein. The present inventor has recognized the unique advantages of the diagnostic test(s) 100 as described herein, particularly when utilized in association with the Patient-Facing Application, associated with the ability for the collection of results on multiple consecutive days, optionally during an extended time period, to assist with detecting changes, which may comprise increases, decreases, or trends, of levels of hormones and/or analytes over time. Such detected changes, particularly when the diagnostic test 100 is utilized in combination with a physical or digital (for example, when coded into the Patient-Facing Application) form of the Diagnostic Test Key 200 and/or Color Intensity Key 800, may include information related to the extent of the change, such as a 1.5-fold change or 2-fold change, optionally indicated and/or calculated in association with the color intensity displayed on the diagnostic test 100 following use. The present inventor has recognized that the specific messages generated, optionally corresponding to the interpretations 607 described herein, correspond to a subset of the specifically available and uniquely valuable interpretations 607 associated with each diagnostic test 100. In particular, due to the binary nature of at least a subset of the the results generated by embodiments of the diagnostic test 100 comprising result indication lines, two of which are specifically configured to provide an indication for at least the presence or absence of LH at a threshold and the presence or absence of PdG at a threshold, respectively, in an applied fluid, the specifically available interpretations may be limited in an example to a subset comprising the below interpretations, or for each a similar unique message 501 with the same effect. In association with the Patient-Facing Application, each diagnostic test 100 in the preferred embodiment may be configured to evaluate for the presence or absence of any of FSH, an estrogen metabolite (such as E3G), LH, PdG, or hCG, or any combination thereof, as described elsewhere herein. Each unique message 501 optionally derives from and depicts one or more of the following specific interpretations, optionally by utilizing the processor, display, graphical user interface, Patient-Facing Application and/or other component of the system as described herein, of each diagnostic test 100 or series of diagnostic test results collected daily over a plurality of consecutive days within a menstrual cycle. In the preferred embodiment of the invention, due to the limited applications, and more specifically due to unique combination of diagnostic tests configured primarily to provide a binary result related to either the presence or absence at a threshold of one or more of the hormones or hormone metabolites selected from the group consisting of LH, PdG and hCG and also configured to provide a semi-quantitative, quantitative or trend-based result (i.e. of a fold change) related to of one or more of the hormones or hormone metabolites selected from the group consisting of FSH and an estrogen metabolite (such as E3G), a specific subset of useful indications relevant to a woman's fertility status and/or menstrual cycle, and also specifically useful to embodiments of the invention described herein, may be derived. Relatedly, the present inventor has determined that in association with embodiments of the invention that it is advantageous to interpret and depict the results in association with the specific phase of the menstrual cycle. The present inventor has recognized that no set value of estrogen or progesterone, the levels of which in a subject are optionally evaluated in association with the teachings of the invention herein, is needed to support a health cycle generally, but rather the desired values of estrogen of progesterone depend on the phase of the cycle in which the subject woman is in. Therefore, mapping her cycle in association with the teachings of the invention herein (and optionally the application, smartphone, graphical user interface, camera, display and/or communicatively connected storage medium as described herein) and the changes in estrogen, LH, and progesterone across the different phases of the cycle, optionally as determined in association with a diagnostic test 100 or plurality of diagnostic tests 100 as described elsewhere herein, is essential in understanding imbalances that cause disease of unwanted symptoms. Monitoring menstrual cycle hormones in association with the interpretations generated in association with teachings of the systems and methods as described herein are especially important during particular life stages encountered by a woman, for example, puberty, achieving or preventing pregnancy, and perimenopause. In various embodiments, the interpretations are generated via the application's (optionally the Patent-Facing Application's) interpretation of one or a plurality of diagnostic tests 100 and/or determination of associated results. Such subset of interpretations, optionally comprising an indication or instruction each of which may be displayed as a unique message 501 in association with components of the invention further described elsewhere herein, and the trigger for display of such unique message 501, comprises:

Following a result of a 1.5-fold decrease in FSH within a single menstrual cycle, the interpretation comprising an indication that a follicle has been selected, or alternatively a result on a diagnostic test of FSH levels of 3 mIU/ml-9 mIU/ml after a result on a previously taken different diagnostic test of FSH levels of 7 mIU/ml-12 mIU/ml generating an indication that a follicle has been selected;

Following a result of a 1.5-fold decrease in FSH within a single menstrual cycle, the interpretation comprising an indication of the fertile window opening and the appropriate time to engage in intercourse for conception, or alternatively a result on a diagnostic test of FSH levels of 3 mIU/ml-9 mIU/ml after a result on a previously taken different diagnostic test of FSH levels of 7 mIU/ml-12 mIU/ml generating an indication of the fertile window opening and the appropriate time to engage in intercourse for conception;

Following a result of a 1.5-fold decrease in FSH within a single menstrual cycle or a result on a diagnostic test of FSH levels of 3 mIU/ml-9 mIU/ml after a result on a previously taken different diagnostic test of FSH levels of 7 mIU/ml-12 mIU/ml, or on the eighth day of the menstrual cycle (as the present inventor has determined that this is a suitable backup period to appropriately effectuate the continuance of the steps of the method if a FSH drop is not indicated), whichever occurs first, the interpretation comprising an indication that it is the appropriate time to commence testing for an estrogen metabolite such as E3G and an instruction to commence testing for an estrogen metabolite such as E3G;

Following a result of a 1.5-fold decrease in FSH within a single menstrual cycle or alternatively a result on a diagnostic test of FSH levels of 3 mIU/ml-9 mIU/ml after a result on a previously taken different diagnostic test of FSH levels of 7 mIU/ml-12 mIU/ml, the interpretation comprising an indication that it is the appropriate time to discontinue testing for FSH and to commence testing for estrogen and an instruction to discontinue testing for FSH and to commence testing for estrogen;

Following a result of a persistently high level of FSH or following a result on one or more diagnostic tests of a FSH level greater than 25 mIU/ml, the interpretation comprising an indication of the likelihood of that ovulation may not occur this cycle or a high risk of anovulation;

Following a result of a persistently high level of FSH or following a result on one or more diagnostic tests of a FSH level greater than 25 mIU/ml, the interpretation comprising an indication of the likelihood of onset of menopause;

Following a result of a 1.5 fold increase in an estrogen metabolite or a result on a diagnostic test of 75-250 nmol/L of an estrogen metabolite following a result on a different diagnostic test generating an indication of 15-50 nmol/L of an estrogen metabolite, the estrogen metabolite optionally E3G, within a single menstrual cycle, an interpretation comprising an indication that a follicle has matured;

Following a result of a 1.5 fold increase in an estrogen metabolite or a result on a diagnostic test of 75-250 nmol/L of an estrogen metabolite following a result on a different diagnostic test generating an indication of 15-50 nmol/L of an estrogen metabolite, the estrogen metabolite optionally E3G, within a single menstrual cycle, an interpretation comprising an indication of the fertile window opening;

Following a result of a 1.5 fold increase in an estrogen metabolite or a result on a diagnostic test of 75-250 nmol/L of an estrogen metabolite following a result on a different diagnostic test generating an indication of 15-50 nmol/L of an estrogen metabolite, the estrogen metabolite optionally E3G, within a single menstrual cycle, an interpretation comprising an indication of the follicle secreting estrogen;

Following a result of a 1.5 fold increase in an estrogen metabolite or a result on a diagnostic test of 75-250 nmol/L of an estrogen metabolite following a result on a different diagnostic test generating an indication of 15-50 nmol/L of an estrogen metabolite, the estrogen metabolite optionally E3G, within a single menstrual cycle, an interpretation comprising an indication that it is the appropriate time to commence testing for LH and an instruction to commence testing for LH;

Following a result of a 1.5 fold increase in an estrogen metabolite or a result on a diagnostic test of 75-250 nmol/L of an estrogen metabolite following a result on a different diagnostic test generating an indication of 15-50 nmol/L of an estrogen metabolite, the estrogen metabolite optionally E3G, an interpretation comprising an indication that it is the start of the fertile window and the appropriate time to engage in intercourse for conception;

Following a result of a persistently low level of an estrogen metabolite or a result on a diagnostic test of less than 75 nmol/L of an estrogen metabolite, the estrogen metabolite optionally E3G, an indication that the subject woman will not ovulate during the menstrual cycle;

Following a result of a persistently low level of an estrogen metabolite or a result on a diagnostic test of less than 75 nmol/L of an estrogen metabolite, the estrogen metabolite optionally E3G, an indication that the subject woman is likely not fertile during the menstrual cycle;

Following a result of the presence of LH at a threshold, an interpretation comprising an indication that ovulation is imminent;

Following a result of the presence of LH at a threshold, an interpretation comprising an indication of elevated fertility or peak fertility;

Following a result of the presence of LH at a threshold, an interpretation comprising an indication that the subject woman should engage in sexual intercourse to conceive;

Following a result of the presence of LH at a threshold, an interpretation comprising an indication that the it is the appropriate time to commence testing for PdG and an instruction to commence testing for PdG;

Following a result of the presence of LH at a threshold, an interpretation comprising an indication that the it is the appropriate time to commence testing for progesterone and an instruction to commence testing for progesterone;

Following a result of a persistently low level of LH, an interpretation comprising an indication that ovulation may not occur during this menstrual cycle;

Following a result of a persistently low level of LH, an interpretation comprising an indication of the likelihood that ovulation is insufficient in this menstrual cycle for the subject woman to conceive;

Following a result of the presence of PdG at a threshold on the days inclusive of 7-10 days past ovulation, an interpretation comprising an indication that the subject woman has sufficiently ovulated to conceive;

Following a result of the presence of PdG at a threshold, an interpretation comprising an indication that the infertile period has begun;

Following a result of the presence of PdG at a threshold, an interpretation comprising an indication that the subject woman may engage in sexual intercourse with a low risk of conceiving or pregnancy until the onset of menstruation in the subsequent menstrual cycle;

Following at least one result of the absence of PdG at a threshold on one of the days selected from the range inclusive of 7-10 days past ovulation, an interpretation the woman has not sufficiently ovulated;

Following a result of the presence of hCG at a threshold, an interpretation comprising an indication of pregnancy;

Following a result of the absence of hCG at a threshold, an interpretation comprising an indication that the subject woman is not pregnant; and Following a result of the presence of hCG at a threshold and a result of the absence of PdG at a threshold, an interpretation comprising an indication that the subject woman has likely not produced enough progesterone to sustain pregnancy.

While the present inventor has specifically recognized the unique value of the above interpretations related to each diagnostic test 100 as described elsewhere herein, it is intended for the invention to optionally comprise additional interpretations, indications, instructions, prompts and unique messages 501 to more fully provide usefulness to the user of the embodiments described herein. Also, as referred to herein, any fold increase (i.e. 1.5 fold increase) or fold decrease (i.e. 1.5 fold decrease) as referred to herein in the context of the invention is considered to be at least that fold increase or fold decrease. For example, if a 3 fold increase for a hormone or analyte is indicated by a series of diagnostic tests, such indication also demonstrates a 1.5 fold increase. Also for example, if a 2 fold decrease is indicated for a hormone or analyte by a series of diagnostic tests, such indication also demonstrates a 1.5 fold decrease.

In various embodiments, an application, optionally the Patient-Facing Application, generates a unique message 501, chosen from a series of unique messages optionally consisting of the message depicted in FIG. 5 or optionally another message, for display to the patient user via the graphical user interface, display, and/or other mediums of communication, such as e-mail, SMS, automated phone call or push notification via a smartphone graphical user interface as illustrated by FIG. 5. In various embodiments, the unique message 501 may comprise an alert to change the diagnostic test 100 to test for a different hormone and/or analyte. In an embodiment, the unique message 501 may prompt a user to record the date of onset of menstruation. In an embodiment, the unique message 501 may prompt a user to record a baseline test to facilitate comparison by subsequently performed diagnostic tests in the same cycle. In an embodiment, the unique message 501 may prompt a user to apply a sample of the user's urine to a diagnostic test 100.

An application, optionally the Patient-Facing Application, in various embodiments is configured to aggregate the results of a plurality of diagnostic tests 100, each of which is performed daily by the patient user over a number of consecutive days for aggregation into a series to associate the results from each diagnostic test 100 taken daily during the period of the number of consecutive days with the patient user, optionally for transfer to a healthcare professional user via an ePHI importer/exporter. In the preferred embodiment, the diagnostic test 100 is performed by the patient user by applying first morning urine to the sample pad 191 (in an embodiment comprising the fluid application zone 106) of the diagnostic test 100. In one embodiment, the patient user performs the diagnostic test 100 on consecutive days during the period of 7-10 days past ovulation and utilizes the application to record the results of each diagnostic test 100, optionally in association with a communicatively connected storage medium as described elsewhere herein, and optionally in accordance with the teachings described in U.S. patent application Ser. No. 16/732,766 filed on Jan. 2, 2020 and U.S. patent application Ser. No. 17/308,149 filed on May 5, 2021, each of which is hereby incorporated by reference in its entirety with priority claimed thereto. In another embodiment, the system comprises a unique message 501 comprising instructions to the patient user to perform the diagnostic test 100 on consecutive days during the period of the patient user's single menstrual cycle and utilizes the Patient-Facing Application, in association with at least the camera, processor and computing device, to record the results of each diagnostic test 100. In various embodiments, it is a teaching of the system to utilize the data collected over multiple series to identify trends associated with the levels of PdG, and optionally additionally any of LH, an estrogen metabolite such as E3G, FSH, hCG and/or other tested hormone or hormonal analyte detected above or below a pre-defined threshold, or otherwise interpreted in association with a fold change as described elsewhere herein, associated with each diagnostic test 100.

In an embodiment, the application generates a unique message 501 to a user to prompt the user to initiate and utilize the application to evaluate a new diagnostic test 100 by utilizing an application, optionally the Patient-Facing Application, on a daily basis. In the preferred embodiment, the relevant unique message 501 is generated in the morning to remind the user to utilize first morning urine in association with the diagnostic test 100, as opposed to a urine sample taken later in the day. The present inventor has recognized that in an example, LH tests can be performed up to 3 times per day due to short time period associated with a LH surge, in which case it is a teaching of an embodiment of the invention to incorporate enough diagnostic tests 100 to evaluate thrice daily, and to actually perform in association with steps referring to testing a fluid for LH, testing at times corresponding to first morning urine, mid-day, and in the evening. The present inventor recognizes that this is particularly useful in association with examples of the invention, as some studies show that a more precise measurement of LH in association with the diagnostic test 100 configured to measure LH at a threshold is performed in the evening, as LH is higher in the evening in some women.

In various embodiments, the storage may exist on the mobile computing device itself or via a communicatively connected storage device, such as, for example, cloud connected storage. The application is configured to present a graph of the results over a time series on the display of the smartphone 600 or other computing device.

The an application, optionally the Patient-Facing Application, in an embodiment is configured to utilize the results detected by one or more diagnostic tests 100, optionally within a series of diagnostic tests performed daily during the time period correlating to a menstrual cycle, to detect a trend or trends of hormonal concentrations from one menstrual cycle to at least one other menstrual cycle or a plurality of other menstrual cycles. The trends are thereby interpreted by the application, and optionally delivered to a healthcare provider via a Healthcare Professional-Facing Application and/or the telemedicine system each described elsewhere herein, to generate suggested treatment protocols. In an example, a suggested treatment protocol comprises progesterone supplementation following the persistent absence of PdG as indicated on a series diagnostic tests 100 as further described elsewhere herein. In another example, a suggested treatment protocol comprises the consumption of a specified amount of pumpkin and flax seeds, optionally incorporated within a single consumable food item, optionally in snack bar form, commencing upon the first day of menstrual bleeding in a menstrual cycle. In another example, a suggested treatment protocol comprises the consumption of a specified amount of sesame and sunflower seeds, optionally incorporated within a single consumable food item, optionally in snack bar form, following the indication of the presence of LH at a threshold as indicated on a diagnostic test 100, as further described elsewhere herein. It is therefore a teaching of the method embodiment to perform the step of utilizing the results detected by one or more diagnostic tests to detect a trend or trends of hormonal concentrations from one menstrual cycle to at least one other menstrual cycle 8080. It is therefore a further teaching of the method embodiment to perform the step of interpreting the trends to generate suggested treatment protocol 8081, in association with the application and optionally by accessing clinical decision support systems via API as described elsewhere herein. In a method embodiment, it is a teaching of an embodiment to perform the step of suggesting a treatment 8082 optionally in the form of a suggested treatment protocol, and optionally in accordance with the teachings of the seed consumption system related to the consumption of certain seeds as described elsewhere herein or the ingesting, supplementation or injection of progesterone, optionally delivered via a display 605 or the graphical user interface of the application. It is a further teaching of the method embodiment to perform the step of delivering the suggested treatment protocol to a healthcare provider 8083. In a method embodiment, the suggested treatment protocol generated relates to the consumption of certain seeds as described elsewhere herein. It is a further teaching of the method embodiment to perform the step of supplementing progesterone following the identified trend of the persistent absence of PdG at a threshold over a time period as indicated by a series of diagnostic tests performed on a fluid of a subject woman 8085. Following the step of identifying of a trend persistent absence of PdG by either the application pre-configured to identify and detect such a trend associated with a subject woman, or by a healthcare provider identifying and detecting such a trend associated with a subject woman optionally in association with a telemedicine consultation as described elsewhere herein, which is a teaching of a method embodiment of the invention, it is a further teaching of a method embodiment to perform the steps of purchasing a progesterone supplement or plurality of progesterone supplement doses and delivering the progesterone supplement or plurality of progesterone supplement doses to the subject woman 8084. In various embodiments, clinical decision support systems or artificial intelligence technologies are utilized to generate treatment suggestions based on the detected trends of hormonal concentrations. In a method embodiment, it is a further teaching of an embodiment to perform the step of delivering the suggested treatment to one or more healthcare professional user(s), optionally (a) healthcare professional user(s) that a patient user has initiated an appointment with via the Scheduler 8086. In various embodiments, and in part due to the recurring nature of the menstrual cycle and the associated necessary testing, the steps described above are either repeated or performed in a variety of different orders. The present inventor recognizes the need to change the subset of steps or order in which the steps are performed or repeat steps or a subset of steps in certain examples, as the results of hormonal levels associated with the menstrual cycle may overlap at various and unexpected points in the menstrual cycle.

In a method embodiment, the application, optionally the Patient-Facing Application, utilizes the detected hormonal levels or trends of hormonal levels as collected by a series of diagnostic tests to generate suggestions of diet changes applicable to the patient user. In an embodiment, the suggested treatment protocol, optionally associated with the "suggesting" step described in the preceding paragraph, consists of generated suggestions of diet changes. For example, the ingestion of certain seeds, or food products incorporating portions of the certain seeds, due to their chemical compound composition, is well known to affect the hormone levels of a person who ingests such seeds or food products incorporating portions of the certain seeds, and it is useful to correlate the timing and/or quantity of consumption of such seeds or food products incorporating portions of the certain seeds to the results of one or more diagnostic tests 100 as described herein. In an embodiment, optionally in association with the "suggesting" step described above, the application is configured to generate suggestions for the consumption of certain seeds or food products incorporating portions of the certain seeds at specified times to affect hormonal concentrations of the patient user. In a method embodiment of the invention, it is a further teaching to perform the step of prompting the purchase of one or more products containing the suggested amount of seeds or food products incorporating portions of the certain seeds to ingest. In an example, the prompting takes place in the form of a subscription. In an example, the photographed diagnostic test 100 is shown within the graphical user interface of the application following the generation of a suggestion for the consumption of certain seeds or food products incorporating portions of the certain seeds at specified times. In an embodiment, the application is configured to facilitate the purchase by the patient user of the one or more products containing the suggested amount of certain seeds or food products incorporating portions of the certain seeds to ingest at a time for delivery to the patient user prior to the suggested specified time. The application-triggered delivery to the home or other desired location by the patient user is orchestrated in an example via FedEx, UPS, Amazon or other logistical and delivery service as well understood by those skilled in the art. In association with various embodiments described herein, the term "certain seeds" refers to pumpkin seeds optionally in the amount of 1 tablespoon and flax seeds optionally in the amount of 1 tablespoon (optionally intended for once daily consumption), optionally consumed once daily upon the start of menstruation in accordance with the teachings of an embodiment, and sesame seeds optionally in the amount of 1 tablespoon and sunflower seeds optionally in the amount of 1 tablespoon, optionally consumed following the first indication of a positive LH result on a diagnostic test 100 performed on the subject woman's urine in association with the teachings of an embodiment, or food products incorporating portions of pumpkin, flax, sesame, and/or sunflower seeds, or optionally otherwise in accordance with or by otherwise utilizing the Seed Consumption System as described elsewhere herein.

Figure 7:
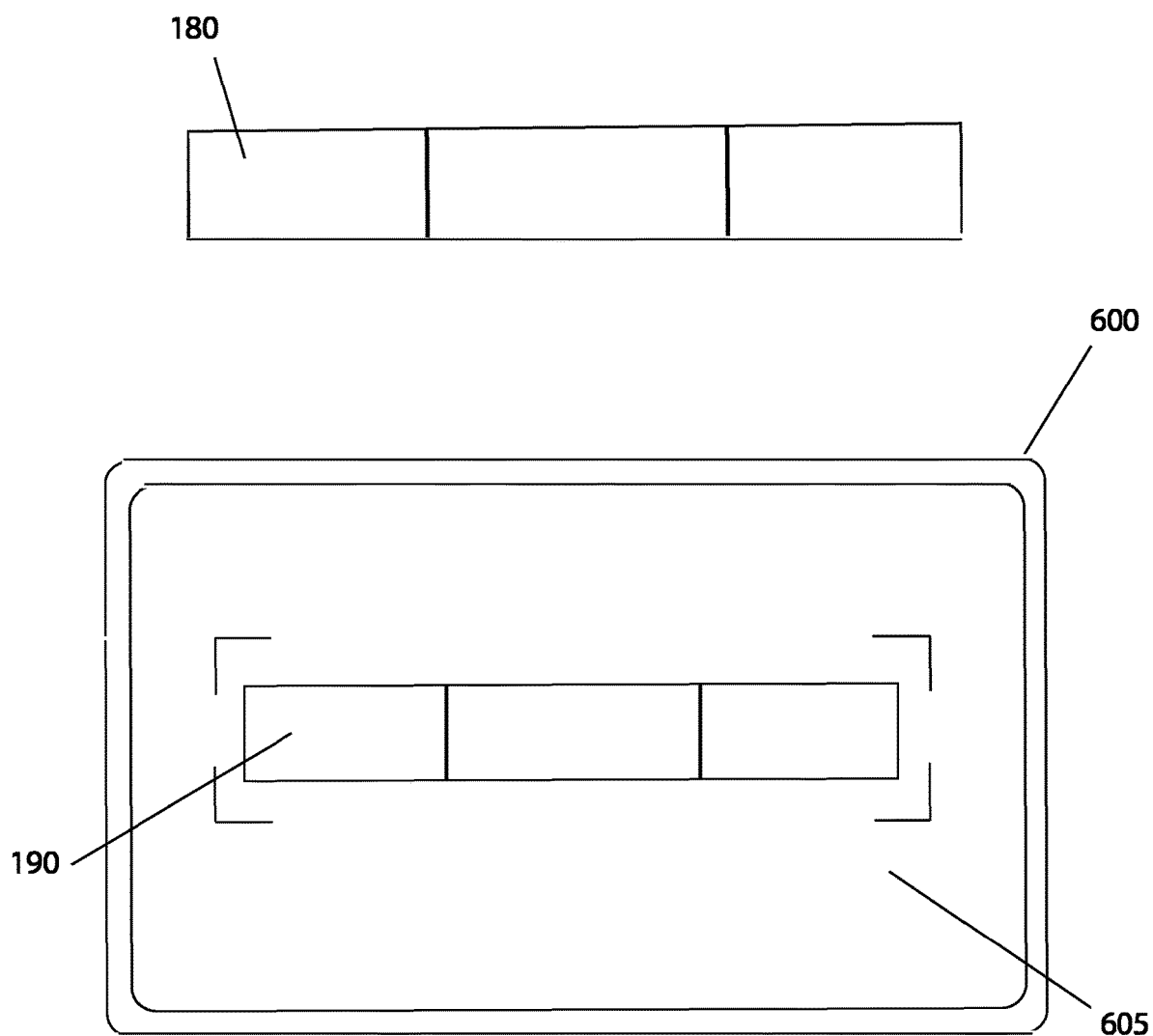
FIG. 7 depicts an example of aspects of the system as used together to photographically capture a diagnostic test.
Figure 8:
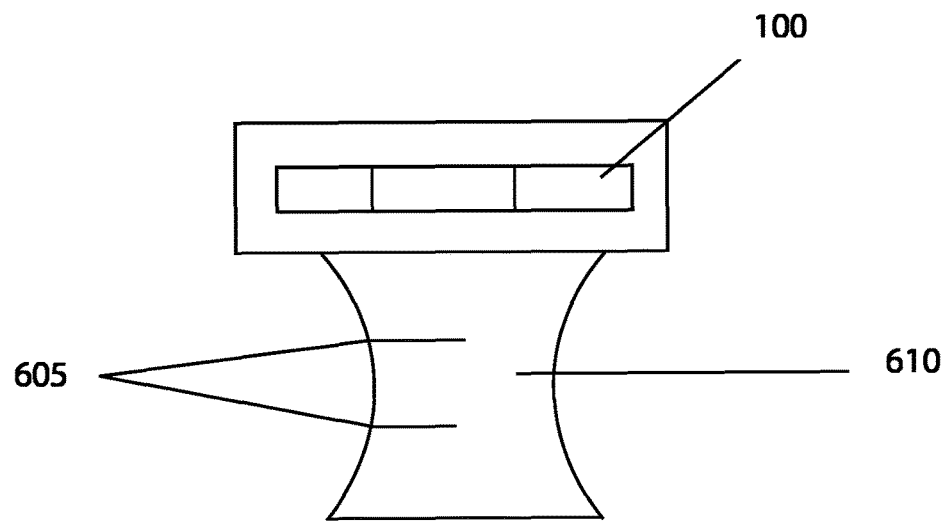
FIG. 8 depicts an example of aspects of the system as used together to photographically capture a diagnostic test in association with a stand featuring markings of a known distance apart intended to aid in the calculation of the dimensions of the diagnostic test.
Figure 8:
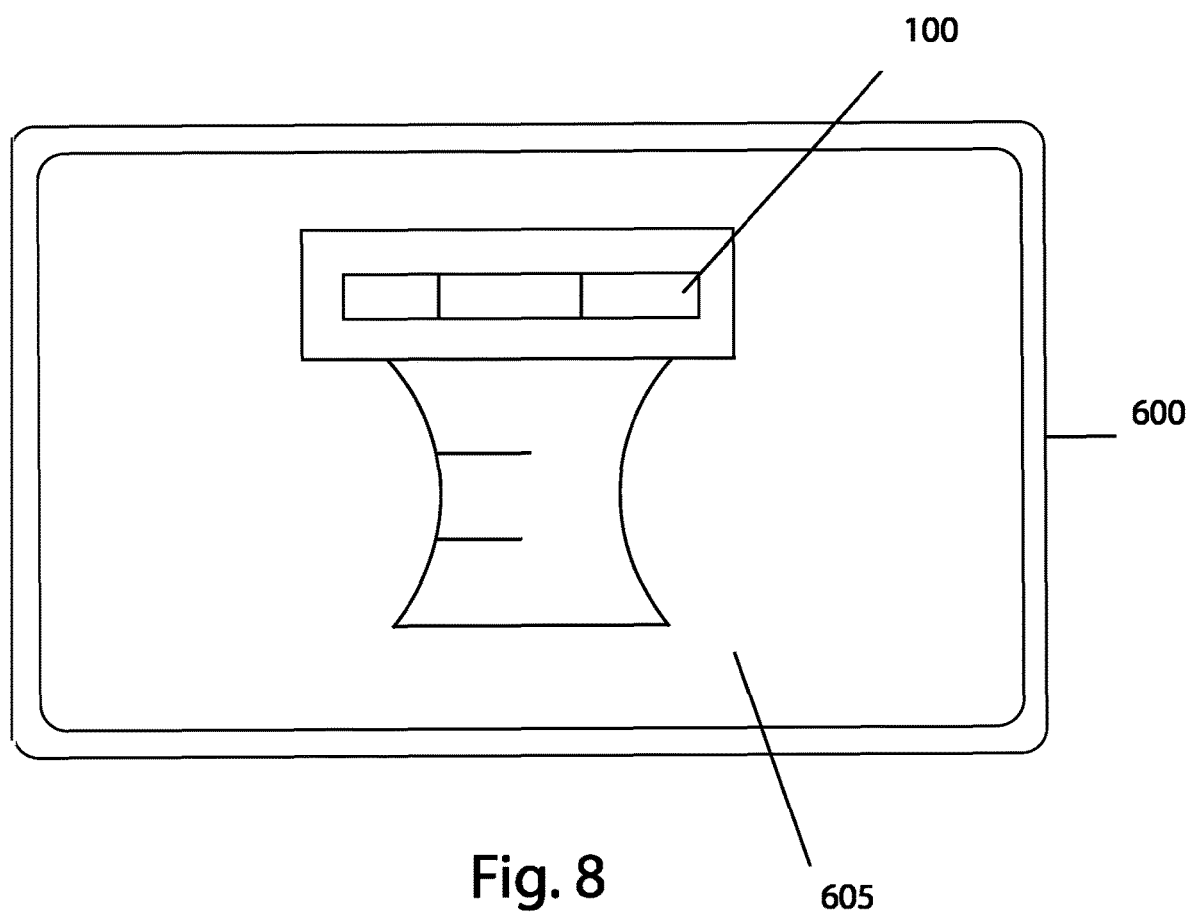

In an embodiment, the application further comprises a diagnostic test capture tool, illustrated by FIG. 7. The diagnostic test capture tool is configured utilize the display of a smartphone 600 to facilitate the alignment of the diagnostic test 100 within a smartphone 600 display for photographing and interpreting the results of a detected diagnostic test 100. In various embodiments, diagnostic test 100 comprises a lateral flow assay comprising at least a testing zone configured to detect for the presence or absence of PdG at a threshold, the threshold optionally selected from the range inclusive of 1 µg/mL-10 µg/mL, as further described elsewhere herein. In embodiments, the diagnostic test 100 comprises multiple testing zones, each configured to evaluate for the presence or absence of a single hormone or analyte, wherein one testing zone is configured to evaluate for the presence or absence of PdG at a threshold selected from the range inclusive of 1 µg/mL-10 µg/mL, as further described elsewhere herein.

Figure 28:
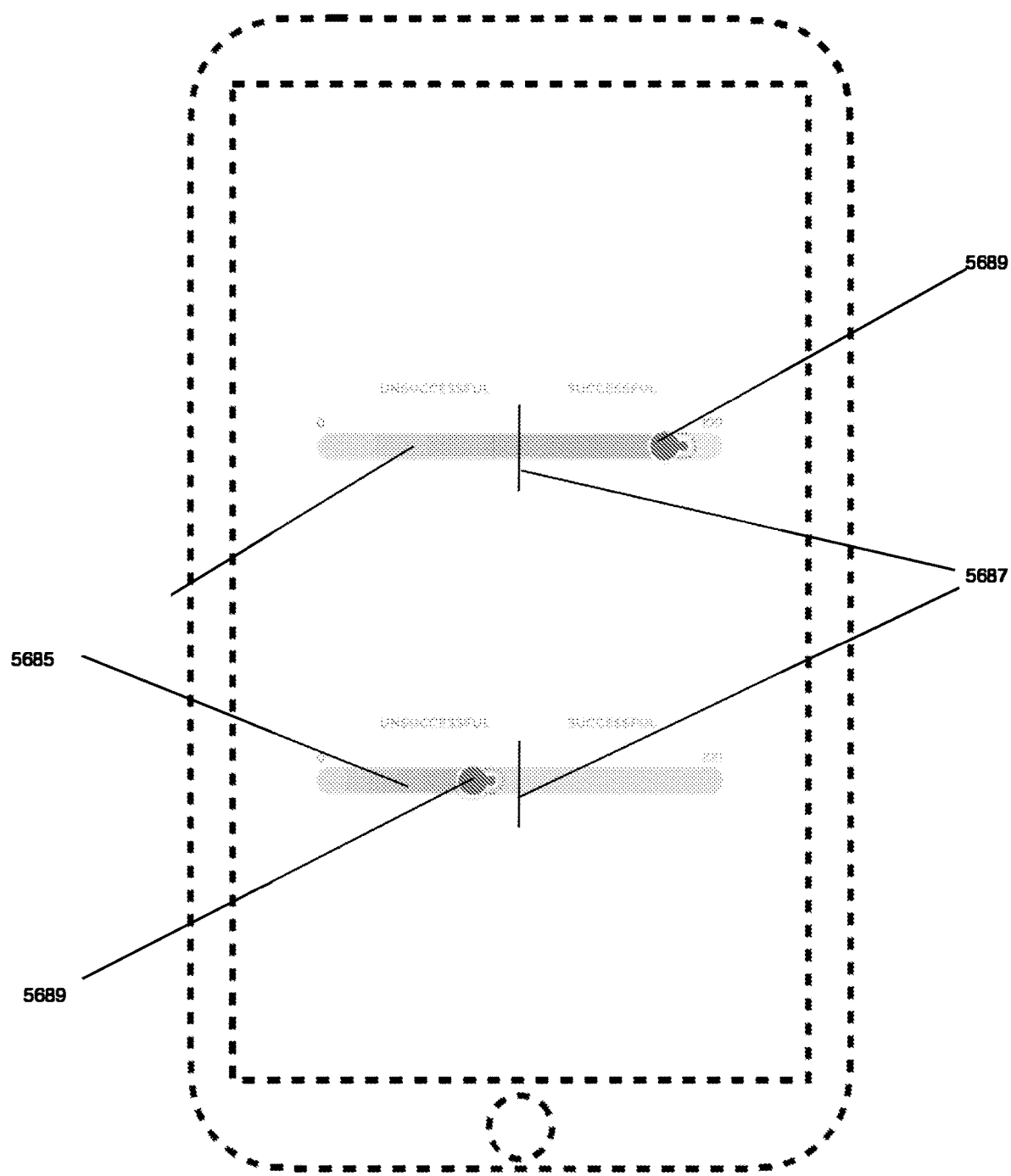
FIG. 28 depicts an exemplary user interface in association used with an embodiment of the system.

In an embodiment, the diagnostic test capture tool further comprises a stand 610 configured to hold a diagnostic test 100 in position during capture of a photograph in association with the Camera and the display 605 of the smartphone 600. In an embodiment, the stand 610 comprises markings 615 of a specified distance apart to aid in the calculation of the dimensions of the diagnostic test 100 held by the stand 610. In an embodiment, the interpretation of results of the diagnostic test 100 held by the stand 610 occurs in accordance with the teachings elsewhere herein associated with the specific sequence of result indication lines each corresponding to a specific testing zone each configured to evaluate for the presence of a specific hormone and/or analyte. In an embodiment, the interpretation of results of the diagnostic test 100 held by the stand 610 occurs in accordance with the teachings elsewhere herein associated with the specific distance of each result indication line from one end of a diagnostic test 100, optionally calculated by a Processor detecting the markings 615 on a stand 610 photographed by the smartphone 600 and comparing the pre-determined distance between the markings 615 to the diagnostic test 100 held by the stand 610 to assist with the determination of the specific dimensions of the diagnostic test 100, optionally by counting the specific number of pixels contained in a straight line between the markings 615 and then allocating the pre-determined distance between the markings to that number of specific pixels to allocate a specific width to a pixel, and subsequently counting the number of pixels and allocating the specific width to each pixels to determine a result for the distance between the photographed edge of a diagnostic test and one or more of the first testing zone, second testing zone, third testing zone, fourth testing zone, first result indication line 107, second result indication line 108, third result indication line 109, and fourth result indication line 110, to determine the location of each testing zone and/or result indication line and interpret the indicated result for the presence (or optionally the presence or absence at a threshold) of a specified hormone or analyte associated with each testing zone and corresponding result indication line. In an example, the application works in association with the diagnostic test 100 capture tool to facilitate the capture of the diagnostic test 100 and the interpretation of results. Such results may then be utilized by the camera, display, processor and other components of the system to provide information to the graphical user interface related to the results, the results optionally an indication of whether ovulation was successful or unsuccessful as depicted by FIG. 28 in an example, and optionally including treatment strategies and/or suggested treatment protocols, optionally comprising diet changes, optionally in accordance with the teachings and methods described elsewhere herein.

Figure 9:
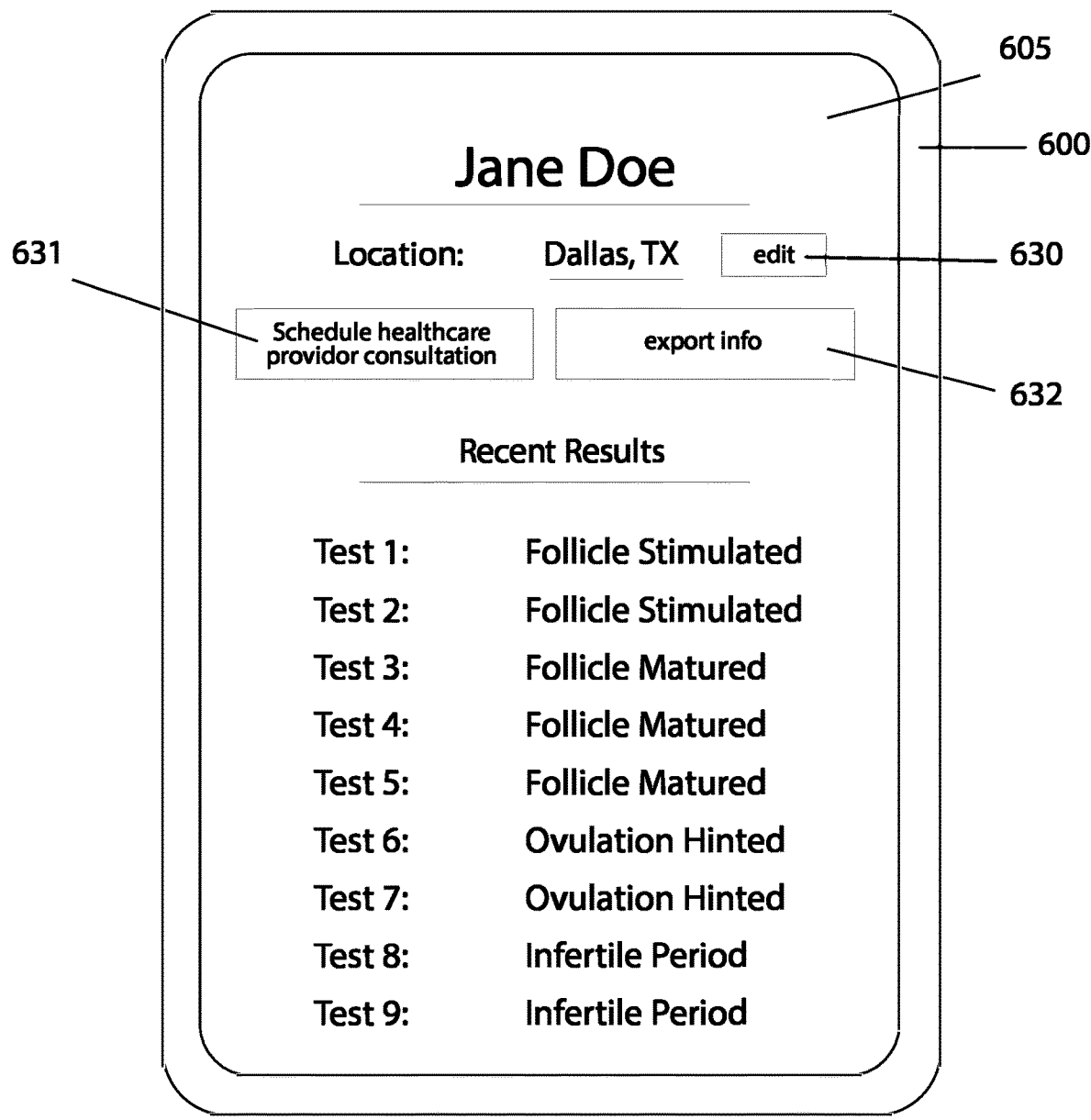
FIG. 9 depicts an exemplary graphical user interface of the application specifically configured at least to display a list of one or more diagnostic test results, set a location, and schedule a telemedicine consultation.

In various embodiments, the application incorporates a telemedicine system as described elsewhere herein, and is thus configured to allow a patient user to access available appointment times of healthcare professionals capable of treating medical conditions that may be suggested by the results of a diagnostic test or series of diagnostic tests captured and interpreted via the application. The application in an example incorporates a graphical user element configured to allow the patient user to set the patient's jurisdiction of residence 630, optionally within a graphical user interface as illustrated in FIG. 9 in an example. In an embodiment, the application is configured to facilitate the operation of the Telemedicine System within its graphical user interface, for instance via a graphical user interface element configured to allow a patient user to schedule a healthcare provider consultation 631, and optionally via a separate graphical user interface element configured to export information derived from the patient's collected diagnostic test results 632 as depicted on FIG. 9, which may include the packaging and delivery of results of one or more diagnostic tests 100 collected via the application in association with other components of the system and/or other electronic personal health information to one healthcare professional or a plurality of healthcare professionals in an interoperable format in accordance with the teachings elsewhere herein. In an example, the application is further configured to receive and distribute results from a sexual partner, optionally the results of a sexual partner's sperm test or plurality of sperm tests, and optionally in association with information triggered for export by the patient user as described herein, for further interpretation by a healthcare professional.

In various embodiments, the application, optionally the Patient-Facing Application, incorporates the Seed Consumption System as described elsewhere herein, and is correspondingly configured to provide suggestions of the consumption of certain seeds or food products incorporating portions of the certain seeds based on the interpreted results of a diagnostic test or series of diagnostic tests captured and interpreted via the Patient-Facing Application. In an embodiment, the application is configured to facilitate the operation of the Seed Consumption System described elsewhere herein within its graphical user interface. In various embodiments, the application is configured to provide suggestions, optionally in the form of suggested treatment protocols, for the consumption and/or supplementation of progesterone of a specific amount, optionally in droplet format and optionally in association with the triggering of a purchase and delivery of progesterone or a product containing progesterone, optionally purchase and delivery the "Proov Balancing Oil" containing progesterone, MCT oil, Vitamin E and lemon oil, in response to a detected indication for the absence of pregnanediol glucuronide generated in association with a diagnostic test as described elsewhere herein to provide progesterone supplementation. In various embodiments, such suggestions are delivered to a patient user each as a unique message 501 as illustrated by FIG. 5 for example. As such, it is a step in a method embodiment engage in suggesting supplementation of progesterone, and optionally triggering the purchase of a progesterone supplement or plurality of progesterone supplement doses, in response to a detected indication for the absence of pregnanediol glucuronide on a diagnostic test. In an embodiment, the supplementation of progesterone occurs in coordination with a progesterone supplement system.

An embodiment of the invention comprises a progesterone supplement system. The progesterone supplement system comprises a plurality of diagnostic tests configured to detect for the presence or absence of LH at a threshold as defined herein, and a plurality of diagnostic tests configured to detect for the presence or absence of PdG at a threshold as defined elsewhere herein. The progesterone supplement system further comprises a plurality of progesterone supplement doses. In the preferred embodiment, each progesterone supplement dose contains a quantity of progesterone selected from the range of 25-35 mg. In the preferred embodiment, each dose is formulated in an oil suspension. An exemplary oil for use in association with the oil suspension is coconut oil or MCT oil. In the preferred embodiment, the oil comprises mixed tocopherols (vitamin E). The present inventor has recognized that by formulating the progesterone with vitamin E in the form of a progesterone supplement dose, the vitamin E acts as a carrier to deliver the progesterone directly into the blood stream and quickly. In one example, the steps of formulating each progesterone supplement dose include adding 5-10% weight by volume of Vitamin E (also referred to as "mixed tocopherols") with 90-95% weight by volume on MCT oil or coconut oil. Subsequently, perform the step of dissolving the bio-identical progesterone (natural progesterone), such that the final concentration of progesterone should be 7-15 grams per 100 ml. Optionally, perform the step of heating the mixture of the preceding sentence at 60-70 C for 5-20 minutes to increase solubility.

The present inventor by testing various steps has likewise determined a preferred method of progesterone supplementation in association with the progesterone supplement doses. In various embodiments, the progesterone supplement doses are provided in association with the "Proov Harmonizing Oil" offered by applicant MFB Fertility, Inc. and comprising progesterone, MCT oil, Vitamin E, and lemon oil. In the preferred method, a user engages in the step of testing, on a daily basis, for the presence or absence of LH in a bodily fluid at a threshold via a diagnostic test as defined elsewhere herein 3450. Following the first result, indicating the presence of LH at a threshold in the tested bodily fluid, optionally commencing at a time 2 days after the first result indicating the presence of LH at threshold in the tested bodily fluid, the user (optionally by instruction generated in association with the Patient-Facing Application, a digital device 670 or other display 605 following the first result indicating the presence of LH at a threshold) engages in applying a progesterone supplement dose containing 10-40 mg of progesterone formulated in an oil suspension, optionally applied to the membranes of the mouth, optionally applied up to three times per day for a period of at least 7 days or the period until the start of the next menstrual cycle, whichever is longer 3451. In other embodiments, the progesterone formulated in an oil suspension is applied to a thin skin of the body in accordance with the teachings of the invention, such thin skin of the body including but not limited to the lips, breasts and underarm areas. The present inventor has determined the enhanced effectiveness of this form of progesterone supplementation, particularly in comparison to other forms of over-the-counter progesterone supplementation, in that progesterone applied in this manner is better absorbed into the blood stream. It is a teaching of embodiments of the invention that the application may comprise an instruction delivered via the graphical user interface for the subject tested with a diagnostic test to consume the progesterone supplement during the subsequent menstrual cycle following an indication of the absence of PdG at a threshold in the applied fluid on any date following a positive result on a diagnostic test configured to evaluate for the presence or absence of LH in the subject's same menstrual cycle. The present inventor has recognized the benefit of progesterone supplementation during a menstrual cycle to aid in healthy ovulation or to support a pregnancy where progesterone levels are deficient. The related method may further comprise steps of testing, during the period of 7-10 days past ovulation, for the presence or absence of PdG in the bodily fluid with a diagnostic test comprising a testing zone and corresponding result indication line configured to detect for PdG at a threshold selected from the range of 1 μg/mL-10 μg/mL 3452; and Applying a quantity of 75-105 mg of progesterone formulated in an oil suspension to the membranes 193 of the mouth on a daily basis during the subsequent menstrual cycle if any of the diagnostic tests comprising a testing zone and corresponding result indication line configured to detect for PdG and provide a result indicating the absence of PdG on any of the days during the period of 7-10 days past ovulation (optionally by instruction generated in association with the Patient-Facing Application, a digital device 670 or other display 605 following a result indicating the absence of PdG at a threshold in an applied fluid during the timeframe of 7-10 days past ovulation of the subject woman) 3453.

Figure 10:
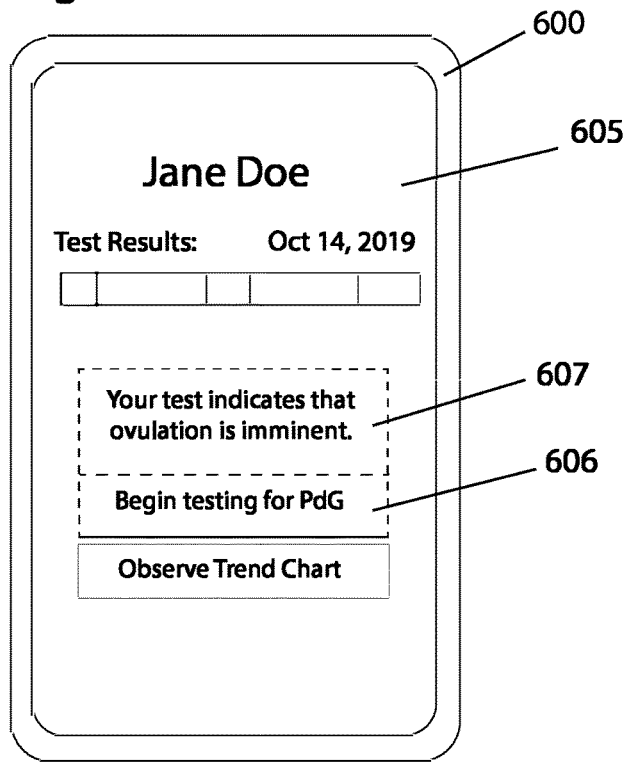
FIG. 10a depicts a configurations of a user interface configured display unique messages pertinent to a diagnostic test associated with the system in an embodiment.
FIG. 10b depicts a digital reader to interpret and display unique messages pertinent to a diagnostic test associated with the system in an embodiment.
FIG. 10c depicts an apparatus associated configured to hold a diagnostic test associated with the system in an embodiment.
FIG. 10d depicts a cartridge configured to enclose a diagnostic test associated with the system in an embodiment.
Figure 10:
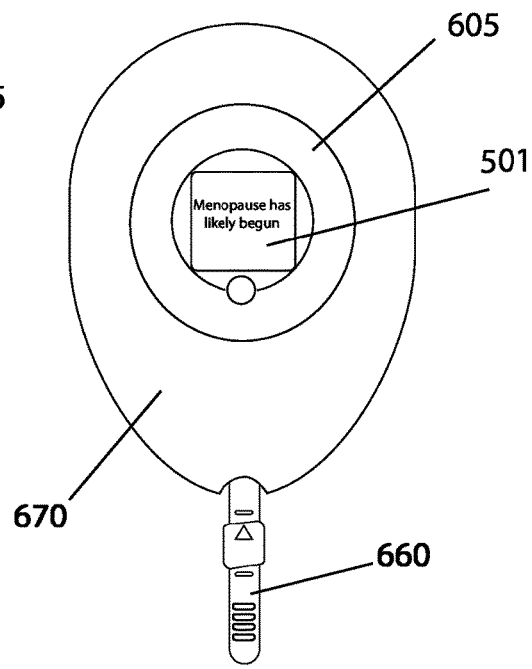
Figure 10:
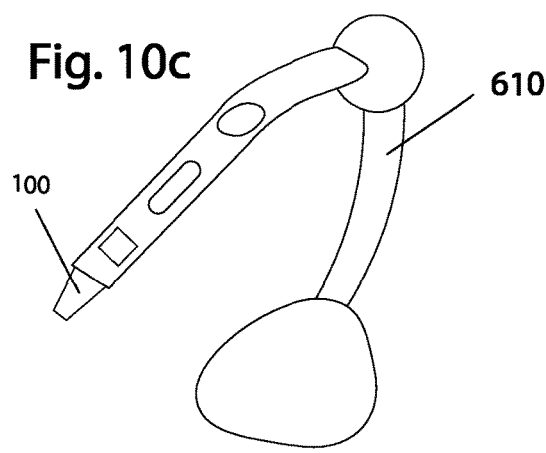
Figure 10:
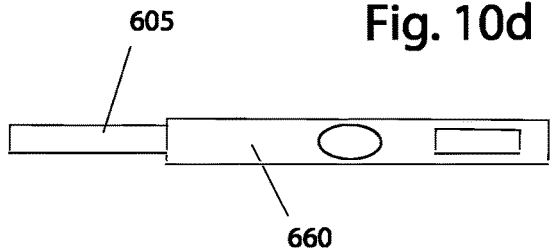

In various embodiments, an interpretation 607 deriving from the result of a diagnostic test 100 as described elsewhere herein, optionally comprising an interpretation 607 collected in association with the Fertility Tracking System and/or methods of use of the Fertility Tracking System as described elsewhere herein, optionally collected in association with an application operating in association with a mobile device, is displayed to the user via the display 605, optionally the display 605 associated with the an application operating in association with a smartphone 600. An example of such an interpretation 607 is depicted in FIG. 10*a*. In various embodiments, a prompt 606 or plurality of prompts in association with the Fertility Tracking System and/or methods of use of the Fertility Tracking System as described elsewhere herein is delivered to a patient user via the graphical user interface of the an application operating in association with a mobile device, optionally each as a unique message 501. An example of such a prompt 606 depicted in association with a diagnostic test result and interpretation 607 is depicted in FIG. 10*a*. In various embodiments, a prompt 606 or other aspects of the an application operating in association with a mobile device are configured for delivery to a display 605 integrated within a cartridge containing a lateral flow assay 660 as illustrated by FIG. 10*d*, or the display 605 of a digital reader 670 configured to evaluate a lateral flow assay by placement of a cartridge containing a lateral flow assay 660 therein as illustrated by FIG. 10*b*, optionally in association with the other electronic components of the cartridge containing a lateral flow assay 660 and/or the digital reader 670.

Computing Device

In varying embodiments of the invention, a computing device is useful in capturing, processing and storing the results indicated by one or more diagnostic test(s), along with the demographic information of a specified subject woman and associated suggested treatment protocols, configured as described elsewhere herein.

In the preferred embodiment, the computing device consists of a smartphone 600. In various embodiments, the term "smartphone" is defined as a mobile phone that performs many of the functions of a personal computer, typically having a touchscreen interface, internet access, and an operating system capable of running downloaded applications. A smartphone 600 may be defined more broadly as a mobile telecommunications device. In various embodiments, the smartphone 600 consists of either an Apple iPhone or Google Android device. In various embodiments the smartphone 600 is configured to operate a version of the iOS or Android operating systems. In one embodiment, the computing device is operated in association with an application, optionally the Patient-Facing Application, further configured to incorporate mechanisms to control, collect data from or otherwise interact with the computing device. In an alternative embodiment, the computing device consists of a personal computer.

In an alternative embodiment, the computing device comprises a server or communicatively other connected computer accessed via the internet via a smartphone 600 or local personal computer. In such embodiment, the application operating in association with a mobile device may be operated by a patient user, optionally consisting of a subject woman whose bodily fluid has been applied to at least one diagnostic test 100 as referred to elsewhere herein, or a healthcare professional user as applicable via a web browser in accordance with mechanisms and methods well understood by those skilled in the art.

In an exemplary embodiment, the computing device consists of the system described in U.S. patent application Ser. No. 16/302,085 filed on May 19, 2017, incorporated by reference herein. In another exemplary embodiment, the computing device consists of the system described in PCT Patent Application PCT/US2019/038173 filed on Jun. 20, 2019, incorporated by reference herein.

In the preferred embodiment, the computing device incorporates and/or controls storage, at least one processor and at least one camera. In various embodiments, the application operating in association with a mobile device is configured to operate upon the operating system of the computing device in accordance with mechanisms and procedures well understood by those skilled in the art. In various embodiments, the computing device comprises a cloud system configured to communicatively connect with a smartphone 600 for interpretation and analysis of the data collected from a diagnostic test 100 in association with a photograph of the diagnostic test 100 taken and interpreted by the smartphone 600 as more comprehensively described elsewhere herein.

In association with various embodiments of the invention, it is useful to provide a camera configured to collect the results of the diagnostic test. This is especially the case when recording an image of a diagnostic test via a computing device operated by a layperson in association with the systems and methods as described elsewhere herein. In an embodiment, the camera consists of a camera integrated into a smartphone 600 as is well understood in the art. In alternative embodiments, the camera is incorporated into a cartridge also housing a diagnostic test 100, or in a digital reader 670 configured to receive and interpret a diagnostic test 100 placed within the digital reader 670.

In the preferred embodiment, the camera of the system is incorporated within a smartphone 600 or tablet computer operating an application. In an embodiment, the system comprises a smartphone 600, mobile telecommunications device, or tablet computer featuring both a rear-facing or front-facing camera. It is recognized by the inventor that any camera of a smartphone 600 configured with multiple cameras may be utilized in association with the system as described herein.

In the preferred embodiment, the camera associated with the system is utilized to photograph the lateral flow assay, the processor associated with the system is utilized to interpret the color within each of a plurality of result indication lines on the lateral flow assay, the processor associated with the system is configured to interpret the intensity of the color within each of a plurality of result indication lines on the lateral flow assay to determine a result, the result is associated with the date the camera photographed the lateral flow assay, the result is stored in the communicatively connected storage medium, and optionally displayed in a calendar format via a graphical user interface. In accordance with such teaching, it is a further teaching of a method embodiment to perform the step of determining a result 2019. In an example, the determining a result step is performed by photographing, via a camera integrated within a smartphone 600, the diagnostic test 1000, optionally comprising a lateral flow assay test. In an example, the Patient Facing Application is pre-configured to identify, optionally by identifying the shape of the diagnostic test 100 depicted in a photograph captured by the camera, and measuring the distance from one end or both ends of the diagnostic test 100, and in association with the Processor and distances that the an application operating in association with a mobile device is pre-configured to associate with one or more result indication line(s) each configured to evaluate for the presence or absence of a distinct hormone or analyte at a threshold. The collection of a photograph in an optimal fashion is optionally by utilization of an alignment mechanism displayed within the display of a smartphone 600 as depicted in FIG. 7 in an example to allow a user of the application to align the test in a useful manner to aid in the determination of the distance to and identification of each result indication line on the lateral flow assay to be photographed. In one example, the user is prompted to align one end of the diagnostic test 100 with an element in the graphical user interface to facilitate the identification and measurement of the diagnostic test 100.

It is therefore a teaching of a method embodiment to perform the step of orienting the photograph of the lateral flow assay test to determine the locations of the one or more result indication lines of the lateral flow assay test 2020. It is also a further teaching of a method embodiment to perform the step of identifying the specific color intensity (optionally by RGB or HEX color code), optionally with the assistance of the color intensity key 800, associated within the color detected by the camera within a result indication line of the lateral flow assay test 2021. It is a further teaching to perform the step of comparing the color intensity associated with the color detected by the camera within the result indication line of the diagnostic test 100 with a pre-defined threshold intensity signifying the presence or absence of the hormone or hormonal analyte 2022 associated with the result indication line in the applied fluid. As further described in more detail elsewhere herein, the lateral flow assay test referred to in such step optionally consists of a single test configured to simultaneously or near-simultaneously detect for the presence or absence of a plurality of hormones or hormonal analytes selected from the group consisting of pregnanediol glucuronide, luteinizing hormone, an estrogen metabolite such as E3G, FSH, estradiol, progesterone and human chorionic gonadotropin 2023.

In an embodiment of the invention, the term "camera" refers more broadly to an optical sensor. An optical sensor of the disclosure can have several components, including 1) a raw camera sensor; 2) LED lights; 3) a microcontroller; 4) an aperture; 5) a shutter; and 6) a simple optical lens. For example, an optical sensor of the disclosure can have an optical system comprising of a fluid (e.g. poly(dimethylsiloxane) (PDMS)) or solid (e.g., glass) material lens and a complementary metal-oxide semiconductor (CMOS) or a charge-coupled device (CCD) image sensor. The optical sensor can also use an orientation element located on the lateral flow device to locate the one or more result indication lines and the control line. An optical sensor in an embodiment comprises a high-resolution camera configured to take an image of at least one result indication line and the control line of the diagnostic test 100. In an embodiment, the optical sensor is configured to detect a fluorescent label. In such configuration, the observable positive result provided on the membrane of a lateral flow assay is obtained in association with the optical reader of such diagnostic test system. In various embodiments, the optical reader may comprise the camera of a smart phone. In various embodiments of the invention, a base unit 4001 associated with a diagnostic test system as described herein comprises the optical reader. For example, the optical sensor can be a countertop device, a stand-alone device, the optical sensor module as described in PCT Patent Application PCT/US2019/038173 filed on Jun. 20, 2019, incorporated by reference herein, the "detection instrument" as described in U.S. patent application Ser. No. 16/302,085 filed on May 19, 2017, incorporated by reference herein, or a smartphone camera. In varying embodiments, the optical sensor may be contained within an apparatus intended for use apart from the diagnostic test 100, such as the digital reader 670 depicted in FIG. 10*b*. In another embodiment, the optical sensor is contained within an apparatus sharing a containment mechanism with the diagnostic test 100, such as a cartridge 660, as depicted in FIG. 10*d*.

In an example of the invention, the camera is configured to collect one or more optical signals each originating from a distinct result indication line of a diagnostic test 100, optionally in coordination with the processor. In one embodiment, the camera is configured to receive a plurality of optical signals each originating from one of a plurality of result indication lines in coordination with mechanisms to measure the length to and sequence of each result indication line and match the result indicated by each result indication line, optionally via a Diagnostic Test Key, as described elsewhere herein. In an embodiment, the camera is configured to work in conjunction with the processor and/or other elements of a system to determine an amount of at least a first analyte, optionally the presence or absence of the first analyte at a threshold, and a second analyte, optionally the presence or absence of the second analyte at a threshold, in a biological sample applied to the fluid application zone 106 based on said optical signals, wherein an optical signal associated with the first result indication line 107 increases with decreasing amounts of said first analyte present in said biological sample, and an optical signal associated with the second result indication line 108 increases with increasing amounts of said second analyte present in said biological sample. In an embodiment, the RGB or HEX color codes associated with specific quantities of a hormone or hormone analyte are determined prior to use of the diagnostic test 100, optionally by applying spiked male urine containing pre-measured quantities of a hormone or hormone analyte as described elsewhere herein, and the RGB or HEX color codes associated with each indication for each quantity are recorded, optionally in association with the color intensity key and/or the diagnostic test key 200. In association with various embodiments, in FIG. 6, the "R" values associated with the "RGB" color codes are depicted as an example. In association with computer application mechanisms well-known in the art (such as, for instance, the color matching tools associated with Adobe Photoshop and other graphic editing applications, or components thereof), the quantity of a hormone or hormone analyte (or the presence or absence of a hormone or hormone analyte) is determined by finding the closest RGB color code or HEX color code to the RGB color code or HEX color code pertaining to the color evident on a result indication line following the application of a fluid to a diagnostic test 100, and then estimating the quantity of the relevant hormone or hormone analyte or the presence or absence of a hormone or hormone analyte based upon the pre-measured quantity of the hormone or hormone analyte associated with said closest RGB color code or HEX color code, optionally as indicated on the color intensity key and/or diagnostic test key 200.

In an example, the camera may operate in coordination one or more light sources forming a part of the disclosure for illuminating the diagnostic test 100 or at least the first result indication line 107 of the diagnostic test 100 configured to detect for at least the presence or absence of pregnanediol glucuronide at a threshold selected from within the inclusive range of 1 µg/mL-10 µg/mL, or as further described in U.S. patent application Ser. No. 16/732,766 filed on Jan. 2, 2020 and U.S. patent application Ser. No. 17/308,149 filed on May 5, 2021, each of which is hereby incorporated by reference with claim of priority made thereto.

As used herein, the singular term "processor" or plural term "processors" generally refer to the electronic circuitry within a computing device that executes instructions that make up a computer program and/or application as well understood by those of skill in the art. In an example, the processor consists of a cloud computing mechanism operating in conjunction with a smartphone as is well understood by those skilled in the art. In an example, the processor consists of one or more processors of a smartphone 600 utilized in association with the system described herein.

Figure 6:
FIG. 6 depicts an exemplary color intensity key.
Figure 6:
Figure 6:
Figure 6:
Figure 6:
Figure 6:
Figure 6:
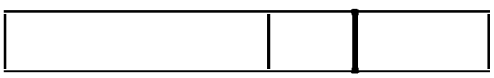
Figure 6:
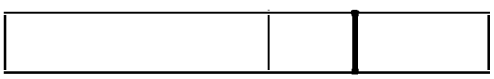

In association with the various systems and methods described herein, the diagnostic test 100 configured to evaluate urine for the presence or absence of at least pregnanediol glucuronide at a threshold selected from the inclusive range of 1 µg/mL-10 µg/mL comprises at least the first result indication line 107 configured such that, optionally when used with a base unit, a first optical signal (e.g., a fluorescent signal) is capable of being detected at the first result indication line 107. In various embodiments, the location of the first result indication line 107 and/or one or more other result indication lines is determined by a pre-defined sequence made available for use by the system, by a measurement of the diagnostic test 100 to determine the pre-programmed location of each result indication line as described elsewhere herein. The first optical signal may be a readout for the amount of pregnanediol glucuronide in the sample, for example, by detecting the amount of first detection reagent, in an example comprising the colloidal gold-labeled PdG antibody, bound to the first capture reagent, in an example comprising the PdG-BGG conjugate, by correlating the color intensity of the first optical signal developed to a pre-determined measurement of the level of pregnanediol glucuronide correlating to the color intensity. It is a teaching of an embodiment to determine the resulting color intensity(ies), and/or the resulting RGB color code(s) or HEX color code(s) associated with each evident color, of the first result indication line 107 collected from a plurality of diagnostic tests at a time selected from the range inclusive of 3-20 minutes following the application of samples each containing a distinct, fixed amount of pregnanediol glucuronide to create a color intensity key 800, optionally comprising a part of or useful in association with the Diagnostic Test Key 200, for uses in association with those described herein. In one example, the average or median color intensity and/or RGB or HEX color code is determined by sampling a plurality of pixels contained within one result indication line to collect the result, optionally for incorporation the Diagnostic Test Key 200 and/or the color intensity key 800 to associate a specific color intensity, RGB color code or HEX color code with a quantity of hormone or hormone analyte present in the diagnostic test 100. In one example, the average or median color intensity and/or RGB or HEX color code is collected for each of a plurality of tests, and then the average or median color intensity and/or RGB color code or HEX color code is then determined for the plurality of tests to determine a result, optionally for incorporation the Diagnostic Test Key 200 and/or the color intensity key 800 to associate a specific color intensity, RGB color code or HEX color code with a quantity of hormone or hormone analyte present in the diagnostic test 100. An exemplary color intensity key 800 is depicted by FIG. 6, though it is to be understood that in varying configurations a single color intensity key 800 may provide associations with multiple color intensity combinations, whereby each color intensity optionally associated with a specific sequence or location coordinate as determinable by calculating the distance of the indication from one end of a diagnostic test 100, correlating to multiple hormones and/or analytes. In an embodiment of the invention, the color intensity key 800 may assume the form of the positivity scale 5685 as described elsewhere herein. A similar protocol is likewise used for one or more result indication line(s) configured to evaluate alternative hormones and analytes. It is a teaching of an embodiment in the preferred embodiment to utilize only diagnostic tests 100 in association with the methods described herein that were manufactured according to standardized manufacturing protocols in a similar manner to those utilized to create the color intensity key 800. In accordance with the determination of the correlation of different levels of color intensity with a specific level of pregnanediol glucuronide, each of the plurality of diagnostic tests similarly configured to a diagnostic test 100 intended for subsequent real-world use is applied with a sample of male urine, each containing a specified quantity of precisely measured added amount of pregnanediol glucuronide. In various embodiments, each such sample may be referred to as a male urine sample spiked with pregnanediol glucuronide. The intensity of each such sample is measured and optionally re-measured, and the average color intensity displayed across all diagnostic tests for which a male urine sample spiked with a standardized amount of pregnanediol glucuronide is associated with the standardized amount of pregnanediol glucuronide in association with evaluation purposes. It is therefore a teaching of a method embodiment of the invention to create a color intensity key 800 by the steps of creating a sample of fluid containing a known amount of a hormone or analyte 8090, applying the sample of fluid to a diagnostic test 100 configured to evaluate for the presence of the hormone or analyte 8091, measuring the color intensity indicated following the application of fluid 8092, allocating the color intensity indicated to the known amount of the hormone or analyte 8093, and optionally aggregating the plurality of color intensity indications each allocated to a known amount of hormone or analyte into a color intensity key 8094. It is a teaching associated with an embodiment that the phrase "color intensity" as referred to herein may also refer to or correspond to a specific RGB color code or HEX color code. The present inventor has recognized the usefulness of the step of utilizing a plurality of color intensity keys each correlating to a specific hormone or analyte in a distinct result indication line in a specific diagnostic test 100 configuration. The color intensity key facilitates the ability to determine one or more results from a diagnostic test 100, as the color intensity key applied in conjunction with the predetermined distances of each result indication line and/or the sequence of the hormone and/or analyte tested within each result indication line, determinable on a photographed diagnostic test 100 in association with the teachings as described elsewhere herein, facilitates the identification of both the hormone and/or analyte tested and the amount of the hormone and/or analyte indicated within the relevant result indication line. In an embodiment, the sequence of hormones/and or analytes associated with each result indication line is made available for evaluation in association with the relevant color intensity key to determine the amount of hormone and/or analyte precisely associated with each result indication line of the diagnostic test 100. In an embodiment, the color intensity key 800, and the sequence of hormones/and or analytes or the distance of each result indication line and the associated hormone and/or analyte of each result indication line, are programmed into the application operating in association with a mobile device or a digital reader 670 to facilitate the detection of each color intensity indicated within a result indication line on the diagnostic test 100. The application operating in association with a mobile device in an example is also configured to interpret of the results of a diagnostic test 100 by selecting the closest matching color intensity on the color intensity key 800 for each detected indication within each of the result indication lines, and deriving the previously determined amount of hormone or analyte correlating to that closest matching color intensity as associated to the hormone or analyte associated with the relevant result indication line.

The color intensities associated with their correlated standardized amounts of pregnanediol glucuronide, optionally aggregated into a color intensity key 800, may be displayed on the Diagnostic Test Key for utilization in association with interpreting the diagnostic test 100 in an example. In an example, the color intensity key 800 is utilized in association with a processor configured to compare the color intensity of a photographed diagnostic test with the closest color intensity indicated on the color intensity key 800 correlated to a previously determined amount of pregnanediol glucuronide correlating to the closest color intensity as to provide an estimation of the amount of pregnanediol glucuronide. In an example, the processor is configured to evaluate a photographed diagnostic test 100 to which a fluid sample has been applied to compare the color intensity of the evident color within a result indication line of that diagnostic test 100 to the color intensity that the result indication line would exhibit at the threshold associated with that result indication line, to aid in determining a result for the presence or absence of the relevant hormone or hormone analyte at the threshold. It is a teaching of an embodiment to measure the color intensity of the relevant result indication line of a diagnostic test 100 configured to evaluate urine for the presence or absence of pregnanediol glucuronide following the application of a male urine sample spiked with pregnanediol glucuronide in a specific amount selected from the inclusive range of 1 µg/mL-10 µg/mL (also referred to as the "Threshold Concentration"), and set the measured color intensity as the Threshold Color Intensity for the interpretation of similarly manufactured diagnostic tests, and optionally indicate the threshold color intensity on a color intensity key 800 and/or a diagnostic test key 200 for subsequent testing purposes. The present inventor notes that the Threshold Concentration and Threshold Color Intensity is only relevant in various configurations to the result indication line configured to detect for the presence of pregnanediol glucuronide, and specifically not necessarily relevant to other result indication lines configured to detect for the presence of other hormones or hormone metabolites. In the preferred embodiment, a diagnostic test 100 is configured with a first result indication line 107 having a Threshold Color Intensity, wherein when the first result indication line 107 exhibits a color intensity less than the Threshold Color Intensity (for example, by the evident absence of a visually perceptible line), the associated interpreted indication is that of a positive result for pregnanediol glucuronide at the Threshold Concentration.

It is a teaching of the preferred embodiment of the invention to include a processor configured to operate in conjunction with the other elements of the system as described herein configured to evaluate a diagnostic test 100 to which a fluid sample has been applied to compare the color intensity of at least the first result indication line 107 with the Threshold Color Intensity, and then based on the comparison, determine a result for the presence or absence of pregnanediol glucuronide at the Threshold Concentration and then optionally display the result via a graphical user interface or as a unique message 501 as described elsewhere herein.

In various embodiments, the color intensity of one or more separately collected optical signals collected from the same diagnostic test 100 provides an indication or a plurality of indications for the presence or absence of one or more additional hormones and/or analytes. In such embodiments, the processor is configured in accord with the teachings herein to utilize the one or more separately collected optical signals to interpret an additional result or additional results indicated by the diagnostic test 100. In the preferred embodiment, the color intensity of the optical signal obtained from the first result indication line 107 configured to analyze for the presence or absence of pregnanediol glucuronide at a threshold increases in intensity when the amount of pregnanediol glucuronide present in the sample is lower, and such optical signal decreases in intensity when the amount of pregnanediol glucuronide present in the sample is higher. In an example, the optical signal obtained from within the first result indication line 107 configured to analyze for the presence or absence of pregnanediol glucuronide is inversely proportional to the amount of pregnanediol glucuronide in the fluid sample applied to the diagnostic test 100 containing the first result indication line 107. In various aspects, the diagnostic test 100 further comprises at least a second result indication line 108 configured to produce an optical signal likewise corresponding to the presence or absence of a second analyte or hormone at a threshold, optionally luteinizing hormone (LH), wherein the optical signal obtained from within the second result indication line 108 configured to analyze for the presence or absence of luteinizing hormone is directly proportional to the amount of luteinizing hormone in the fluid sample applied to the diagnostic test 100 containing the second result indication line 108. In various aspects of the systems and methods herein, the diagnostic test 100 is configured for utilization in conjunction with a base unit or digital reader 670 as described elsewhere herein and in various applications incorporated by reference herein, together comprising a system embodiment.

In one example, a system is provided comprising: a housing, comprising:
  a) a port for receiving an diagnostic test 100, the diagnostic test 100 comprising two or more result indication lines each corresponding to a testing zone of the conjugate pad 190, one result indication line of which is configured to provide an indication of the presence or absence of pregnanediol glucuronide at a threshold of a specific amount selected from the inclusive range of 1 µg/mL-10 µg/mL;
  b) a reader, comprising:
    i) one or more light sources for illuminating said two or more result indication lines;
    ii) one or more light detectors, optionally consisting of a camera or cameras as described elsewhere herein, configured to detect optical signals from each of the two or more result indication lines; and
  c) a data analyzer comprising one or more processors configured to receive the optical signals in association with other components of the system as described elsewhere herein and to determine for the presence or absence of pregnanediol glucuronide at the threshold of a specific amount selected from the inclusive range of 1 µg/mL-10 µg/mL and a second analyte or hormone present in a biological sample applied to the diagnostic test 100 based by evaluating the optical signals, wherein the optical signal obtained from within the result indication line configured to evaluate for the presence or absence of pregnanediol glucuronide decreases with increasing amounts of pregnanediol glucuronide present in a biological sample applied to the diagnostic test 100, and an optical signal obtained from within a second of said two or more result indication lines increases with increasing amounts of said second analyte present in the biological sample.

An exemplary system may include a housing for containing components as described elsewhere herein, optionally configured as illustrated in FIG. 10b. The housing can be constructed of any suitable material. The housing may be configured to receive a lateral flow assay configured to detect for at least the presence or absence of pregnanediol glucuronide as described elsewhere in the disclosure. The housing may include a port or opening for receiving a diagnostic test 100, optionally contained within a cartridge. The system may further include, optionally contained within the housing, a reader device. The reader device in an embodiment comprises the camera as described elsewhere herein and the processor configured to interpret the results of the diagnostic test 100 as described elsewhere herein. The reader device may include one or more light sources for illuminating the diagnostic test 100 or a first result indication line 107 configured to detect for at least the presence or absence of pregnanediol glucuronide. In one particular example, the one or more light sources are calibrated to generate a light wavelength suitable to illuminate a detectable label, optionally a fluorescent label or colloidal gold, providing an indication of whether pregnanediol glucuronide is present or absent at a threshold within the first result indication line 107. In a particular example, the detectable label provided on the immunoassay device is a fluorophore, and therefore, the one or more light sources of the reader device should include a fluorescent light source (e.g., a light-emitting diode (LED)). It is to be understood that the wavelength of light provided by the light source of the reader device should be selected based on the excitation wavelength of the detectable label, and can readily be selected by a person of skill in the art. In an embodiment, the reader may be configured to illuminate the both the first result indication line 107 configured to provide an indication for the presence or absence pregnanediol glucuronide in a sample applied to the diagnostic test 100, and a second result indication line 108, each at a wavelength of light calibrated to accurately obtain the optical signal from each label, optionally at separate wavelengths. In some cases, the reader is configured to scan across the diagnostic test 100, comprising a test strip of an immunoassay device. In such cases where the immunoassay device utilizes a single fluorophore, the reader may contain a single fluorescent light source. In cases where the immunoassay device utilizes more than one fluorophore, the reader may contain more than one fluorescent light source. In various embodiments, the processor is configured to interpret the optical signals obtained from within each result indication line and discern among the wavelengths to generate a result. In various embodiments, the interpretation is made with the assistance of the color intensity key 800, wherein the color intensity key 800 is pre-configured to indicate the presence of specified quantities of hormones and/or analytes following the application of fluorescent light from the fluorescent light source to the immunoassay device utilizing at least one fluorophore based upon the evident color intensity(ies).

The reader may further comprise one or more light detectors (e.g., a photodetector) for detecting optical signals from the diagnostic test 100. Generally speaking, the one or more light detectors should be capable of distinguishing between emitted light at a first discrete position and a second discrete position on the diagnostic test 100. This may be accomplished by, e.g., the one or more light sources scanning across the diagnostic test 100 and determining the position of the emitted light on the diagnostic test 100.

In an embodiment, it is a teaching of an embodiment to provide a data analyzer. The data analyzer may have one or more processors configured to receive an optical signal. In some cases, the data analyzer is in operable communication with a reader device, optionally as described in as described in PCT Patent Application PCT/US2019/038173 filed on Jun. 20, 2019, incorporated by reference herein, the "detection instrument" as described in U.S. patent application Ser. No. 16/302,085 filed on May 19, 2017, incorporated by reference herein. In various examples, the reader device is programmed to utilize the color intensity key 800 to interpret detected results. The data analyzer may be configured to determine an amount of analyte or hormone present in an applied fluid sample, for example, by measuring the intensity of an optical signal obtained from within a result indication line of a diagnostic test 100 configured to detect for the presence or absence of pregnanediol glucuronide, optionally in association with the color intensity key 800. For example, the data analyzer may be configured to calculate the area under the curve of a signal intensity plot. The data analyzer may further be configured to determine the differences between signal intensities among the multiple discrete result indication lines or regions on the diagnostic test 100, each optionally providing an optical signal deriving from a different wavelength of light. In an example, the data analyzer may be configured to determine the difference between the signal intensity at the first result indication line 107 of a diagnostic test 100 and the signal intensity at the second result indication line 108 to provide a result. In an example, each result is collected by evaluating the difference in intensity between the optical signal within a result indication line and the optical signal collected from another aspect of the diagnostic test 100 and determining whether the difference in color intensity exceeds a threshold. In an embodiment, to accomplish a teaching in the previous sentence, the difference of color intensity between the control line 105 and a result indication line of a separate diagnostic test of a similar configuration following the application of a male urine sample spiked with pregnanediol glucuronide at a threshold is measured to provide a threshold difference for subsequent use, optionally for use in association with a Diagnostic Test Key 200 and/or color intensity key 800. The threshold difference then previously obtained from the separate diagnostic test 100 of a similar configuration is compared by the data analyzer to determine any difference in a diagnostic test 100 to which a fluid sample is applied for testing, and if the difference in color intensity of the diagnostic test 100 to which a fluid sample is applied exceeds the threshold difference, then a positive result for pregnanediol glucuronide in the applied sample is determined by the data analyzer in the embodiment. In the case that the difference does not exceed the threshold difference in the embodiment, a negative result for pregnanediol glucuronide in the applied sample is determined by the data analyzer. In various embodiments, the data analyzer then generates and transmits the result to other components of the system, optionally including the display 605, by mechanisms as readily understood by those skilled in the art. The data analyzer may further be configured to calculate an amount or concentration of the analytes present in the sample by similar mechanisms.

In an embodiment, the data analyzer may be further configured to detect a binary optical pattern. The binary optical pattern can be generated by two fluorescent materials which excitation and/or emission spectrum differs in wavelength. In some cases, the binary optical pattern can be generated by one fluorescent material and one light absorbent material. The detection reagents may be conjugated with the two types of materials respectively and can be captured in the same result indication line, such that the result indication line may generate two different optical signal patterns in the data analyzer.

In various aspects, the system may comprise a housing 670 for containing the processor and/or other electronic components, such as those depicted in FIG. 10*b*. The encasement of FIG. 10*d* may also be characterized as a housing for purposes in accordance with the teachings herein. The housing, in an example consists of a top housing and a bottom housing. The top housing in an example comprises a display 605 for indicating the results of the diagnostic test 100, as depicted in FIG. 10*d*, providing an indication at least for the presence or absence of pregnanediol glucuronide, said indication obtained by mechanisms as described elsewhere herein. The system and/or its processor may further comprise a display cover. The system may further comprise a battery. The system and/or its processor in an embodiment comprises a circuit board containing electronic components.

The system and/or its processor in an embodiment further comprises an optomechanics module. The optomechanics module in an embodiment comprises the one or more light sources and one or more light detectors as described elsewhere herein. In varying embodiments, the optomechanics module comprises the optical sensor module as described in PCT Patent Application PCT/US2019/038173 filed on Jun. 20, 2019, incorporated by reference herein, or the "detection instrument" as described in U.S. patent application Ser. No. 16/302,085 filed on May 19, 2017, incorporated by reference herein. The optomechanics module is configured in an embodiment as comprising the one or more light sources for illuminating the diagnostic test 100 configured to detect for at least the presence or absence of progesterone or a progesterone analyte. The optomechanics module in an embodiment is movable across an optical axis such that the optomechanics module moves laterally across the diagnostic test 100 to detect for at least the presence or absence of pregnanediol glucuronide by enabling alignment with the relevant result indication line of the diagnostic test 100. The system may further comprise an actuation module. The actuation module may comprise one or more motors configured to actuate/move the optomechanics module. In some embodiments, the motors may be coupled to a rack and pinion mechanism that is configured to translate the optomechanics module along one or more directions. For example, the optomechanics module can be translated along a longitudinal axis of the diagnostic test 100. The direction(s) of translation may or may not be orthogonal to an optical axis of the optomechanics module. In varying embodiments, the optomechanics module comprises, contains or is communicatively linked to the camera as described elsewhere herein. The direction(s) of translation may be parallel to the longitudinal axis of the diagnostic test 100, and the optical axis may be orthogonal to the longitudinal axis or a planar surface of the diagnostic test 100. In some cases, the direction(s) of translation need not be parallel to the longitudinal axis of the diagnostic test 100, and the optical axis need not be orthogonal to the longitudinal axis (or a planar surface) of the diagnostic test 100. For example, the direction(s) of translation and/or the optical axis may be at an oblique angle relative to the longitudinal axis of the diagnostic test 100.

In various aspects, the system and/or its processor may include an optical configuration suitable for use with the diagnostic test 100 and positioning of the optics above a result indication line configured to detect for at least the presence or absence of pregnanediol glucuronide. The optical configuration may include a light source (e.g., a light-emitting diode (LED) for illuminating the diagnostic test 100. The optical configuration may further include one or more lens, a filter, a optical beamsplitters, or any combination thereof. The optical configuration may further include a photodetector for detecting an optical signal from the diagnostic test 100. In an example, the system is configured to an excitation/emission spectra with an excitation wavelength of 492 nm and an emission wavelength of 512 nm.

In an embodiment, the processor is configured to perform an evaluation on the diagnostic test 100 to obtain a result by comparing the color intensity indicated on the diagnostic test 100 to at least one color intensity associated with a color intensity key 800 to derive the closest color intensity and retrieve the associated hormone or analyte concentration. This may be accomplished, for example, by utilizing the camera to calculate and detect the distance of one or more result indication line(s) from the proximal end of the diagnostic test by matching the dimensions with pre-determined diagnostic test 100 proportions, and detecting the evident color intensity(ies) within the result indication line(s) contained in the diagnostic test 100 at specified locations by comparing the evident color intensity(ies) to the color intensity(ies) included within the color intensity key 800 and/or the Diagnostic Test Key 200.

For instance, the processor may be configured to detect the dimensions of the diagnostic test 100 via a camera in association with a preconfigured known height of the diagnostic test 100. In an example the processor is configured to extrapolate the measurements of the length of the diagnostic test 100 by normalizing the height of the diagnostic test 100 as photographed to a pre-determined height and performing the appropriate mathematical equations (for example, the Pythagorean equation) to determine the length of the diagnostic test 100, and in particular to determine the length distance from one end to one or more result indication line(s) located on the diagnostic test 100 and the length distance from the proximal end to the control line 105 located on the diagnostic test 100. In an example, the processor is configured to evaluate for to detect the color intensity evident within one or more result indication line(s) located at a predetermined distance or distances from the one end of the diagnostic test 100 in a predetermined sequence, and compare the color intensity evident within each result indication line(s) to the closest known color intensity with an associated known concentration corresponding to a quantity of the relevant hormone or hormonal analyte to determine the indicated result or results, the indicated result or results optionally indicating the presence or absence of one or more hormones and/or hormonal analytes at a threshold. The processor is then configured to store and display the indicated result or results in coordination with the other inventive elements as described herein.

In various embodiments, the processor is communicatively linked to the other components of the system to collect and transmit signals and/or the indicated result(s) to the other components as needed to enable functioning of the system as is well understood by those skilled in the art.

Various embodiments of the system as described herein comprise a display 605. In the preferred embodiment, the display 605 consists of the screen of a smartphone 600 or a tablet computer. In various embodiments, the display 605 consists of a screen incorporated within a cartridge, as depicted in FIG. 10*d*. In various embodiments, the display 605 consists of a screen incorporated within a digital reader 670 or base unit, as depicted in FIG. 10*b*. In embodiments of the invention, the display is configured to make visible a graphical user interface to a user. In various embodiments of the invention, the display is integrated with pressure-sensitive digitizers, such as the Apple Force Touch system. It will be widely understood to those skilled in the art that information displayed within and elements visible on the display 605 in certain embodiments may be manipulated or otherwise interacted with by a user via a variety of input output devices, optionally including a touchscreen, keyboard, keypad, mouse or other input output devices as well understood in the art. In various embodiments, the display 605 comprises the display as described in PCT Patent Application PCT/US2019/038173 filed on Jun. 20, 2019, incorporated by reference herein, or the display as described in U.S. patent application Ser. No. 16/302,085 filed on May 19, 2017, incorporated by reference herein. In an embodiment, the display is configured as a small screen placed within a housing or cartridge also containing a diagnostic test 100 such as that illustrated by FIG. 10*d*.

Figure 11:
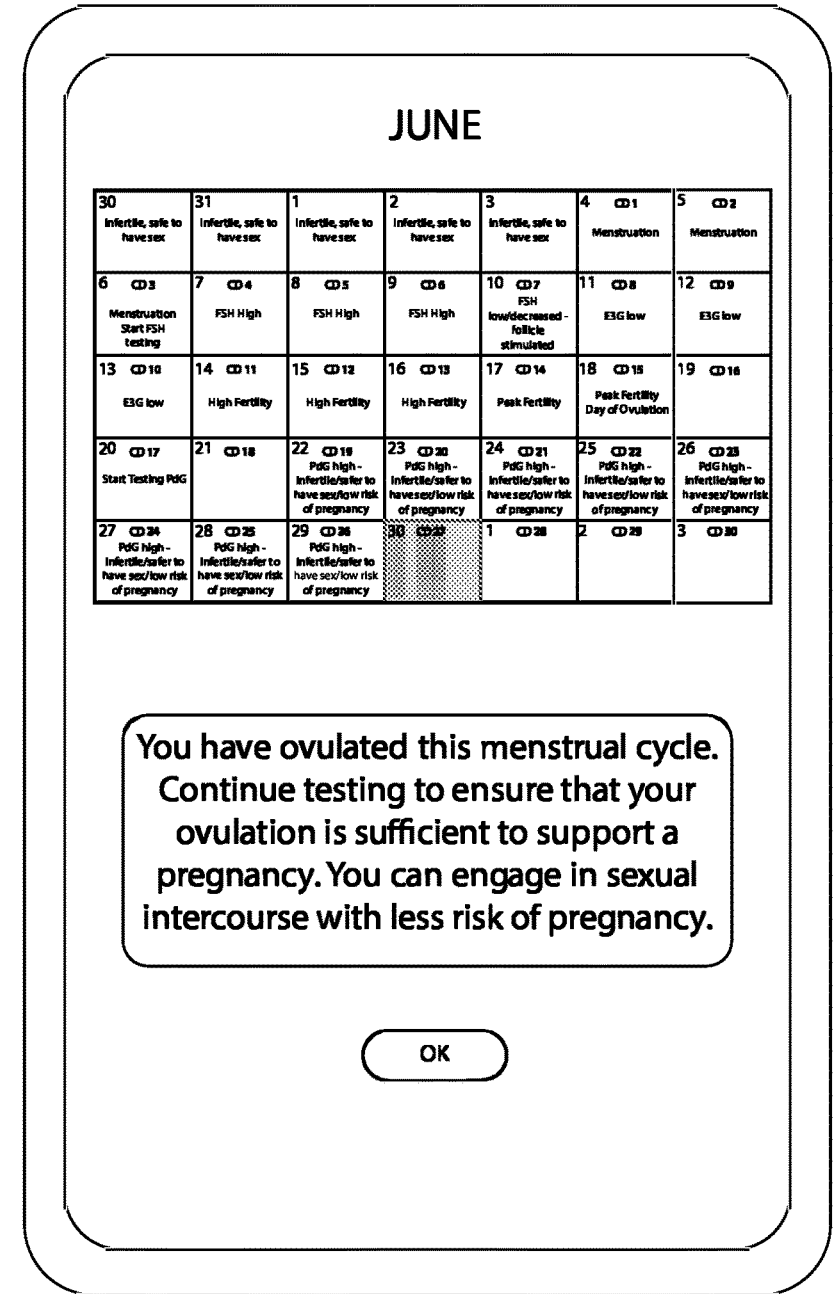
FIG. 11 depicts an exemplary graphical user interface comprising a calendar.
Figure 12:
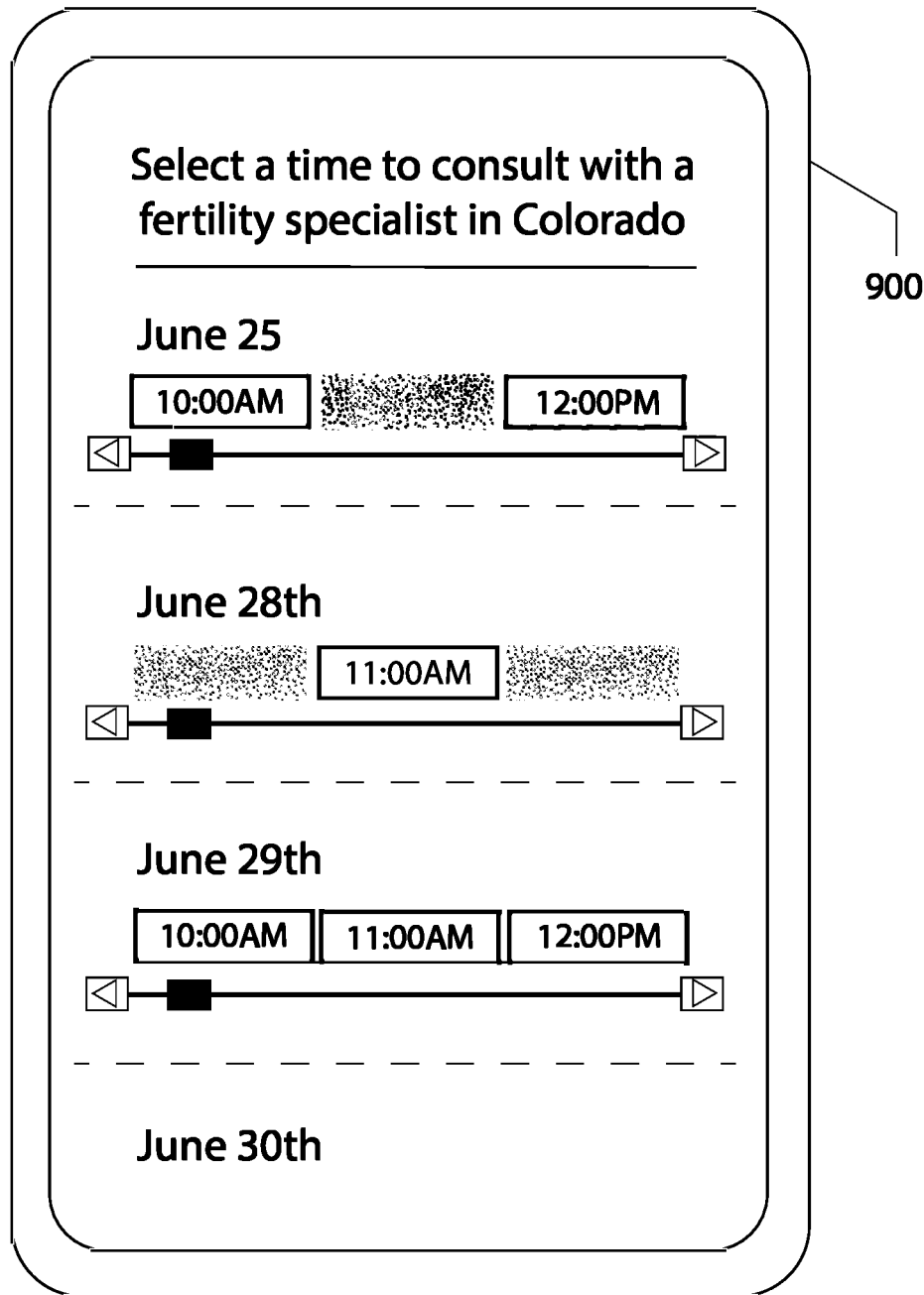
FIG. 12 depicts an exemplary graphical user interface associated with the Scheduler associated with a specifically detected location of the user.
Figure 13:
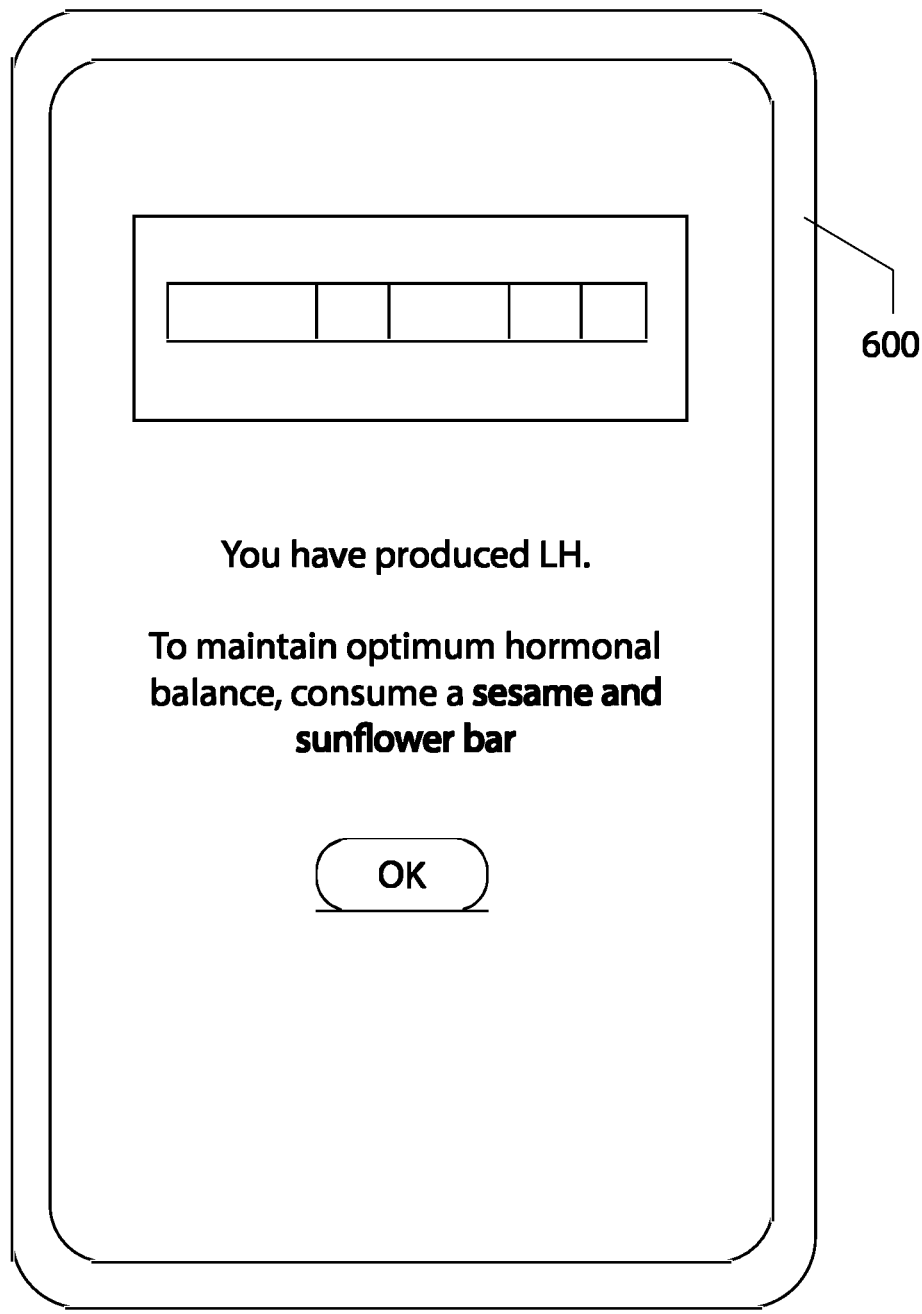
FIG. 13 depicts an exemplary graphical user interface associated with the seed consumption system, wherein the result of a diagnostic test is displayed in association with an interpretation displayed as a unique message.
Figure 14:
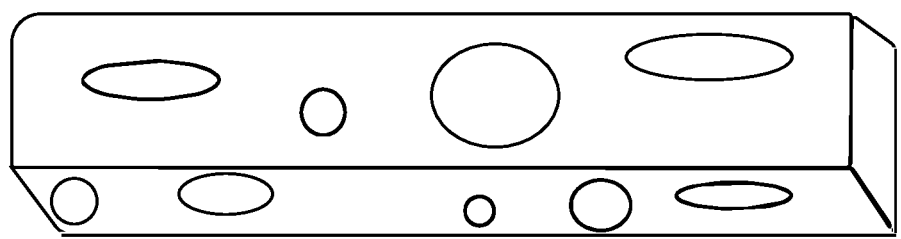
FIG. 14 depicts an exemplary single consumable food item substantially in the form of a snack bar.

In varying examples the system comprises a graphical user interface. The graphical user interface is configured in accordance with mechanisms as well understood by those in the art to operate on a display 605. The processor may the graphical user interface to present one result or a series of results, and/or one or a series of unique message(s) 501 to a user within a graphical user interface, optionally via the Patient-Facing Application, such as is illustrated by FIG. 9. In an example, results and/or one or a series of unique message(s) 501 are also presented to a separate user via a graphical user interface operating in conjunction with the Healthcare Professional Facing Application. In varying embodiments, the graphical user interface is configured to operate on a smartphone 600, a personal computer, a tablet, or within a web browser operating on another such device. In a particular example, the results for each diagnostic test 100 displayed within a graphical user interface featuring the depiction of a calendar 5000, with the result, interpretation and/or unique message 501 associated with each diagnostic test 100 previously performed presented in association with the date each diagnostic test was performed within a calendar 5000 displayed similar to that as depicted in an exemplary embodiment of the invention in FIG. 11. In an embodiment, the various phases of the menstrual cycle, for instance menstruation, the follicular phase and the luteal phase, are indicated by color coding the days associated with each phase as indicated based on the results or indications of one or more diagnostic test(s) 100. In another particular example, a listing of available times to consult with a healthcare professional located in the same jurisdiction as the detected location of the user 900 of the application operating in association with a mobile device, optionally detected by utilizing the GPS of the smartphone 600, displayed in order of available dates starting with the nearest available date within a graphical user interface operating in conjunction with the application operating in association with a mobile device, as depicted in FIG. 12. In various embodiments, the graphical user interface is configured to display a positivity scale 5685 as described herein, and as more particularly shown in FIG. 28. In various embodiments of the invention, the graphical user interface incorporates the designs or elements of the designs depicted in the present applicant's U.S. Design patent application 29/788,306 filed on Apr. 29, 2021, which is hereby incorporated by reference in its entirety. In various embodiments, the positivity scale 5685 is configured to provide a visual reference of a result of a diagnostic test to the threshold of the diagnostic test. The present inventor has noted that it is helpful for a user of an application configured to provide an indication of a result of a diagnostic test to know how close to the threshold for a positive or negative result of the diagnostic test the actual indicated result on the image or photograph of the diagnostic test is, for example. In the preferred embodiment, the positivity scale 5685 comprises a bar chart. As shown (in greyscale) in FIG. 28, the bar chart comprises a gradient of a plurality of colors. The colors indicated may be any variety of colors, or different lightnesses of the same color, for example. In various embodiments, each of the plurality of colors depicted on the positivity scale 5685 is a color that may be depicted by the detection zone of diagnostic test and detectible by a camera, the camera operating with a smart device, for example. In various embodiments, each of the plurality of colors is associated with a color code, for example an RGB color code, any color code associated with any of the red, blue or green channels individually, or a HEX color code. In various examples of the positivity scale 5685, analysis of the diagnostic test is performed to correlate each of the color codes correlating to a known value of concentration of an analyte or hormone, In an example of the invention, if the color code detected by the camera is not correlated to a known value of hormone or analyte concentration, the hormone or analyte concentration associated with the closest color value to the detected color value is associated with the detected color value. In embodiments, an application associated with a graphical user interface provides the context for the display of the positivity scale 5685. As such, it is a teaching of the invention that the positivity scale 5685 substantially comprises a bar chart displayed upon a graphical user interface configured to provide a visual relationship of a color intensity of an result indicated on an image of a diagnostic test to a known (or estimated, based on the closest color code having a known concentration of a hormone or analyte to the detected color code) concentration of a hormone or analyte correlating to the color intensity. In various embodiments, to provide an indication on the positivity scale 5685 of where the threshold is relative to the detected or estimated concentration of a hormone or analyte, it is a further teaching of the invention for the positivity scale 5685 to comprise a visual indication of the color corresponding to the result threshold of the diagnostic test overlayed onto the bar chart, and further comprise a visual indication of the location of the color 5687 on the bar chart in relation to the threshold, as depicted (in grayscale, though in various embodiments the color values are non-grayscale) in FIG. 28 in an exemplary embodiment.

The preferred embodiment of the invention comprises a calendar 5000. In an example, the calendar 5000 is configured for use in association with the collected results, each result from one of a plurality of diagnostic tests, and the depiction of the collected results within a graphical user interface associated with an application operating in association with a mobile device, as shown in FIG. 11. The present inventor has recognized the unique usefulness of organizing the collected result(s), along with associated indication(s) and interpretation(s), of a series of diagnostic tests for depiction in a calendar format, in part due to the cyclical nature of the menstrual cycle, in part due to the ease by which specific trends are observable within a calendar format, and in part due to the ability to identify specific phases of the menstrual cycle and group certain messages associated with the menstrual cycle by color coding periods of consecutive days within a depicted calendar, which comprises a teaching of an embodiment. The calendar 5000 configured for depiction within a graphical user interface associated with the application operating in association with a mobile device may depict the result(s), indication(s), or interpretation(s) of each diagnostic test 100, or a relevant unique message 501, collected for a single person on a daily basis on each date depicted within the calendar 5000. In an exemplary embodiment, each result, or category of results, for positive or negative is represented by a different color as depicted on the date of the collected diagnostic test result. In an exemplary embodiment, each of the phases of the menstrual cycle and/or the fertile and infertile timeframes of a menstrual cycle as interpreted by the collected series of diagnostic test results, is represented by a different color depicted over a series of days on the depicted calendar 5000. In an exemplary embodiment, each date is labelled with text identifying the hormone or analyte for which the result and/or interpretation is derived as illustrated by FIG. 11 in an exemplary embodiment.

The calendar 5000 depicted within a graphical user interface in an embodiment is configured to display a positive or negative result for each diagnostic test 100 on the date which the test was collected. In an embodiment, each interpretation of each diagnostic test 100 is represented by a different color and associated with the date of the diagnostic test was performed in the calendar 5000 in the graphical user interface. In accordance with the foregoing, it is a teaching of an embodiment and a step of the method of use of the system to engage in allocating the result from a diagnostic test consisting of a lateral flow assay test configured to detect for the presence or absence of at least pregnanediol glucuronide in urine to the specific calendar date upon which the result was determined 2002. It is also a teaching of and step of the method of use of the system to engage in storing the result and the calendar date associated with the result 2003, in coordination with other components of the system, including the Communicatively Connected Storage Medium, as described herein. It is also a step of the method of use of the system to engage in displaying the results of a diagnostic test via the graphical user interface 2008. It is likewise a step of the method of use of the system to engage in displaying the results of a diagnostic test via the graphical user interface featuring a calendar with the result of each test displayed on in association with the date each test was performed within the displayed calendar 2025. The present inventor has recognized that such a configuration allows for the easy identification of hormonal trends associated with the menstrual cycle. The present inventor has also recognized that such teaching representing an aspect of the invention in an embodiment is a solution to the confusion faced by a lay user of a diagnostic test with regard to interpreting an indicated result, particularly when a single diagnostic test 100 is configured to evaluate for the presence or absence of multiple hormones and/or analytes within a single sample of urine simultaneously. The present inventor has recognized that such problem is especially poignant, and the relevant solution that the foregoing represents is especially valuable, when the diagnostic test 100 lacks plain language text labelling on a readable surface to distinguish between the result indication lines and/or visual indications of the diagnostic test 100.

A calendar 5000 similar to that configured for depiction within the graphical user interface associated with the application operating in association with a mobile device, may also be configured for depiction within an application intended for use by a healthcare professional, such as the Healthcare Professional-Facing Application as described elsewhere herein, when a user of the application intended for use by a healthcare professional is accessing the information relevant to one subject person.

In an embodiment, the application operating in association with a mobile device may be configured to utilize the calendar 5000 and more specifically its association of dates to the specific diagnostic tests performed to interact with a Patient Information Integration Tool associated with the invention. The purpose of the Patient Information Integration Tool is to associate the interpreted result of the diagnostic test and the time or calendar date that the interpreted result was collected with the patient's demographic information and optionally other results associated with the patient. In an embodiment, the Patient Information Integration Tool may comprise an application programming interface (API) configured to facilitate the incoming and outgoing information formatted in an interoperable format, such as HL7 or others described in the Fast Healthcare Interoperability Resources specification, as is understood by those skilled in the art. In various embodiments, the Patient Information Integration Tool is configured as the examples described in U.S. patent application Ser. No. 14/997,503 filed on Jan. 16, 2016, U.S. patent application Ser. No. 12/391,120 filed on Feb. 23, 2009; U.S. patent application Ser. No. 16/113,652 filed on Aug. 27, 2018; and U.S. patent application Ser. No. 15/862,837 filed on Jan. 5, 2018, each of which are incorporated by reference. In an embodiment, the calendar 5000 is configured to collect and depict information associated with a specific date from other electronic medical record (EMR) systems and other healthcare modalities via the Patient Information Integration Tool. In an embodiment, the Patient Information Integration Tool is configured to display alerts optionally in association with the calendar 5000, in an example as described in U.S. patent application Ser. No. 16/743,029 filed on Jan. 15, 2020, which is hereby incorporated by reference. In an example of the invention, the calendar 5000 is configured to display elements of a treatment plan collected from external sources optionally based in part on the results of the diagnostic test, for example as is described in more detail in U.S. patent application Ser. No. 15/596,356 filed on Oct. 8, 2019 which is hereby incorporated by reference. Also in accordance with such teachings, in various embodiments, the method of use of the system further comprises the step of formatting the result from the diagnostic test, optionally comprising a lateral flow assay test, in combination with individually identifying information associated with the subject woman and the date the test was performed into formatted results for interoperable transfer to a computing device configured to interpret and store electronic personal health information 2011, optionally facilitated in association with the Processor, the Computing Device, the Patient Facing Application and/or the Patient Information Integration Tool as described herein. Likewise, it is a further teaching of the method of use of the system to provide a step for facilitating the transfer of the result in an interoperable format either individually or in combination with one or more additional results associated with the same subject woman 2012, optionally facilitated in association with the Patient Information Integration Tool.

In various embodiments, each diagnostic test result is collected in association with other aspects of the invention as described elsewhere herein. Each diagnostic test result may be correlated with a date provided or otherwise determined by the computing device as well understood in the art prior to association with the calendar 5000 for depiction on a specific date. The diagnostic test 100 collected in alternative embodiments may comprise a diagnostic test configured as other than as described herein. In accordance, it is therefore a step of the method of use of the system to engage in allocating the result from the diagnostic test 100, optionally a lateral flow assay test, configured to detect for the presence or absence of at least one additional hormone or hormonal analyte selected from the group consisting of luteinizing hormone, estrogen, E3G, FSH, and human chorionic gonadotropin, to the specific calendar date upon which the result was determined 2006. The present inventor has recognized that such allocation of such a result to such a calendar date may facilitate the subsequent display of such a result within a calendar depicted within the graphical user interface associated with the application operating in association with a mobile device, optionally the Patient-Facing Application, and/or the Healthcare Professional-Facing Application and further facilitate the identification of trends of hormonal levels which may prove relevant to or otherwise allow for the diagnosis of medical conditions, optionally by a healthcare professional utilizing a Healthcare Professional-Facing Application as described elsewhere herein. Such information may be displayed with and/or in relation to the date of ovulation or date of suspected ovulation as determined in accordance with the mechanisms described elsewhere herein. Resultantly, further steps of the method of use of the system include associating and storing a specific calendar date with the ovulation date of the subject woman 2007 and displaying the results via a graphical user interface 2008 as described herein. In one example, the ovulation date is manually entered via the graphical user interface associated with the application operating in association with a mobile device, optionally by selecting a date within a calendar depicted therein as described herein. In accordance with the teachings and the components of the system as described elsewhere herein, in various embodiments, the method of use of the system comprises the step of allocating the result from the diagnostic test, optionally a lateral flow assay test configured to detect for at least one additional hormone or hormonal analyte selected from the group consisting of luteinizing hormone, estrogen, an estrogen metabolite such as E3G, FSH, and human chorionic gonadotropin to the specific calendar date upon which the result was determined 2010, optionally in association with the calendar 5000.

In another example, the calendar is depicted on a printed insert within the packaging and designed for utilization in association with a Diagnostic Test Key, the Diagnostic Test Key optionally comprising a color intensity key 800, for visual interpretation of the results of the diagnostic test to allow a lay user of the diagnostic test to manually record results on the calendar in association with the date each of a plurality of diagnostic test results was collected. The calendar depicted on a printed insert is optionally an aspect of the invention in addition to or as a backup to the calendar 5000 configured for depiction within a graphical user interface associated with the application operating in association with a mobile device.

Fertility Tracking System

Embodiments of the invention comprise a fertility tracking system incorporating aspects of the methods described elsewhere herein and the diagnostic test(s) 100 described elsewhere herein. In the preferred embodiment, the system provides information relevant to hormonal levels and changes of hormonal levels over a series of days within a single menstrual cycle, or optionally in comparison to hormonal levels or trends of hormonal levels occurring in previous or subsequent menstrual cycles.

The fertility tracking system in the preferred embodiment comprises a specified quantity of diagnostic tests 100, each diagnostic test 100 consisting of a lateral flow assay, optionally a sandwich assay, each comprising a testing zone and corresponding result indication line configured to detect for the presence or absence of an hormone or analyte, optionally pregnanediol glucuronide in urine at a threshold selected from the range of 1 µg/mL-10 µg/mL. In an embodiment of the diagnostic test 100, the lateral flow assay pertinent to any of PdG and E3G is a competitive assay and the lateral flow assay pertinent to any of LH, FSH and hCG is a sandwich assay. In the preferred embodiment, the lateral flow assay comprising a testing zone and corresponding result indication line configured to detect for the presence or absence of pregnanediol glucuronide is configured to detect for the presence or absence of pregnanediol glucuronide at a threshold of 5 µg/mL. In an embodiment, the diagnostic tests consisting of a lateral flow assay, optionally a sandwich and/or competitive assay, comprising a testing zone and corresponding result indication line configured to detect for the presence or absence of pregnanediol glucuronide in urine are configured such that the presence of only one line (i.e. the control line 105) a positive result and the presence of two lines (i.e. the control line 105 and the first result indication line 107) indicates a negative result for the presence of pregnanediol glucuronide at a threshold selected from the range of 1 µg/mL-10 µg/mL. The present inventor has noted the previous unavailability and unmet need of such diagnostic tests as is well established in the art. In an embodiment, the specified quantity is useful in association with the tracking of hormonal levels on a daily basis over a specified period corresponding to utilization during one single menstrual cycle.

Figure 15:
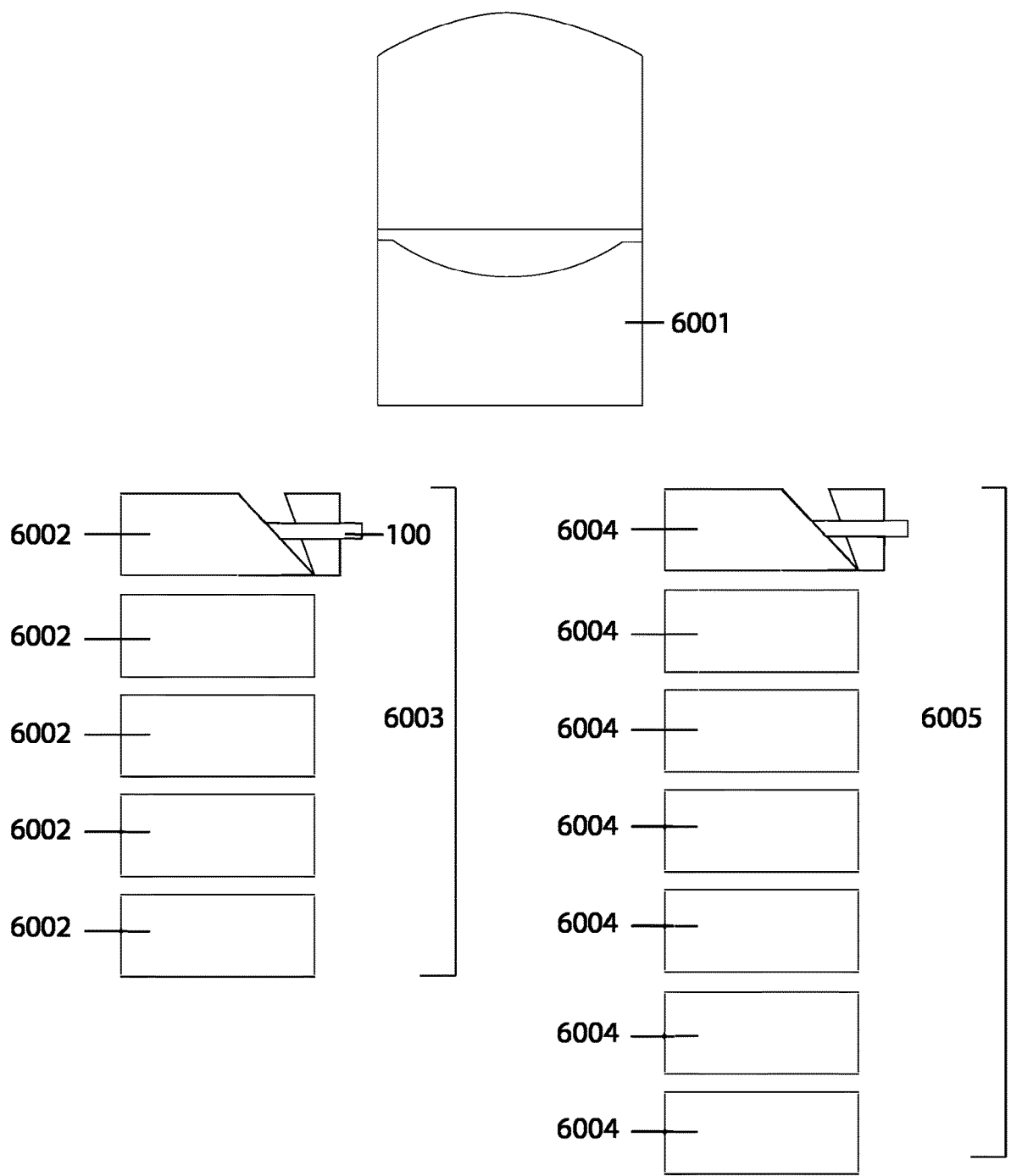
FIG. 15 depicts embodiments of the system comprising a plurality of diagnostic tests and a container.

The present inventor has discovered that the quantities of diagnostic tests 100 as described herein is indicated to allow usage of the fertility tracking system by a layperson without the need to calculate the number of diagnostic tests 100 needed based on readings of each diagnostic test 100 or based on the calculation of the length of the menstrual cycle or its phases. In various embodiments, the fertility tracking system comprises a quantity of diagnostic tests, the quantity selected from the range of 4-15 diagnostic tests 6003, each diagnostic test consisting of a lateral flow assay configured to detect for the presence or absence of pregnanediol glucuronide in urine individually placed within a sealed packet 6002. In the preferred embodiment, the fertility tracking system comprises 5 diagnostic tests configured to detect for the presence or absence of pregnanediol glucuronide at a threshold in urine as depicted in FIG. 15. The fertility tracking system further comprises a quantity of diagnostic tests, the quantity selected from the range of 7-25 diagnostic tests 6005, each diagnostic test consisting of a lateral flow assay comprising a testing zone and corresponding result indication line configured to detect for the presence or absence of luteinizing hormone at a threshold chosen from the range of 15 mIU/mL-50 mIU/mL individually placed within a sealed packet 6004 as depicted in FIG. 15. In the preferred embodiment, the lateral flow assay comprising a testing zone and corresponding result indication line configured to detect for the presence or absence of luteinizing hormone is configured to detect for the presence or absence of luteinizing hormone at a threshold of 25 mIU/mL.

The present inventor has recognized that the fertility tracking system comprising the specified quantities of diagnostic tests configured to detect for the presence or absence of pregnanediol glucuronide in urine at a threshold selected from the range of 1 µg/mL-10 µg/mL, and diagnostic tests configured to detect for the presence or absence of luteinizing hormone in urine at a threshold chosen from the range of 15 mIU/mL-50 mIU/mL, aggregated together into a system in accordance with the teachings herein, facilitates usage by a layperson to allow for the collection of data relevant to the functioning of the menstrual cycle on consecutive days without the need for laboratory evaluation of bodily fluids. The specified quantities of diagnostic tests configured to detect for the presence or absence of pregnanediol glucuronide in urine and diagnostic tests configured to detect for the presence or absence of luteinizing hormone in urine, when taken on a daily basis by a layperson user, provides for the collection of a series of test data without the need for a laboratory evaluation. The present inventor has recognized that the quantities of diagnostic tests within the fertility tracking system as described herein correlate to the amounts of diagnostic tests to evaluate the critical fertility hormones relevant to the assessment of one menstrual cycle. In one embodiment, the collection and recording of results on a series of days within the period of a menstrual cycle may take place even without the use of an external device to collect and record results.

In the preferred embodiment, the quantity of diagnostic tests consisting of a lateral flow assay configured to detect for the presence or absence of pregnanediol glucuronide at a threshold in urine and the quantity of diagnostic tests consisting of a lateral flow assay configured to detect for the presence or absence of luteinizing hormone at a threshold in urine are aggregated together into a single package for ease of use by a lay user. The present inventor has noted that the aggregation of such specified quantities of diagnostic tests into a single package solves the need for clarity and simplicity associated with the number of tests needed for a typical single menstrual cycle to test at least for the starting and/or ending dates associated for the highly fertile and highly infertile timeframes of the menstrual cycle. In the preferred embodiment, each diagnostic test associated with the system is packaged into a sealed packet consisting of an airtight foil pouch containing a desiccant package and a single diagnostic test 100. The benefit of the use of an airtight foil pouch is that it maintains the integrity of each diagnostic test 100 well beyond the timeframe associated with a single menstrual cycle.

The technical specifications associated with the novel construction of such diagnostic tests configured to evaluate for the presence or absence of at least pregnanediol glucuronide at a threshold in is disclosed elsewhere herein, and within the following patent applications, with the benefit of priority claimed to each application: U.S. patent application Ser. No. 16/381,229 filed on Apr. 23, 2019; U.S. patent application Ser. No. 16/544,554 filed on Aug. 19, 2019; U.S. Patent Application 62/720,953 filed on Aug. 22, 2018; PCT Patent Application PCT/US18/68027 filed on Dec. 28, 2018; U.S. patent application Ser. No. 16/381,229 filed on Apr. 11, 2019; U.S. patent application Ser. No. 16/732,766 filed on Jan. 2, 2020; and U.S. patent application Ser. No. 16/732,823 filed on Jan. 2, 2020, and U.S. patent application Ser. No. 17/308,149 filed on May 5, 2021 each of which is incorporated by reference.

It could be advantageous in association with the systems and methods disclosed herein to overlap testing associated with LH and PdG. For instance, on the day following the first diagnostic test 100 indicating the presence of LH at a threshold, in the scenario where a separate diagnostic test 100 indicates the absence of LH at a threshold and on the same day a diagnostic test 100 indicates the presence of PdG at a threshold, where the diagnostic test 100 indicating the absence of LH and the diagnostic test 100 indicating the presence of PdG have evaluated the same sample of urine, such result in association with the diagnostic tests indicates that a woman has successfully ovulated in accordance with the teachings of the invention. The present inventor has recognized that such a novel combination of multiple specially configured diagnostic tests (the diagnostic tests specially configured as described elsewhere herein) performed in an intentional fashion over a series of more than one day represents a substantial and important improvement over previously known and available mechanisms for testing.

The present inventor has further recognized that in accordance with the invention, testing for PdG and LH on the same day could be beneficial because if one does not obtain an indication on a diagnostic test indicating the presence of a PdG at a threshold following an indication on a diagnostic test indicating the presence of LH at a threshold on the same day or the previous day, it could mean that a false LH surge has occurred, meaning that the woman has not ovulated yet. A false LH surge refers to a surge in LH hormone that does not result in ovulation or the release of progesterone, correlating to the presence of PdG in urine. Relatedly, in some conditions, such as polycystic ovary syndrome (PCOS), and also in a small percentage of normal menstrual cycles, the surges in LH do not actually result in ovulation. Therefore, in accordance with the present invention the present inventor has discovered that it is advantageous to continue to monitor LH until the subject woman tested has confirmed that ovulation has successfully and/or sufficiently occurred. This is indicated in accordance with a teaching of an embodiment by the presence of serum progesterone which correlates to the presence of pregnanediol glucuronide (PdG) above a threshold in urine. Therefore, as configured, the fertility tracking system as, which combines diagnostic testing for at least both LH and PdG as facilitated by the specially configured diagnostic tests as described elsewhere herein—represents a significant and important improvement over prior art mechanisms and methods featuring only testing for LH. In various embodiments, the aforementioned teachings are utilized in the association of the creation of indications and interpretations, optionally for use in association with a unique message 501, as described elsewhere herein.

The present inventor has recognized the risk of a false LH surge associated with the usage of ovulation predictor kits as known in the prior art, which the teachings of the present invention specifically address and represent a significant improvement over the prior art. Therefore, in an aspect, it is a teaching of the fertility tracking system as described herein to facilitate the simultaneous and/or sequential testing of LH and PdG to mitigate the risk of detecting a false LH surge association with prior art utilization of diagnostic tests configured to detect LH only. The steps of simultaneously and/or sequentially testing for PdG following a positive result for LH forms a teaching of the method embodiment of the invention, and is enabled by the specially configured diagnostic tests 100 configured to evaluate for the presence or absence of PdG at a threshold as described elsewhere herein.

In a method of use in association with an embodiment of the invention, it is a teaching to perform the step of evaluating a bodily fluid once daily for the presence or absence of PdG at a threshold during a specified timeframe forming a portion of the menstrual cycle. To facilitate the provision of enough diagnostic tests to accomplish such evaluation without the need for calculation, it is an aspect of the invention to provide a quantity selected from the range inclusive of 4-15 diagnostic tests configured to evaluate for the presence or absence of PdG at threshold. It is an aspect of a method embodiment of the invention that PdG testing should take place daily, for consecutive days up to 10 days past the date of suspected ovulation. In associated steps, the date of the first indicated LH surge in a menstrual cycle is considered the date of suspected ovulation. In an associated method embodiment, the earliest a woman should start testing for PdG in an exemplary method is two days after the date of suspected ovulation. In a method embodiment of the invention featuring the step of evaluating the same bodily fluid sample for both LH and PdG by one or more diagnostic tests configured to evaluate for the presence or absence of both LH and PdG each at a unique threshold, if LH surges on one or more subsequent dates without a corresponding increase in PdG after the one or more previous surges in LH, the date of the most recent subsequent LH surge will replace the all other dates of suspected ovulation, as the new and overriding date of suspected ovulation for that menstrual cycle for purposes of timing the testing of diagnostic tests configured to detect for the presence or absence of pregnanediol glucuronide at a threshold in urine. It is a teaching of a method embodiment to perform the steps of associating and storing a specific calendar date with the ovulation date of the subject woman 2004, whereby the ovulation date is the date of suspected ovulation determined in accordance with the foregoing. It is a teaching of an embodiment that such association and storage of the specific calendar date with the ovulation date takes place in association with the other components of the invention, especially the Processor, the Computing Device, the calendar, the graphical user interface and the communicatively connected storage medium in an example, each as described elsewhere herein. It is a further teaching of a method embodiment of the invention to perform the step associated with utilization of the system to engage in displaying the results via a graphical user interface 2005 in an example.

As a result, to account for the potential of one or more false LH surges in a single cycle, the present inventor has discovered that it is advantageous to provide a single fertility tracking system comprising a quantity of up to 25 diagnostic tests configured to detect the presence or absence of LH in urine at a threshold within a sealed packet 6005 as described elsewhere herein and additionally a quantity of up to 15 diagnostic tests configured to detect for the presence or absence of pregnanediol glucuronide at a threshold within a sealed packet 6003, optionally a quantity of 8, each such individual diagnostic test 100 configured as described elsewhere herein, aggregated into a single package 6001, optionally to facilitate utilization of the diagnostic tests in association with the methods described herein. In association with intended methods of utilization of the fertility tracking system, the subject woman should perform a diagnostic test 100, the diagnostic test configured to detect for the presence or absence of pregnanediol glucuronide in urine at a threshold selected from the range inclusive of 1 µg/mL-10 µg/mL, to evaluate her urine once daily until 10 days after the date of suspected ovulation. Alternatively or in combination, the subject woman in a related method performs such a diagnostic test on a daily basis during the timeframe inclusive of 7-10 days past the date of suspected ovulation to evaluate her urine, and confirm sufficient ovulation following four consecutive diagnostic tests each taken once daily on four consecutive days each demonstrating an indicated result for the presence of pregnanediol glucuronide in the tested urine, optionally in accordance with the methods disclosed in U.S. patent application Ser. No. 16/732,766 filed on Jan. 2, 2020 and U.S. patent application Ser. No. 17/308,149 filed on May 5, 2021 each hereby incorporated by reference in its entirety herein with priority claimed thereto.

To account for cases where a subject woman evaluating her fertility evidences multiple false LH surges within a single cycle, it is a teaching of a method embodiment to perform the step of evaluating urine for the presence or absence of pregnanediol glucuronide on a daily basis for a plurality of up to 12 consecutive days beyond 2-10 days past suspected ovulation (as indicated by the most recent diagnostic test indicating a positive result for the presence of luteinizing hormone as a threshold), and therefore a fertility testing system comprising a quantity of up to 15 such diagnostic tests (optionally to allow for user errors or associated duplicate testing in an example) or a quantity of as few as 4 such diagnostic tests each configured to detect for the presence or absence of pregnanediol glucuronide in urine is preferred.

On the other hand, for some women (such as those who know that they do not have PCOS, for instance), the risk of a false LH surge is much lower. Therefore, in one example, it is advantageous to have as few as 4 diagnostic tests configured to detect for the presence or absence of pregnanediol glucuronide at a threshold and is a teaching of an embodiment. Such a quantity corresponds to that necessary to evaluate urine on a once daily basis between the dates inclusive of 7-10 days after the date of suspected ovulation, in accordance with methods described with more particularity in U.S. patent application Ser. No. 16/732,766 filed on Jan. 20, 2020, and U.S. patent application Ser. No. 17/308, 149 filed on May 5, 2021, each of which as noted previously this application claims the benefit of and incorporates by reference in its entirety. For example, a sequence of diagnostic tests taken daily on the dates including days 7-10 past the suspected ovulation date is suggestive of proper corpus *luteum* functionality in one intended method of usage of the fertility tracking system.

For similar reasons, it is likewise advantageous in an example to incorporate as few as 7 diagnostic tests configured to detect for the presence or absence of luteinizing hormone at a threshold in urine into the fertility tracking system. For cost saving or efficiency purposes, such a configuration may be preferred in the cases of healthy women with healthy cycles. The quantity of tests necessary for a single fertility testing system intended for use during a single menstrual cycle is informed by the needs of a healthy woman in one example. In such an instance, an example result may occur where LH testing is performed on a daily basis starting on the 10th day of the menstrual cycle, indicating a LH surge on the third day of testing for LH (the 13th day of the menstrual cycle), with the testing for PdG commencing on the second day following the first test indicating the presence of LH at a threshold in urine (the 15th day of the menstrual cycle) in accordance with the preferred method of use of the fertility tracking system, that test indicating the presence of PdG in urine at a threshold on the 15th day of the menstrual cycle. In such a case only five diagnostic tests configured to detect for the presence or absence of LH at a threshold would need to be performed. Further, in accordance with the preferred method of use, only four diagnostic tests configured to detect for the presence or absence of PdG would need to be performed in a single menstrual cycle, each on a daily basis during the period of 7-10 days past suspected ovulation. It is a teaching of an alternative embodiment that once an LH test results in a positive reading correlating to an LH surge, generally (though not always) following a negative LH test, this signifies the time to change to commence testing for PdG over a timeframe potentially preceding the 7-10 days past suspected ovulation window. In various embodiments, the systems associated with the invention are configured to incorporate such quantities.

The present inventor has recognized that the quantity of diagnostic tests configured to detect for the presence or absence of LH at a threshold is optimally selected from the range inclusive of 7-25 such diagnostic tests, in part because a subject woman may benefit from testing for LH on multiple times per day in certain circumstances. For example, the present inventor recognizes that LH can surge in the afternoon or the morning, and the surge could be for a very short duration. Therefore the present inventor has further recognized that in order to detect the transient increase in LH, testing multiple times per day can be advantageous. Therefore, as LH may be more advantageous in the afternoon as opposed to the morning, or in addition to testing in the morning, a teaching of which is incorporated into an embodiment of the invention, such teaching represents a significant departure from the teachings associated with LH testing in the prior art, which recommend protocols associated with only testing in the morning. Such teachings relate to the quantity of diagnostic tests configured to detect for the presence or absence of LH to incorporate into the system in association with additional diagnostic tests at least comprising a plurality of diagnostic tests configured to detect for the presence or absence of PdG chosen in association with embodiments of the system described herein.

In an embodiment of the invention, the intended use of testing for LH and the testing for PdG occurs via a single strip containing separate result indication lines each configured to evaluate for the presence or absence of a distinct hormone or analyte each at a threshold. Therefore, in association with such intended use, the system—instead of comprising two categories of diagnostic tests, each category of diagnostic test comprising a quantities of diagnostic tests configured to evaluate for the presence or absence of only one hormone or analyte—alternatively comprises as few as 10 and as many as 25 diagnostic tests configured to evaluate for at least for the presence or absence of PdG at a threshold in a first testing zone corresponding to a first result indication line 107 and the presence or absence of LH at a threshold in a second testing zone corresponding to a second result indication line 108. In an example, each diagnostic test 100 comprises a single lateral flow assay comprising a plurality of separate testing zones, each testing zone configured to evaluate a separate hormone or analyte as described elsewhere herein. As such it is a teaching of an embodiment of the invention to comprise a single package 6001, optionally a cardboard box, comprising a quantity of diagnostic tests selected from the range inclusive of 10-25 diagnostic tests, wherein each diagnostic test comprises a single lateral flow assay comprising a plurality of separate testing zones, each testing zone configured to evaluate for the presence or absence of a separate hormone or analyte at a threshold and to present a visual result on a corresponding result indication line.

In addition, whether or not incorporated into a single diagnostic test configured to evaluate urine for the presence or absence of a plurality of hormones and/or analytes each at a unique threshold as described elsewhere herein, an example of the invention additionally comprises diagnostic tests comprising testing zones and corresponding result indication lines other than those configured to detect for the presence of LH and PdG. In an example of the invention, diagnostic tests configured to evaluate urine for the presence or absence of FSH at a threshold are included at a quantity selected from the range inclusive of 7-25 diagnostic tests. The present inventor has recognized that a diagnostic test configured to evaluate for the presence or absence of FSH at a threshold is useful, as the presence of FSH signifies when the fertile window opens in the menstrual cycle, as a follicle is "stimulated" or selected by follicle stimulating hormone (FSH), thereby opening the fertile window. The presence of FSH, specifically the presence of FSH in an amount equivalent to a 1.5 fold decrease as compared to a prior diagnostic test indicating the presence of FSH performed in the same menstrual cycle, such fold change optionally determined by comparing the indicated colors to the colors indicated on the color intensity key 800 and associating the indicated FSH concentration with each diagnostic test 100, signifies the stimulation of the follicle and also confirms the opening of the fertile window. For instance, FSH is generally elevated in the beginning of a healthy menstrual cycle. Measuring FSH is also uniquely beneficial for women experiencing menopause or perimenopause in association with the menopause tracking and treatment management system described elsewhere herein, as a persistently high level of FSH may indicate permanent menopause. In an example, the indication for FSH in association with various embodiments may provide a marker for ovarian reserve. In various embodiments, the results indicated by diagnostic test 100 configured to evaluate for the presence of FSH are used in association with other elements of the system to generate indications and/or interpretations as described elsewhere herein, each optionally for display as a unique message 501.

In an example, the invention further comprises diagnostic tests configured to evaluate urine for the presence of estrogen, optionally via detection of an Estrogen Metabolite (E3G), included at a quantity selected from the range inclusive of 7-25 diagnostic tests. The presence of E3G, specifically the presence of E3G in an amount equivalent to a 1.5 increase as compared to a prior diagnostic test 100 indicating the presence of E3G taken in the same menstrual cycle, such fold change optionally determined by comparing the indicated colors to the colors indicated on the color intensity key 800 and associating the indicated E3G concentration with each diagnostic test 100, signifies the maturity of the follicle and also confirms the opening of the fertile window. Examples of the invention incorporating a plurality of diagnostic tests configured to detect for the presence or absence of E3G can provide additional information. For instance, the present inventor has recognized that in comparison to a diagnostic test indicating the presence FSH, a diagnostic test configured to evaluate for the presence of E3G provides a slightly different and potentially complementary indication, namely that after the follicle was selected (signaled by FSH) the maturing follicle has secreted estrogen.

Figure 16:
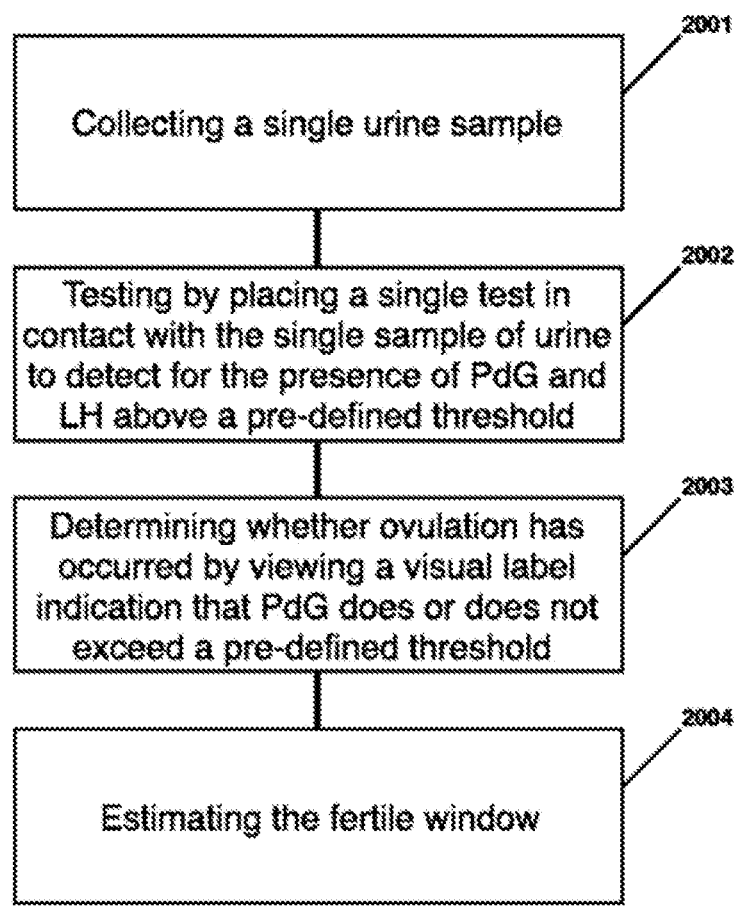
FIG. 16 depicts an exemplary method of use associated with estimating the fertile window of the system.

In an exemplary sequence of testing featuring a plurality of diagnostic tests 100 each configured to evaluate only one hormone or analyte, a method embodiment comprises the step of instructing the subject woman, optionally via the graphical user interface, to commence utilizing a diagnostic test configured to detect the presence or absence of FSH in an applied fluid once daily 9001, optionally at a threshold or optionally by comparison of the degree of change compared to an earlier diagnostic test configured to detect the presence or absence of FSH as described elsewhere herein, on a daily basis commencing on a day chosen from the range inclusive of 2-3 days following the onset of a subject woman's menstruation in a menstrual cycle. In an exemplary method, the step of collecting, on a daily basis, the results of each of a plurality of diagnostic tests by comparing the color intensity indicated on each diagnostic test to a color intensity key 800 to estimate the FSH concentration 9002. Such an exemplary sequence in an embodiment is depicted by FIG. 16.

Following a change in FSH as indicated by a diagnostic test subsequent to at least one earlier taken diagnostic test indicating the presence of FSH in the same menstrual cycle—the change indication optionally representing a 1.5 fold decrease in FSH levels, and optionally detected in association with use of the an application, processor, computing device and/or camera as described elsewhere herein—an exemplary method further comprises the step of instructing the subject woman, optionally via the graphical user interface, to commence utilizing a diagnostic test comprising a testing zone and corresponding result indication line configured to detect the presence of E3G once daily on a daily basis 9003. In an alternative embodiment, the change is indicated or for example by a result on a diagnostic test configured to detect FSH in urine at a threshold demonstrating a level indicated above a threshold followed by a result on a diagnostic test configured to detect FSH in urine demonstrating an indicated level of FSH below a threshold, In an example, the change in FSH is determined by photographing a diagnostic test comprising at least one testing zone configured to evaluate the presence of FSH in the bodily fluid to determine a baseline indicated color intensity in a corresponding result indication line on a date 2-7 days from the onset of menstruation. In an embodiment, an application or computing device is preconfigured with color intensities of such result indication line corresponding to different levels of FSH in an applied fluid, for instance by recording the results for the color intensities occurring in each of a plurality of diagnostic tests each applied with a spiked male urine including known amounts of FSH, optionally in association with the color intensity key 800. In an example, the applied fluid consists of male urine spiked with a known level of FSH. In various embodiments where the color intensity associated with results of a diagnostic test does not precisely match a previously known correlation to an amount of a hormone or analyte (such as FSH or E3G) in urine, the estimated amount is instead determined by substituting the closest color intensity to the indicated color intensity and estimating the level of the amount of hormone or analyte in the applied fluid to be that associated with the closest color intensity. In such manner, the present inventor has recognized that it is possible to determine fold changes in FSH in an applied fluid, for example a 1.5 fold decrease, evidenced by one diagnostic test as compared to a previously taken diagnostic test as a baseline, by correlating color intensities indicated on a diagnostic test to a known level of FSH and ensuring that in methods of use that each diagnostic test utilized in association with the relevant method is similarly configured. Similar mechanisms are useful in correlating color intensities with the levels in an applied bodily fluid of other hormones and/or analytes, such as E3G. Such correlated color intensities are useful in an embodiment comprising a Diagnostic Test Key 200 as described elsewhere herein. It is important to note in association with teachings of the invention that a certain fold decrease in the color intensity indicated over a series of diagnostic tests does not necessarily equate to a similar fold decrease or increase in the actual relevant amount of hormone or analyte in an applied sample. Notably, the present inventor has determined that some diagnostic tests configured with certain carrier proteins are difficult to consistently reproduce, and has also noted that the precision associated with manufacturing consistently reproduced diagnostic tests is important in the effective deployment of such method.

Figure 17:
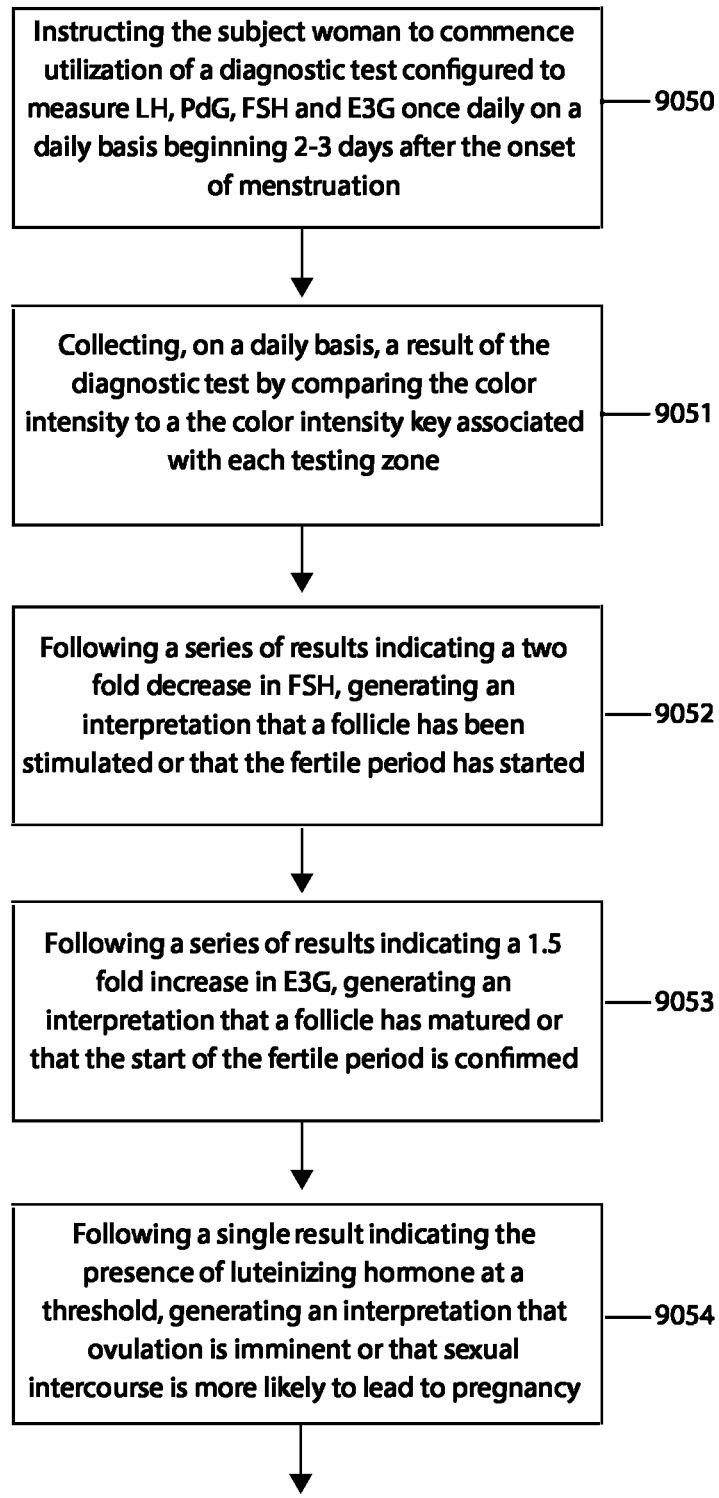
FIG. 17 depicts an exemplary method of use of a system associated with the scheduler.
Figure 17:
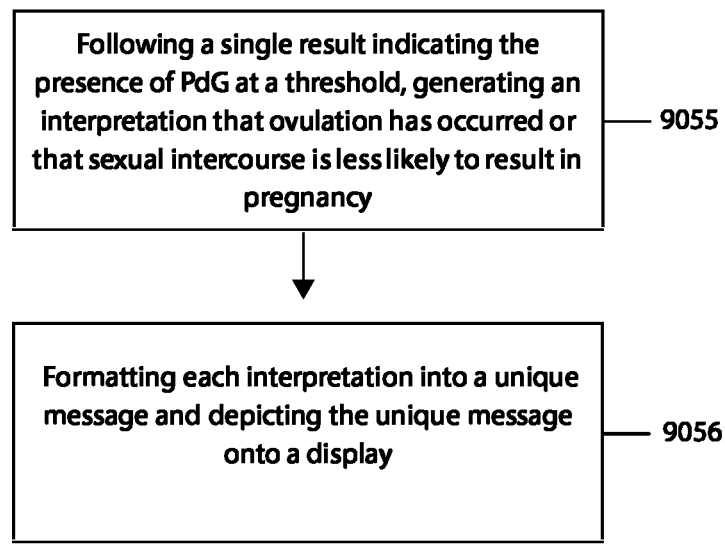
Figure 18:
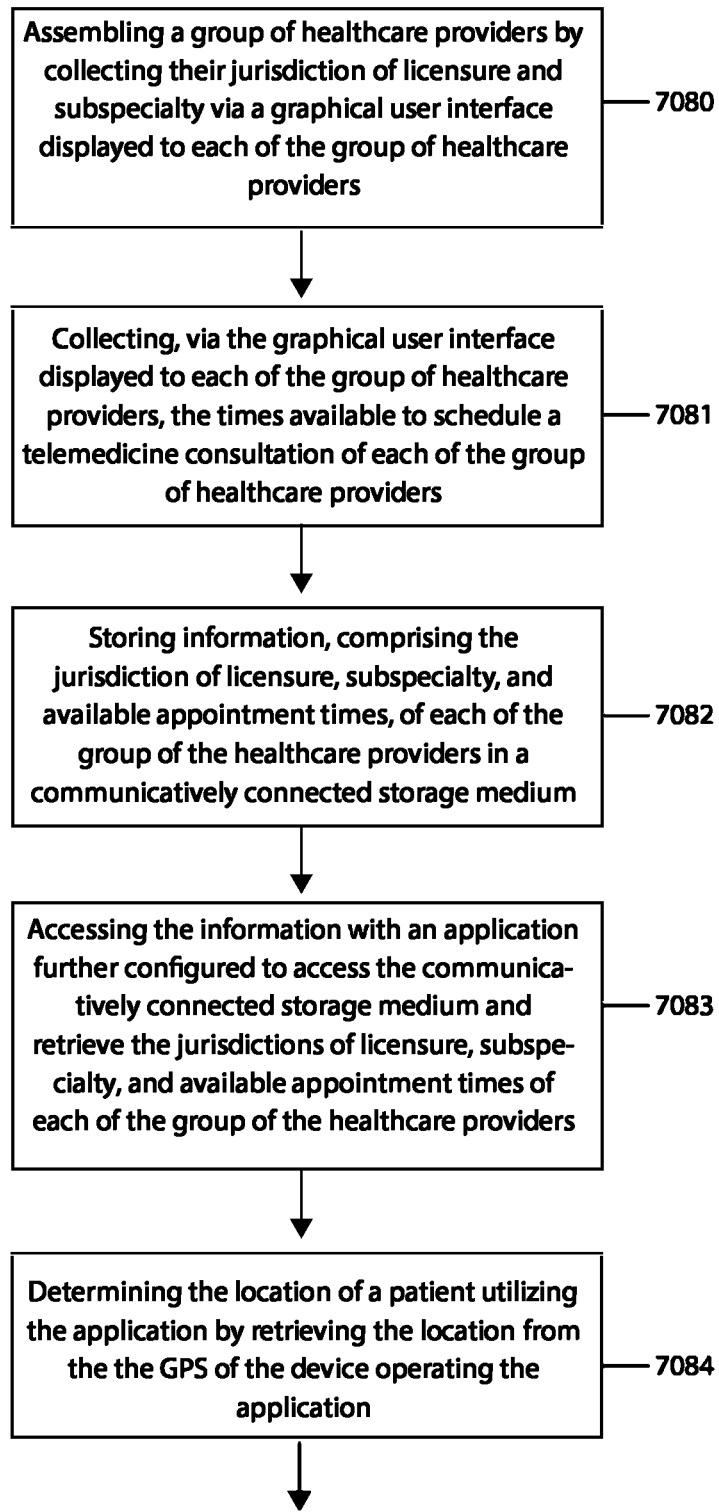
FIG. 18 depicts an exemplary method of use of a system associated with the healthcare professional-facing application.
Figure 18:
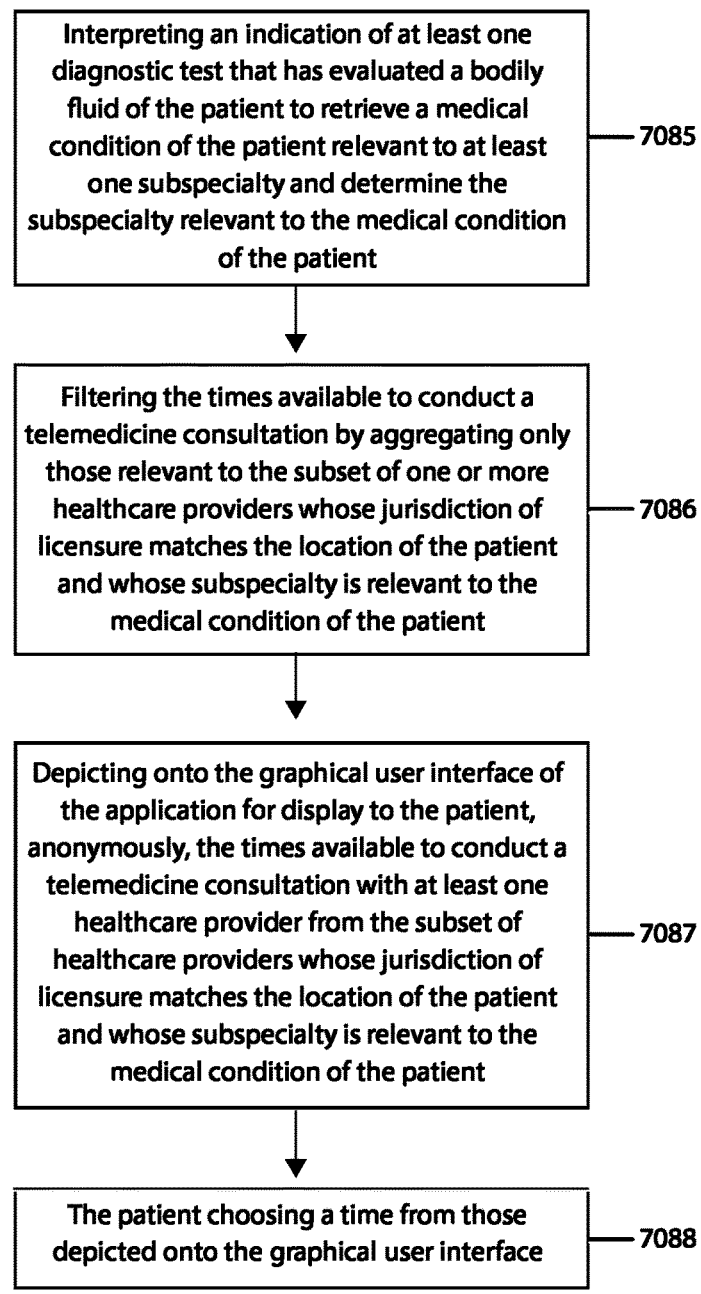
Figure 18:
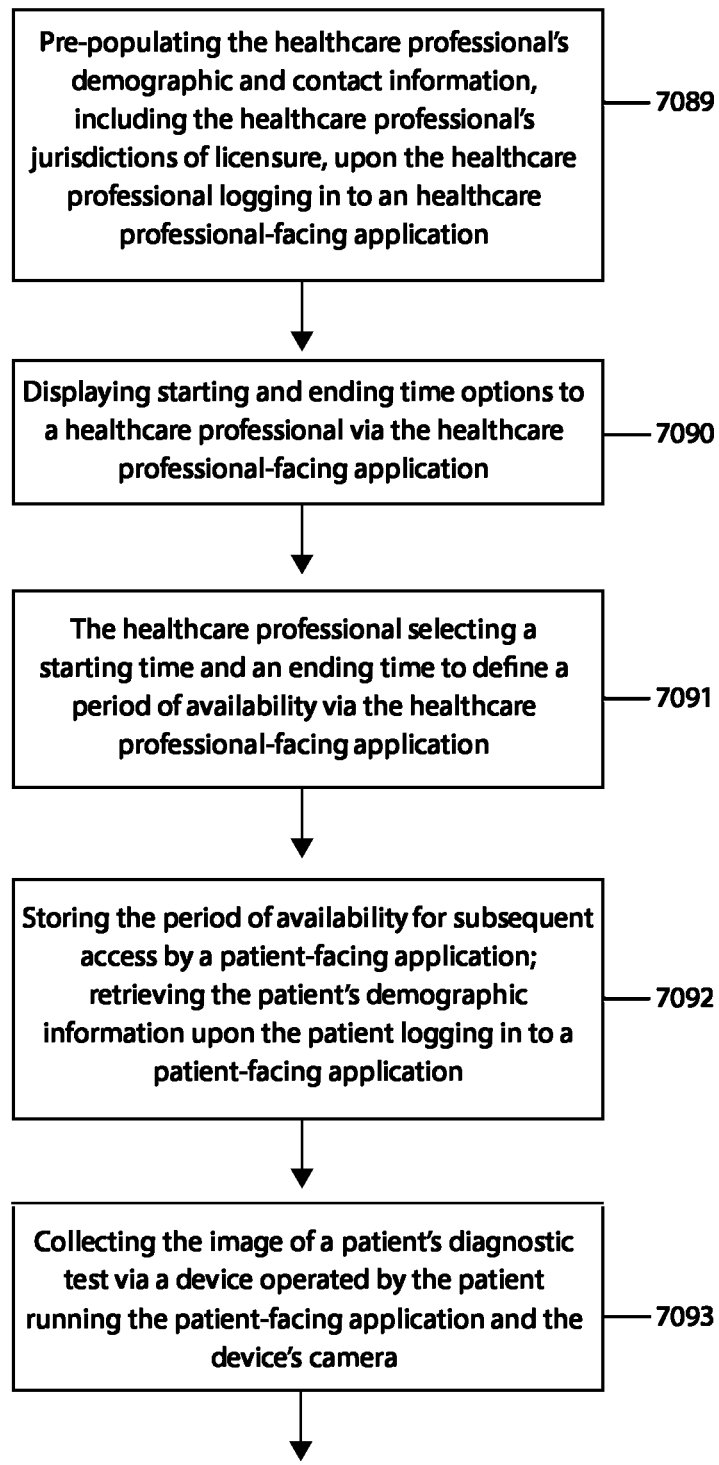
Figure 18:
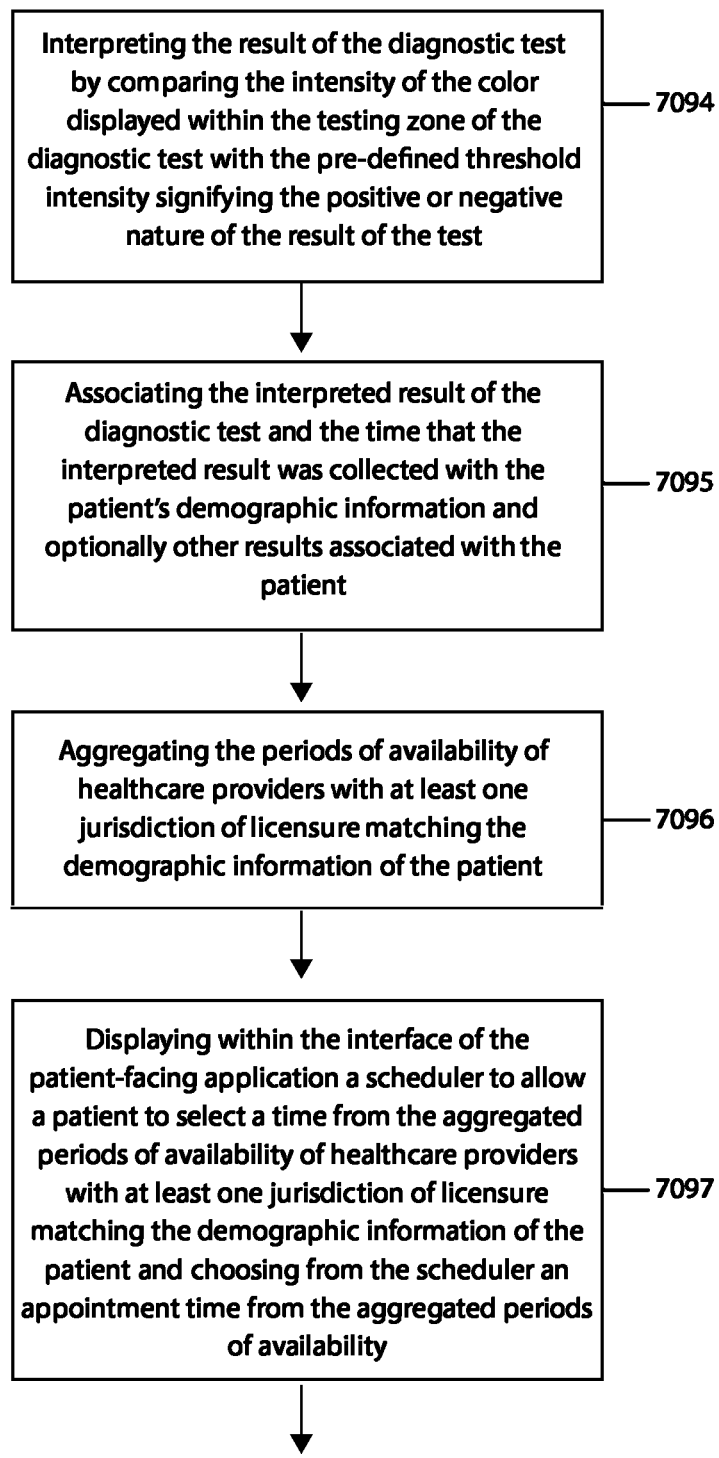
Figure 18:
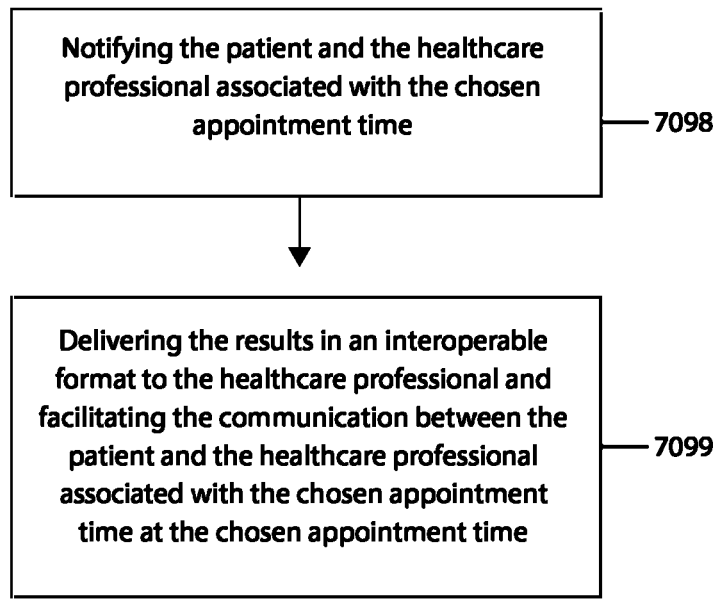
Figure 19:
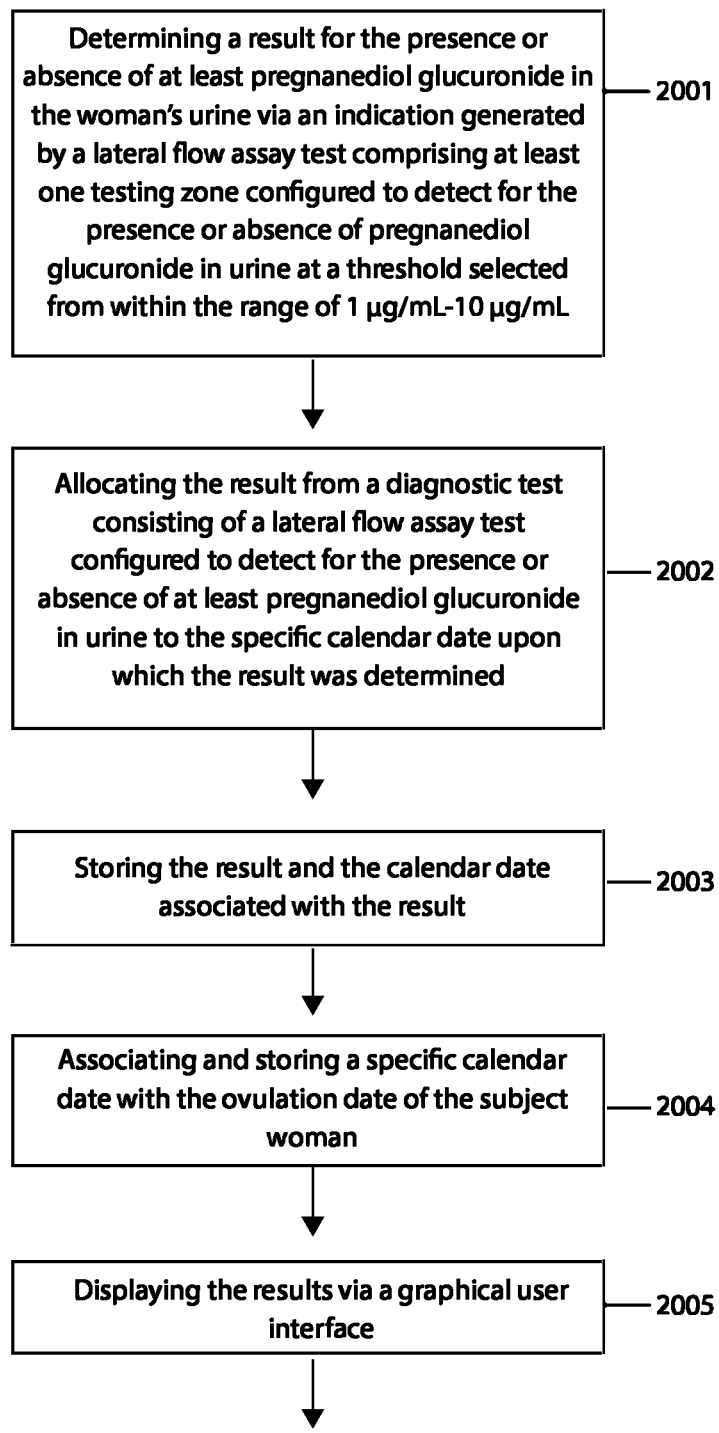
FIG. 19 depicts an exemplary method of use of a system associated with the patient-facing application.
Figure 19:
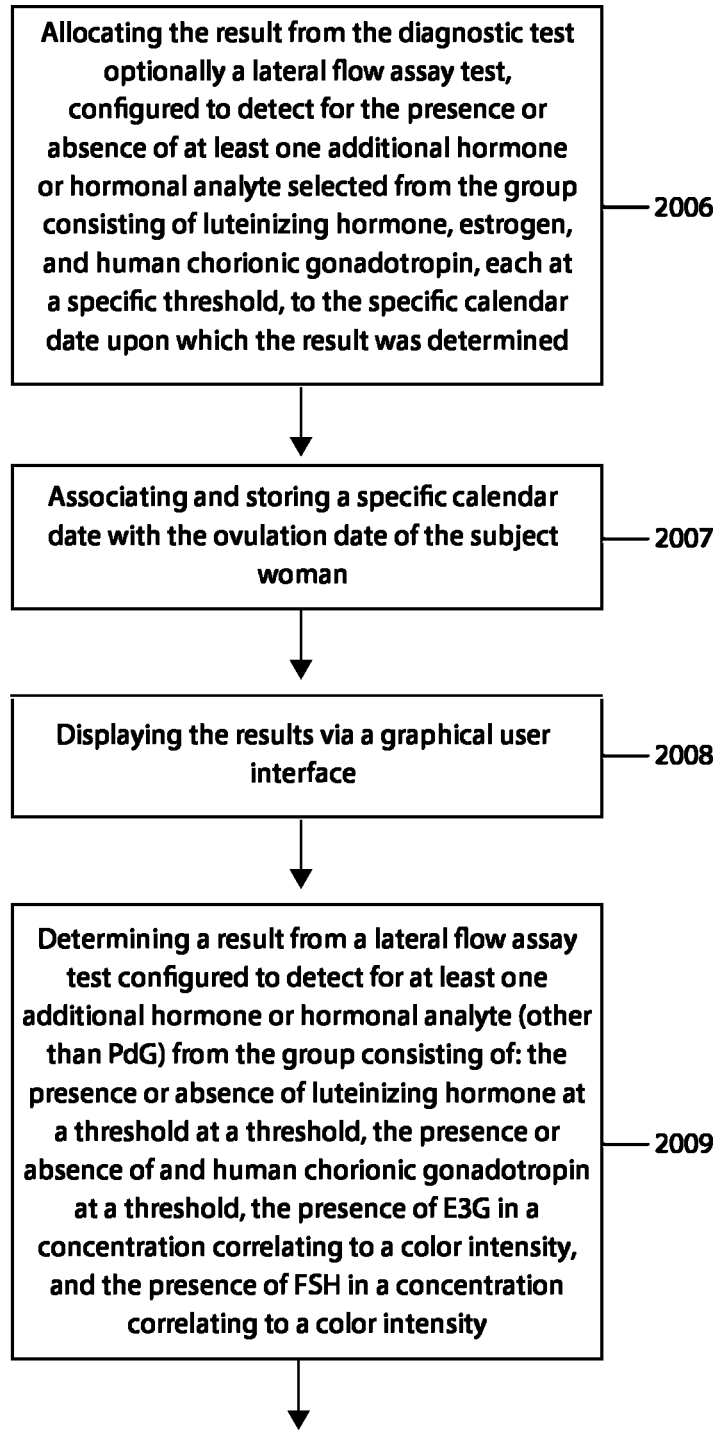
Figure 19:
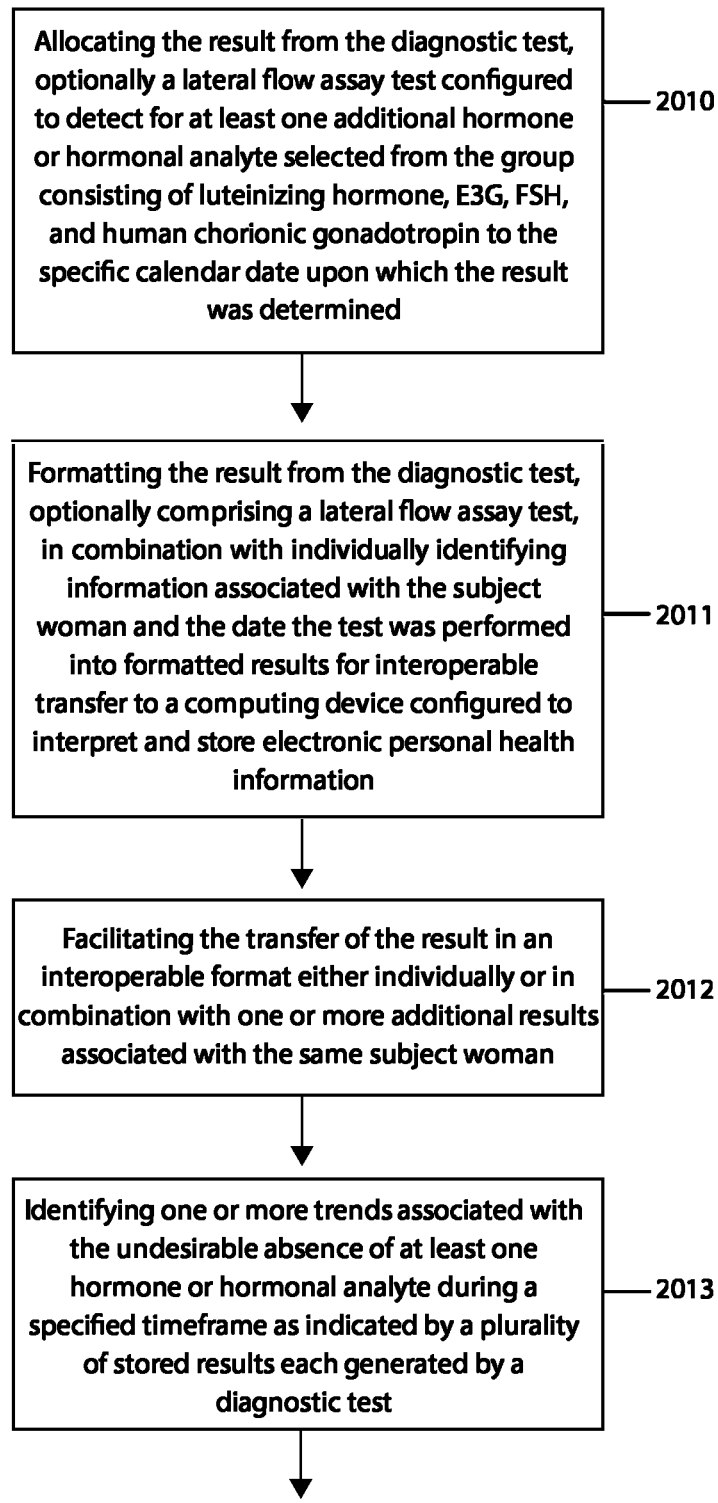
Figure 19:
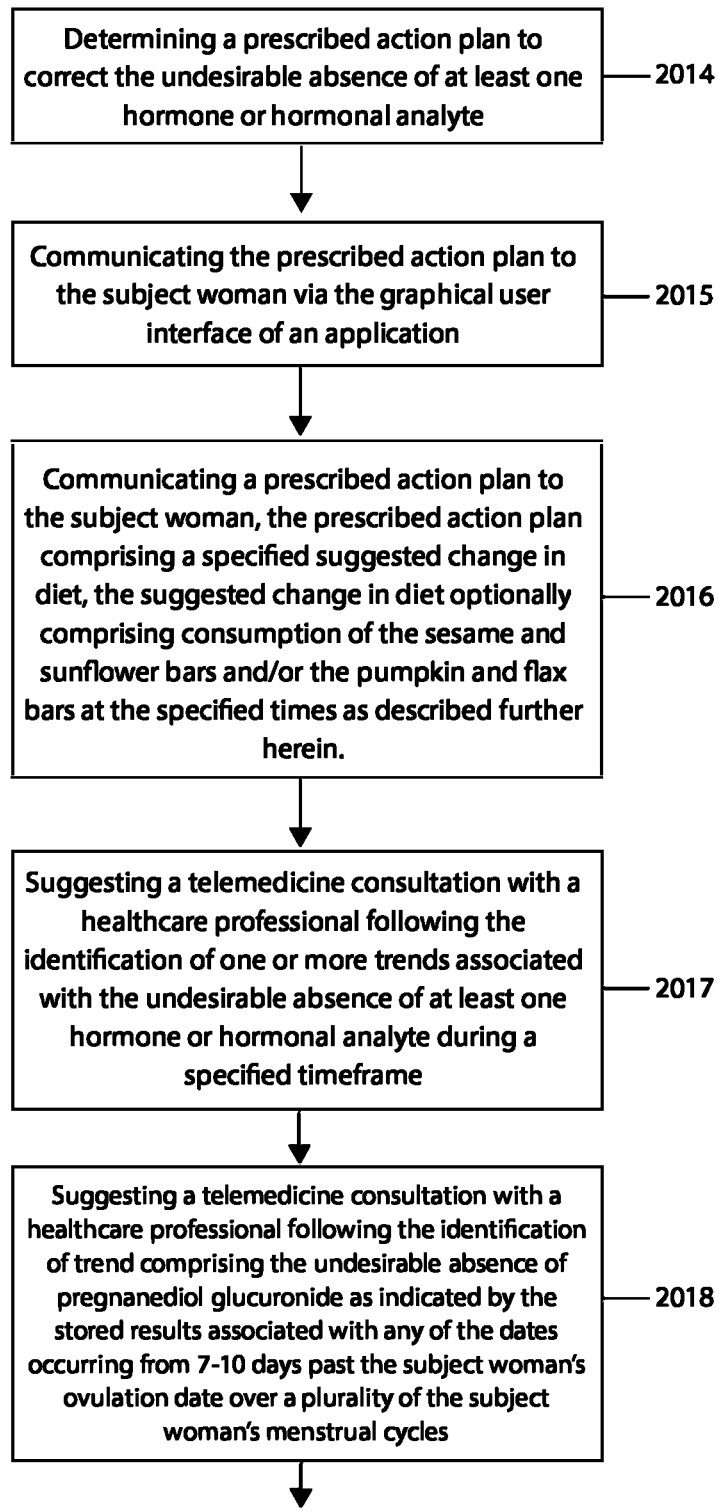
Figure 19:
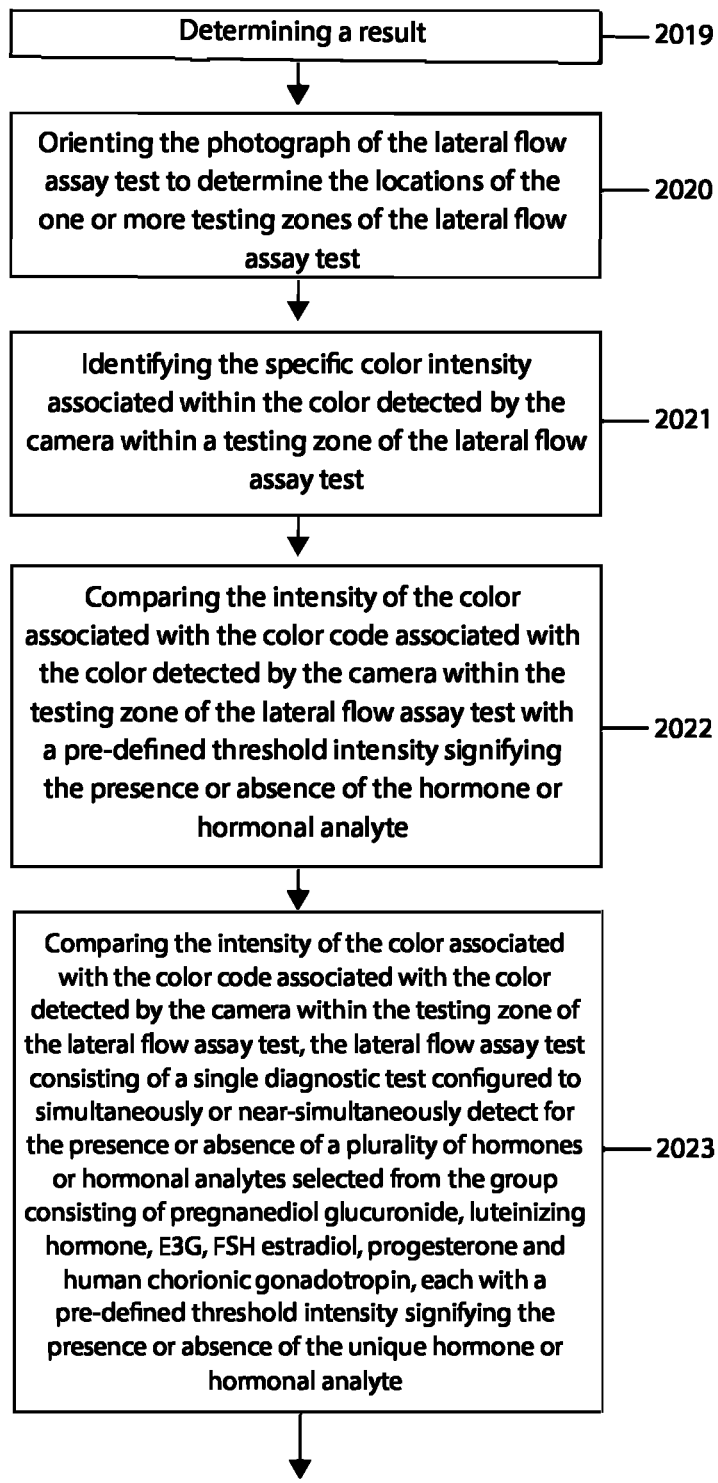
Figure 20:
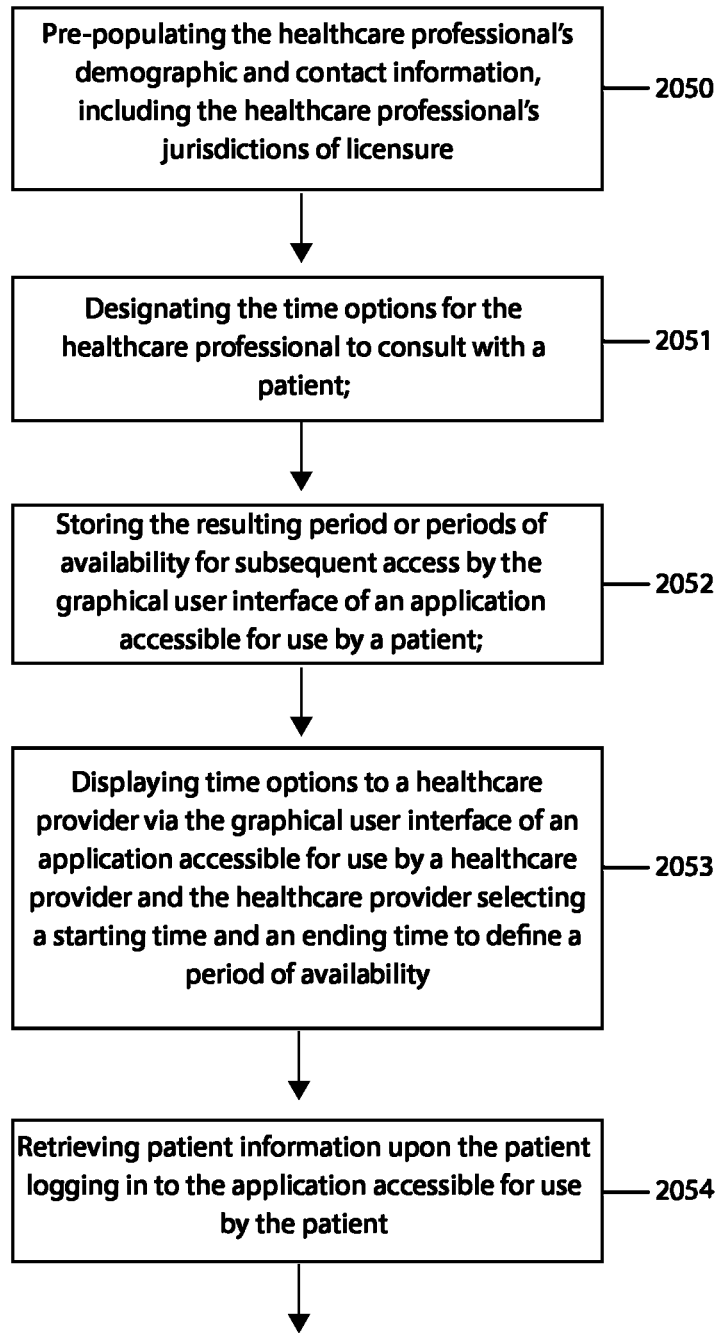
FIG. 20 depicts an exemplary method of use of the telemedicine system.
Figure 20:
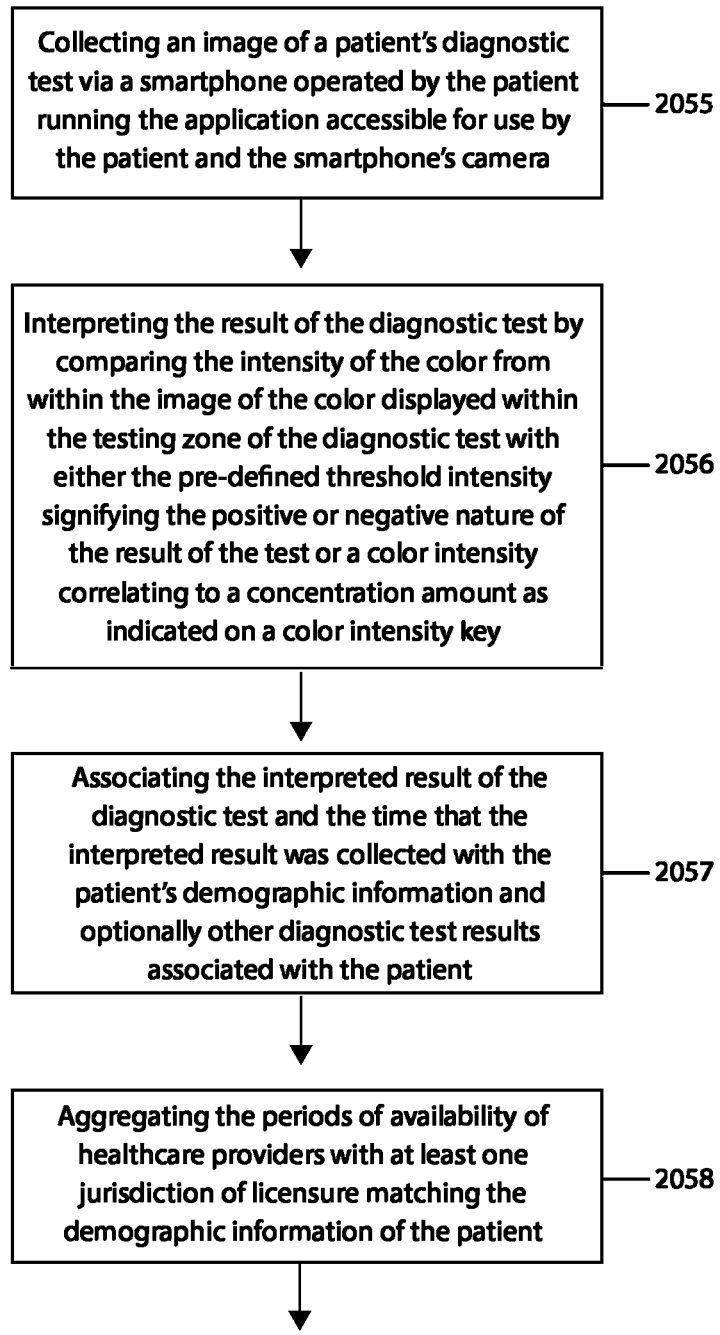
Figure 20:
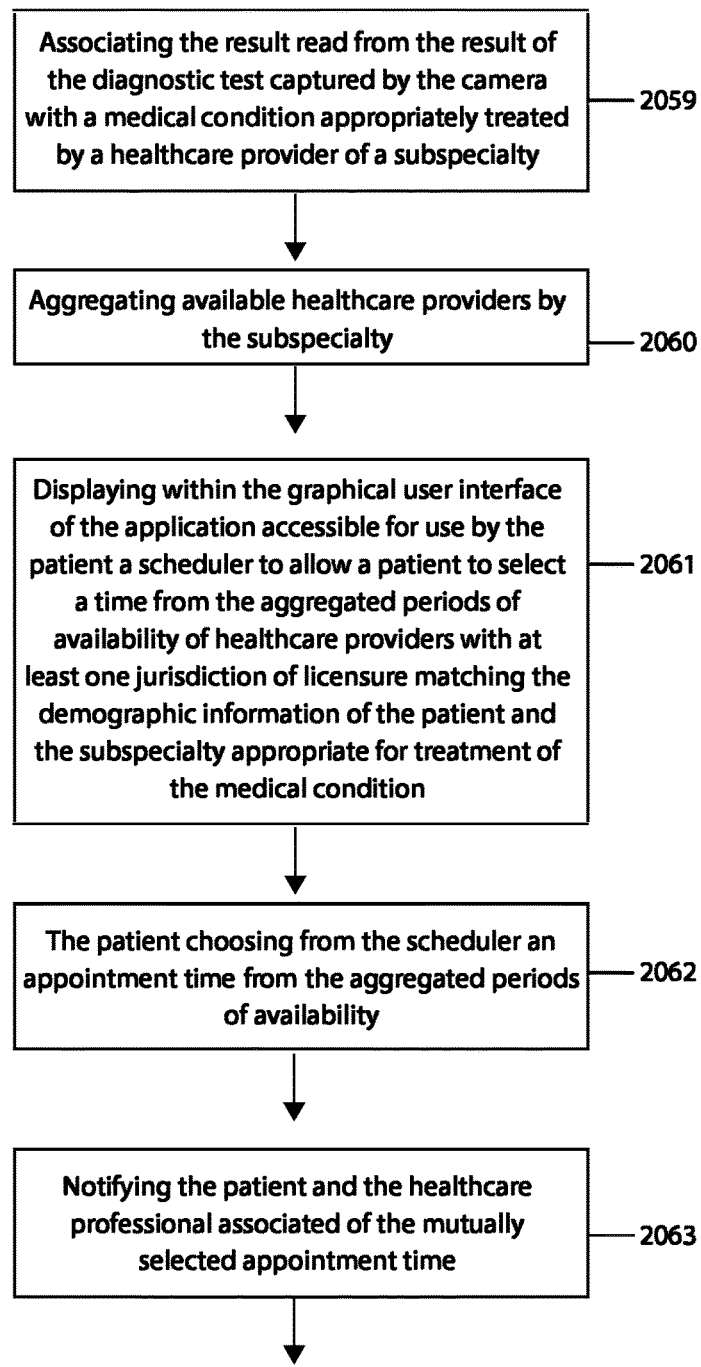
Figure 20:
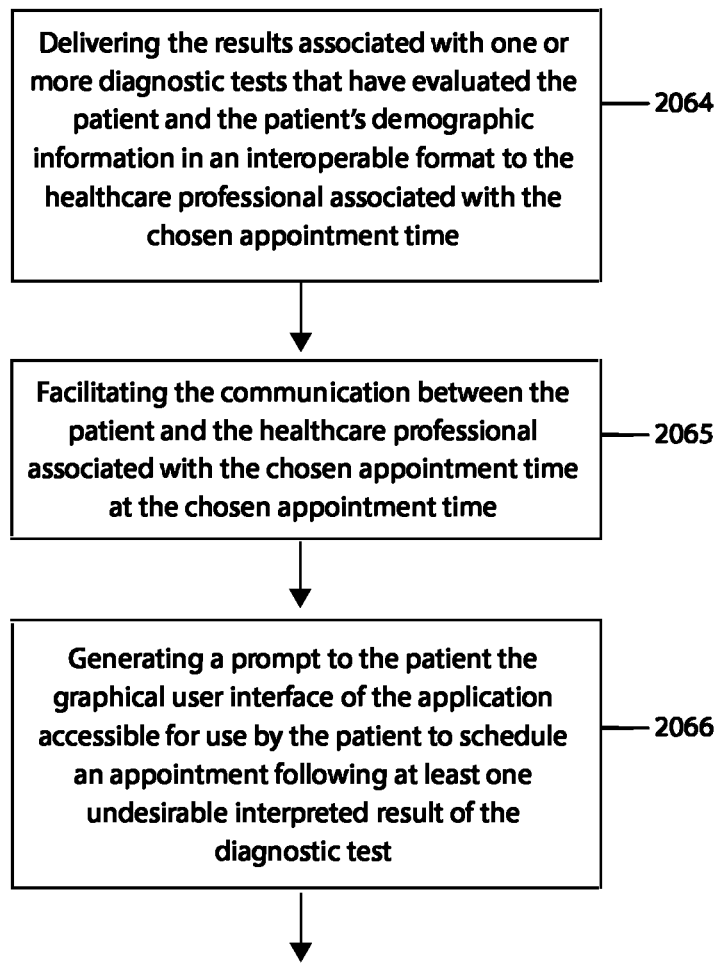
Figure 21:
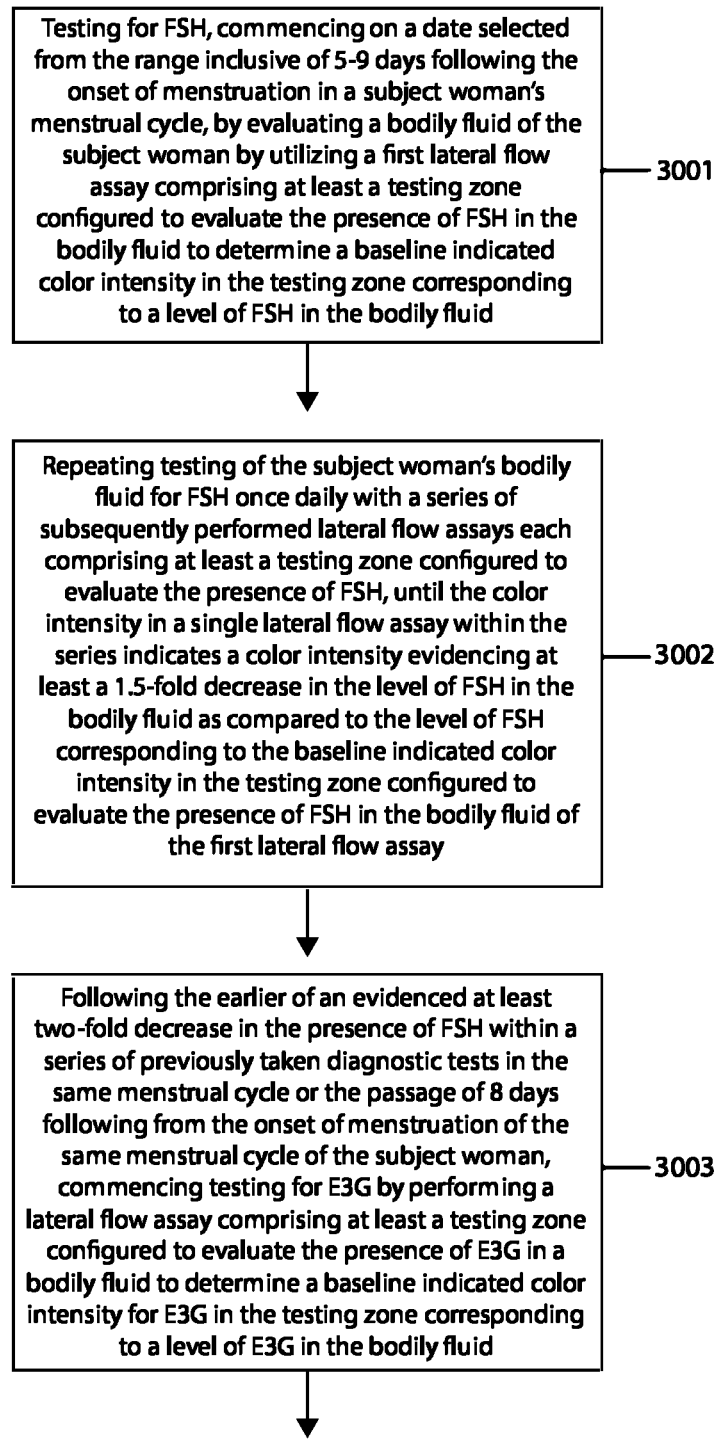
FIG. 21 depicts an exemplary method of use of the telemedicine system incorporating testing for at least FSH and E3G.
Figure 21:
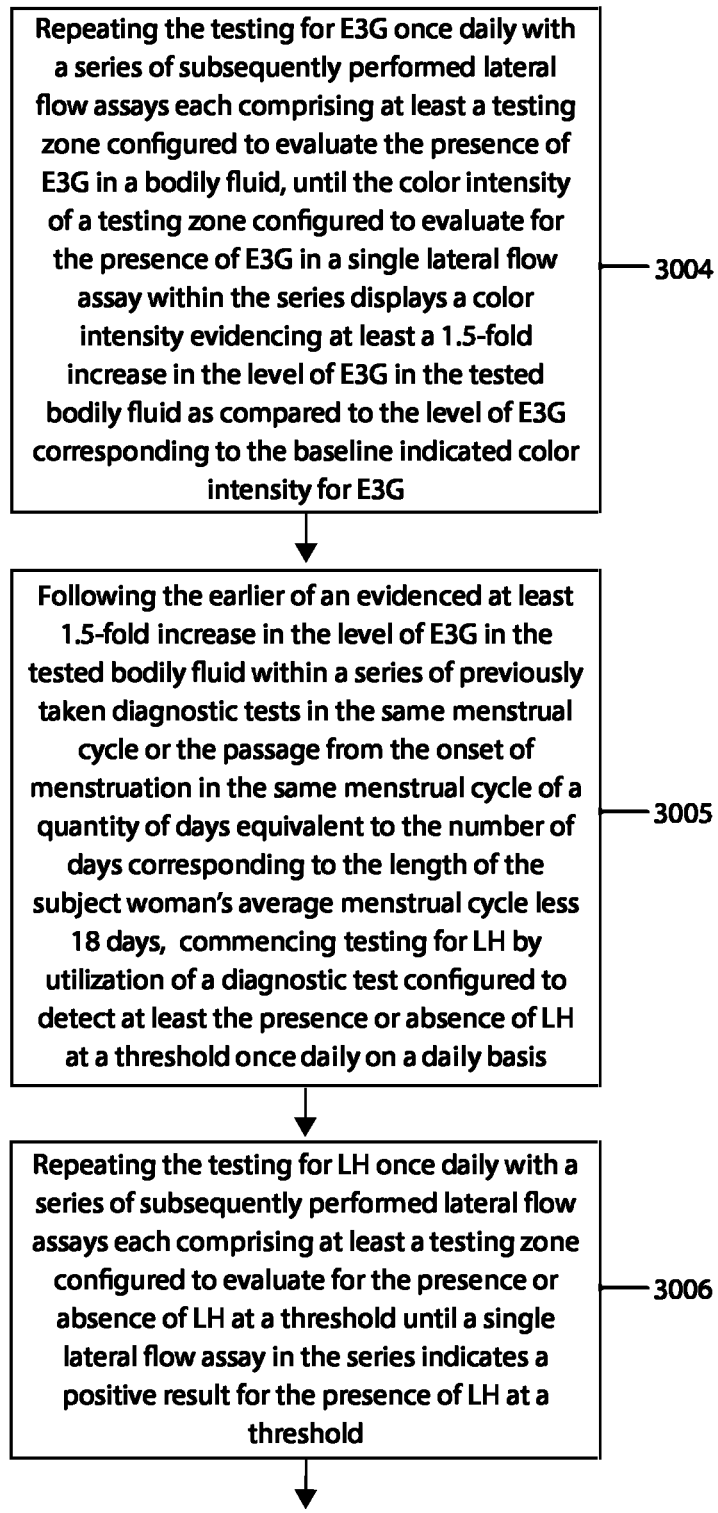
Figure 22:
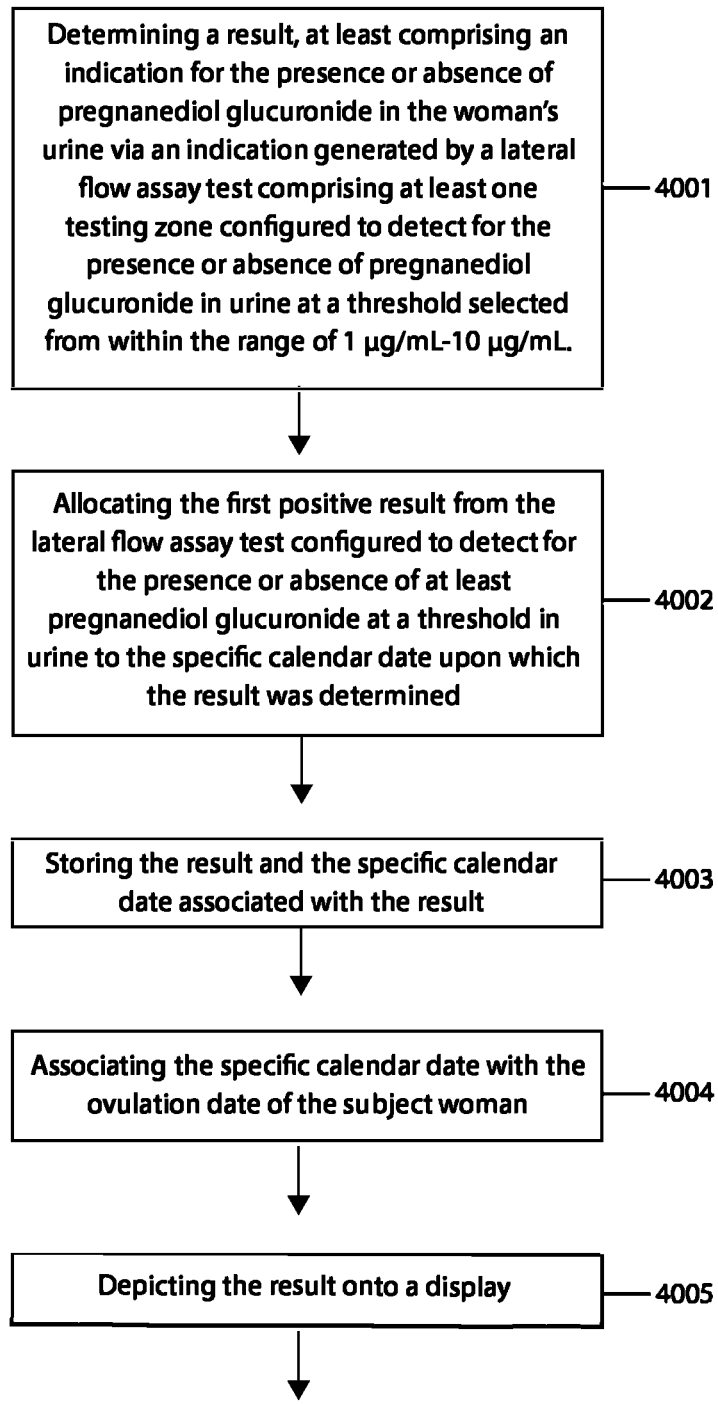
FIG. 22 depicts an exemplary method of determining a result from a lateral flow assay test, associating a date with the result, and receiving a medical consultation in association with the result.
Figure 22:
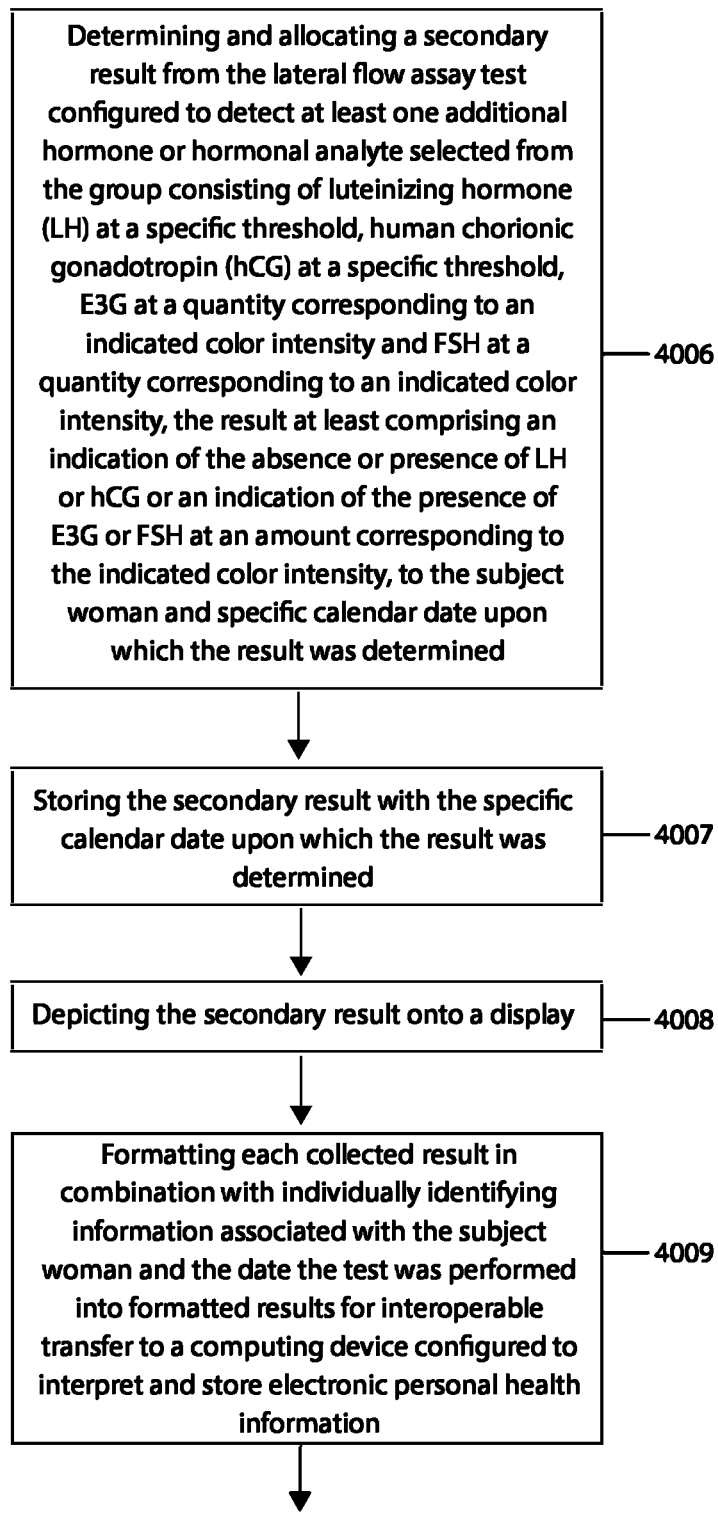
Figure 22:
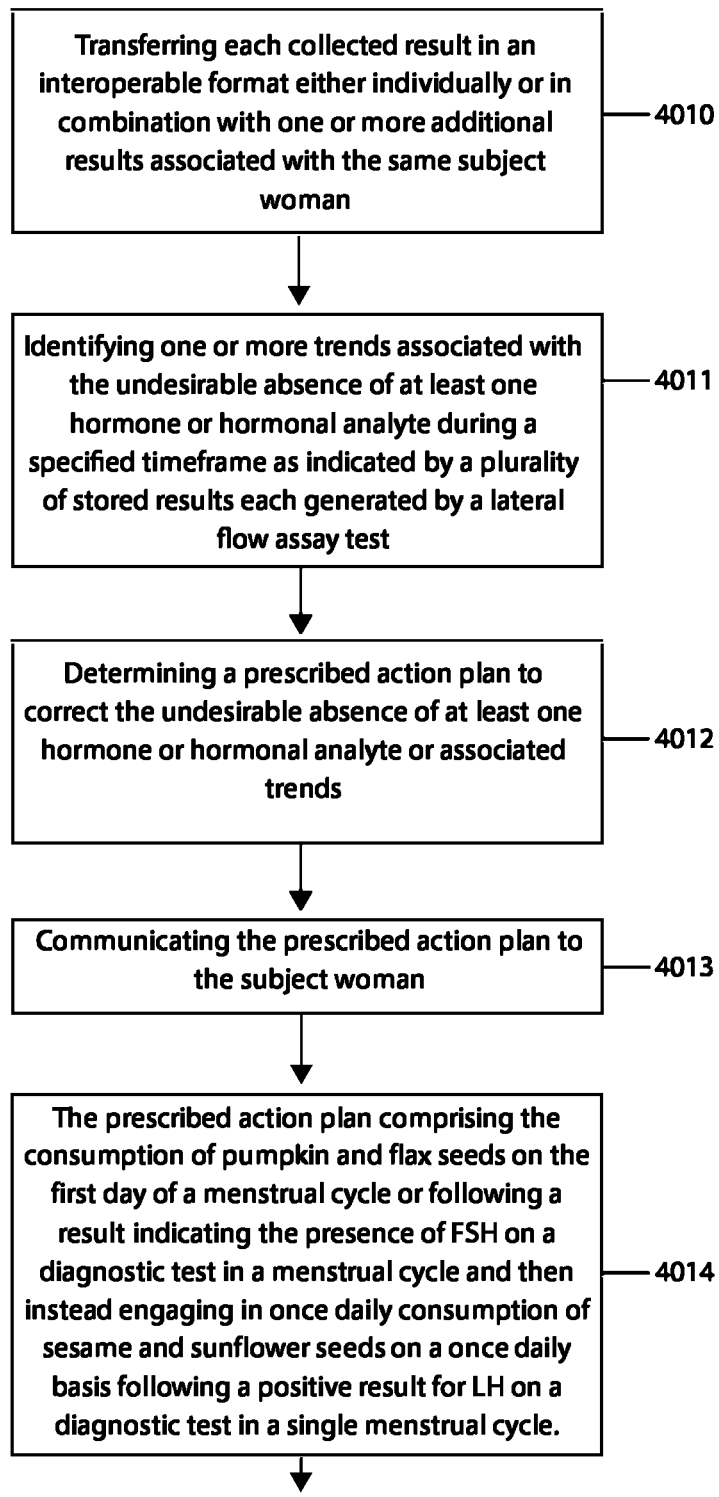
Figure 23:
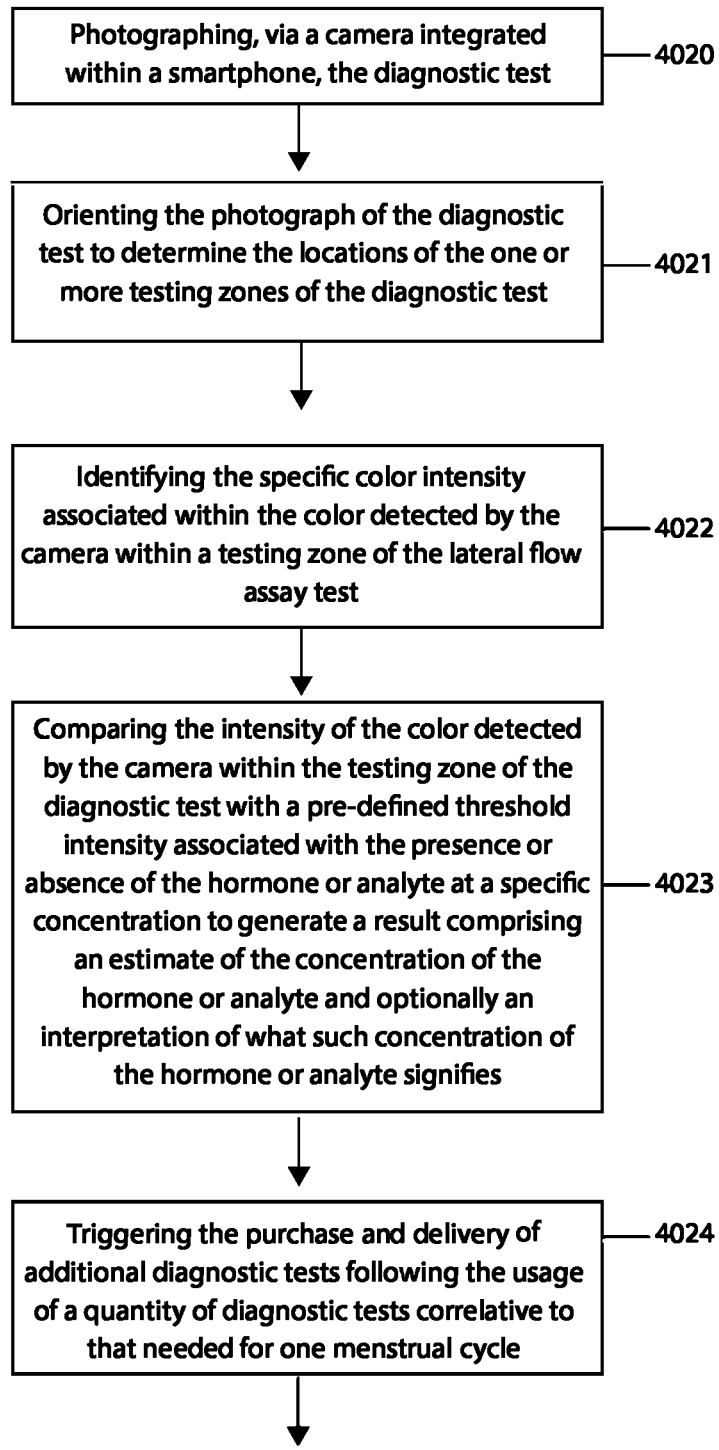
FIG. 23 depicts an exemplary method of determining results based on color intensity associated with various embodiments.
Figure 24:
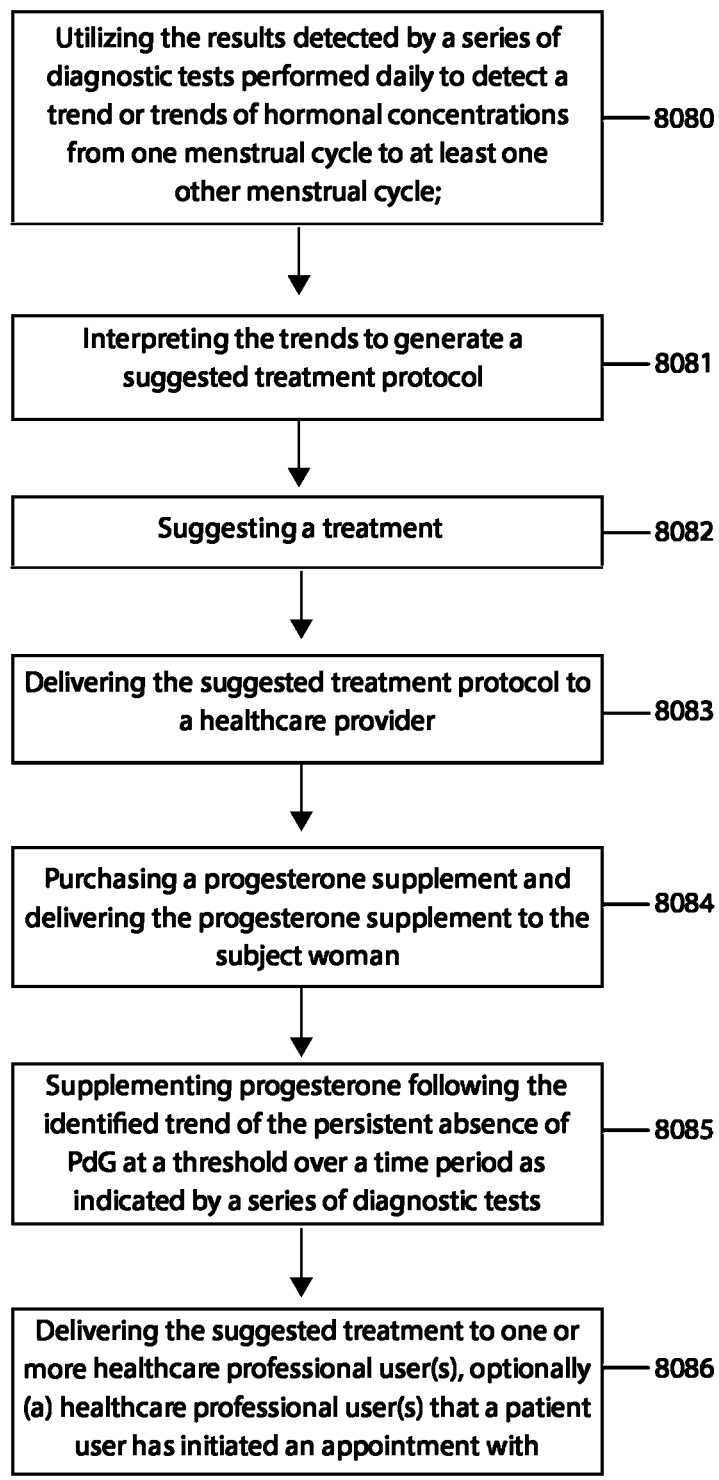
FIG. 24 depicts an exemplary method of generating an interpretation from one or more diagnostic tests associated with various embodiments.
Figure 25:
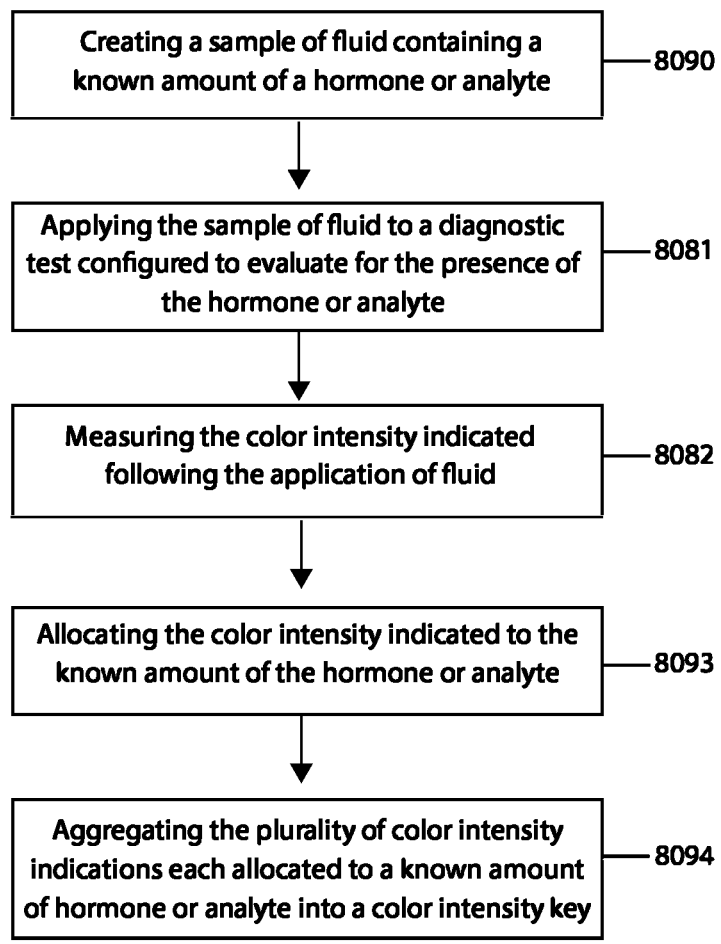
FIG. 25 depicts an exemplary method of calibrating systems configured to interpret the indication or indications of one or more diagnostic tests.
Figure 27:
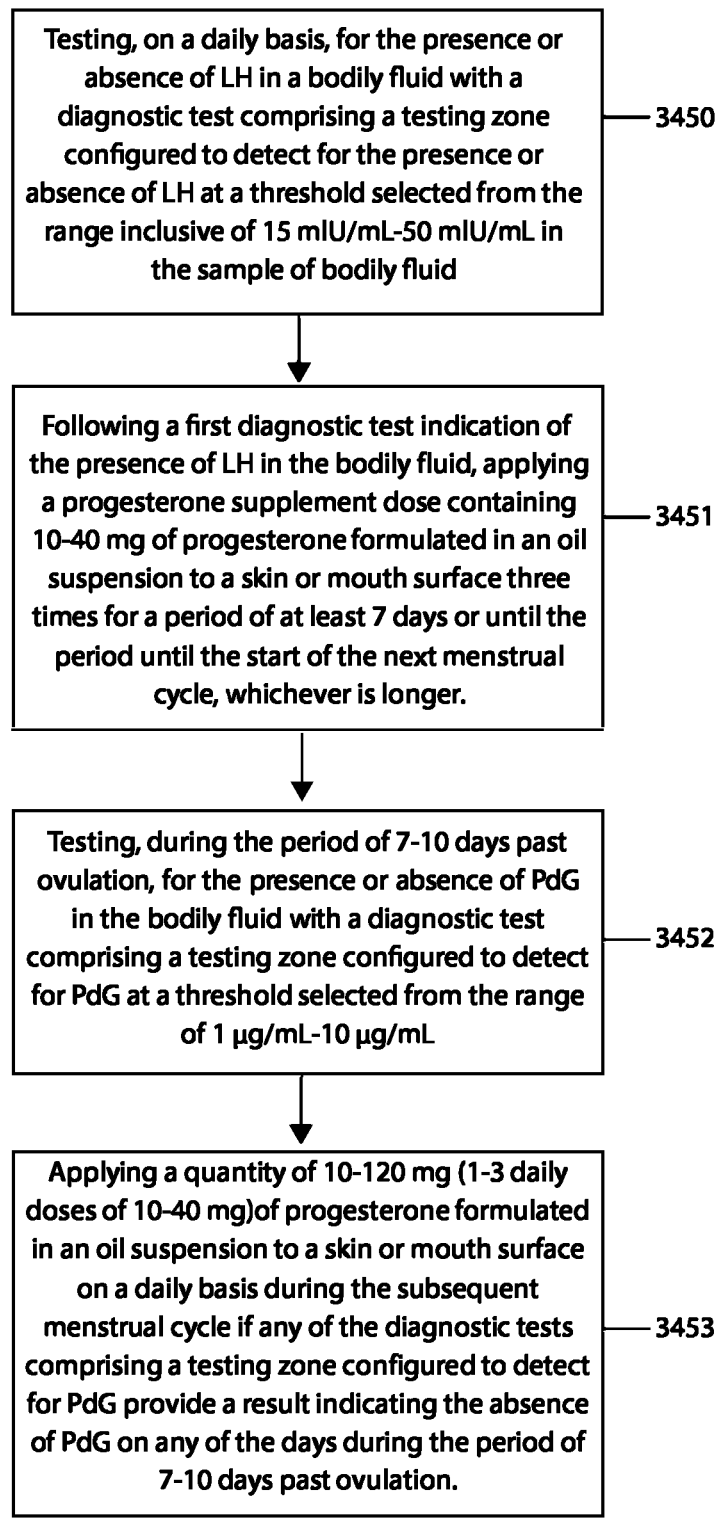
FIG. 27 depicts an exemplary method of progesterone supplementation.

Following a detected change in FSH indicated as described herein, a user is instructed, optionally via the graphical user interface, to commence utilizing a diagnostic test comprising a testing zone and corresponding result indication line configured to detect the presence of E3G once daily on a daily basis 9003. The instruction, optionally configured as a unique message 501 as described elsewhere herein, optionally is delivered to the user of an application, optionally the Patient-Facing Application, via the graphical user interface following the positive result for the presence of FSH in urine that the follicle has stimulated and/or that the fertile window has opened. In an embodiment of the invention utilizing a diagnostic test 100 comprising a plurality of testing zones and corresponding result indication lines comprising one testing zone and corresponding result indication line configured to detect for the presence or absence of E3G at a threshold and further comprising another testing zone and corresponding result indication line configured to detect for the presence or absence of FSH at a threshold, an instruction to change the type of diagnostic test 100 utilized is not necessary and therefore not included. (Instead, the steps associated with instructing a subject woman to commence utilization of a diagnostic test on a daily basis 9050 and collecting, on a daily basis the result of each diagnostic test performed 9051, as further described in FIG. 17 are repeatedly performed as an alternative). In such alternative, the preferred method embodiment incorporates a step of repeating use of the diagnostic test 100 comprising a plurality of testing zones and corresponding result indication lines, each of which is configured to detect for the presence or absence of a distinct hormone or analyte, once daily on a daily basis throughout the period of fertility testing, as switching between a different type of tests each separately configured to detect for a different subset of hormones and/or analytes becomes unnecessary in such example. In various method embodiments, following the first indication demonstrating the presence of FSH at a threshold on a diagnostic test 100, a unique message 501 is delivered to the user of the system via the graphical user interface that the follicle has stimulated and/or that the fertile period of the subject woman's menstrual cycle has begun.

In an exemplary implementation, it is a further teaching to perform the step of recording and evaluating the results of the testing for FSH collected from a diagnostic test 100 performed daily, and any results from any subsequently performed diagnostic tests configured to evaluate additional hormones and/or analytes in an applied bodily fluid, optionally in association with other components of the system as described herein. As depicted by FIG. 17 in association with an exemplary embodiment and elsewhere herein, the method further comprises the step of generating an interpretation following the evaluation of a result of each diagnostic test 100, the interpretation based on the specific indicated result 9051-9055. Following each of the generating an interpretation steps 9051-9055, the method further comprises the step of formatting each interpretation into a unique message 501 and depicting the unique message 501 onto a display 605.

Following a change in FSH as indicated by a diagnostic test 100 subsequent to at least one previously positive diagnostic test for FSH in the same menstrual cycle—optionally a 1.5 fold decrease in FSH levels, and optionally detected by an application, processor, computing device and/or camera as described elsewhere herein—a user is instructed, optionally via the graphical user interface, to commence utilizing a diagnostic test 100 comprising a testing zone and corresponding result indication line configured to detect and provide an indication correlating to a color intensity for the presence of E3G once daily on a daily basis 9003, the color intensity optionally indicating an amount of E3G in association with a color intensity key 800 and/or a Diagnostic Test Key 200. In an alternative embodiment, the change is indicated by a result on a diagnostic test 100 configured to detect FSH in urine demonstrating a level indicated above a threshold followed by a result on a diagnostic test configured to detect FSH in urine demonstrating an indicated level of FSH below a threshold. In an example, the change in FSH is determined by photographing a diagnostic test 100 comprising at least one testing zone and a corresponding result indication line configured to evaluate for the presence of FSH in the bodily fluid to determine a baseline indicated color intensity, optionally corresponding to a specific RGB or HEX color code, in such testing zone on a date 2-7 days from the onset of menstruation. In an embodiment, an application and/or computing device is preconfigured with color intensities, optionally derived from a color intensity key 800, of such result indication line corresponding to different levels of FSH in an applied fluid, for instance by recording the results for the color intensities occurring in each of a plurality of diagnostic tests each applied with fluid containing a known amount of FSH. In an example, the applied fluid consists of male urine spiked with a known level of FSH. In various embodiments where the color intensity associated with results of a diagnostic test 100 does not precisely match a previously known correlation to an amount of a hormone or analyte (such as FSH or E3G) in urine, the estimated amount is instead determined by substituting the closest color intensity included in the color intensity key 800 to the indicated color intensity and estimating the level of the amount of hormone or analyte in the applied fluid to be that associated with the closest color intensity. In such manner, the present inventor has recognized that it is possible to determine fold changes in FSH in an applied fluid, for example a twofold decrease, evidenced by one diagnostic test as compared to a previously taken diagnostic test as a baseline, by correlating color intensities indicated on a diagnostic test to a known level of FSH and ensuring that in methods of use that each diagnostic test utilized in association with the relevant method is similarly configured. Similar mechanisms are useful in correlating color intensities with the levels in an applied bodily fluid of other hormones and/or analytes, such as E3G. Such correlated color intensities are useful in an embodiment comprising a Diagnostic Test Key 200 as described elsewhere herein. It is important to note in association with teachings of the invention that a certain fold decrease in the color intensity indicated over a series of diagnostic tests does not necessarily equate to a similar fold decrease or increase in the actual relevant amount of hormone or analyte in an applied sample. Notably, the present inventor has determined that some diagnostic tests configured with certain carrier proteins are difficult to consistently reproduce, and has also noted that the precision associated with manufacturing consistently reproduced diagnostic tests is important in the effective deployment of such method.

In an embodiment of the invention utilizing a diagnostic test comprising a plurality of testing zones comprising one testing zone configured to detect for the presence or absence of E3G at a threshold and further comprising another testing zone configured to detect for the presence or absence of FSH at a threshold, an instruction to change the type of diagnostic test utilized is not necessary and therefore not provided, as in the method depicted by FIG. 17. In such alternative, it is advantageous instead to instruct the user to simply repeat use of an identically configured diagnostic test 100 comprising a plurality of testing zones, each of which is configured to detect for the presence or absence of a distinct hormone or analyte, once daily on a daily basis throughout the period of fertility testing. In an embodiment, following the first indication demonstrating the presence of FSH at a threshold on a diagnostic test, a message is delivered to the user of the system via the graphical user interface that the follicle has stimulated and/or that the fertile window has opened.

In various embodiments the length of the menstrual cycle is determined as the duration between the onset of menstruation in a first menstrual cycle and the onset of menstruation in the subsequent menstrual cycle. An average menstrual cycle length can be calculated by looking back at a number of recent menstrual cycles, optionally 6 menstrual cycles, and determining the average in accordance with basic mathematical principles. In various embodiments, the average length may be entered via the application or otherwise via the graphical user interface of a computing device to assist in the determination of the dates for when testing for various hormones should change. It is a teaching of a method embodiment that to determine the day upon which testing for FSH should be replaced or augmented with testing for E3G, an application is configurable to subtract 21 from the average length of a subject woman's menstrual cycle to arrive at an approximated length of time from the onset of menstruation in a single menstrual cycle until the detectible presence of E3G in tested urine, which could be used as a backup timeframe to change use of diagnostic tests configured to detect only one particular hormone or analyte on a daily repeating basis, if a 1.5 fold decrease in FSH is not detected over a series of diagnostic tests within such an approximated timeframe. In an embodiment, in a case where a 1.5 fold decrease in FSH is not observed on any of a series of diagnostic tests performed on a subject woman's bodily fluid within a single menstrual cycle, a message is delivered via the graphical user interface or otherwise to a display stating that ovulation is likely not to occur this cycle. In an embodiment, in a case where a 1.5 fold decrease in FSH is not observed on any of a series of diagnostic tests performed on a subject woman's bodily fluid within a single menstrual cycle, optionally only if the woman is above a certain age (in an example, 35 years old) a message is delivered via the graphical user interface or otherwise to a display suggesting a likelihood that menopause has started. In an embodiment, whereby the system and/or the user has detected three or more consecutive non-ovulatory cycles and the user is below a certain age (in an example, 35 years old), a message is delivered via the graphical user interface or otherwise to a display suggesting a likelihood that the woman is experiencing PCOS or another medical condition and that it would be appropriate to discuss with a physician. In an embodiment, whereby the system and/or the user has three or more consecutive non-ovulatory cycles and the user is above a certain age (in an example, 35 years old), a message is delivered via the graphical user interface or otherwise to a display suggesting a likelihood that menopause has started. In an embodiment, where a 1.5 fold decrease in FSH is observed on any diagnostic test within a series of diagnostic tests performed on a subject woman's bodily fluid within a single menstrual cycle, a message is delivered via the graphical user interface or otherwise to a display suggesting that a follicle has been selected and/or that the subject woman's fertile window has opened. The present inventor has recognized that such information is useful to a subject woman in association with maximizing her chances for conception during a specific menstrual cycle.

Steps associated with use of the Fertility Tracking System and other embodiments of the invention, in accordance with the descriptions herein, include the following:

Allocating the result from the lateral flow assay test configured to detect for the presence or absence of at least pregnanediol glucuronide in urine to the specific calendar date upon which the result was determined 4002. Such step optionally takes place in accordance with or by otherwise utilizing the calendar and/or an application, optionally the Patient-Facing Application, as described elsewhere herein.

Storing the result and the calendar date associated with the result 4003. Such step optionally takes place in accordance with or by otherwise utilizing the calendar and/or the application as described elsewhere herein.

Associating and storing a specific calendar date with the ovulation date of the subject woman 4004. In an example, the subject woman may manually input her ovulation date. In various embodiments, the ovulation date is estimated in accordance with the teachings elsewhere herein. Such step optionally takes place in accordance with or by otherwise utilizing the calendar and/or the application as described elsewhere herein.

Depicting the result onto a display 4005. Such step optionally takes place in accordance with or by otherwise utilizing the calendar and/or the application as described elsewhere herein. In one example, the display 605 is configured as depicted in an exemplary embodiment by FIG. 10b or FIG. 10d.

Determining a secondary result from a lateral flow assay test comprising for the presence or absence of at least one additional hormone or hormone metabolite selected from the group consisting of lutenizing hormone, estrogen, and human chorionic gonadotropin, each at a specific threshold.

Allocating the secondary result from the lateral flow assay test configured to detect at least one additional hormone or hormonal analyte selected from the group consisting of lutenizing hormone (LH) at a specific threshold, human chorionic gonadotropin (hCG) at a specific threshold, E3G at a quantity corresponding to an indicated color intensity and FSH at a quantity corresponding to an indicated color intensity, the result at least comprising an indication of the absence or presence of LH or hCG or an indication of the presence of E3G or FSH at an amount corresponding to the indicated color intensity, to the specific calendar date upon which the result was determined 4006. Such a lateral flow assay optionally takes the form of the diagnostic test(s), and operates in coordination with the color intensity key 800 and other components as described elsewhere herein.

Associating and storing a specific calendar date with the results of a lateral flow assay and/or the ovulation date of the subject woman 4007. Such step optionally takes place in accordance with or by otherwise utilizing the calendar, graphical user interface and/or the application as described elsewhere herein.

Depicting the results onto a display 4008. Such step optionally takes place in accordance with the display 605 depicted by FIG. 10b or FIG. 10d, the graphical user interface and/or by utilizing the calendar and/or the application as described elsewhere herein.

Formatting each result from the lateral flow assay test in combination with individually identifying information associated with the subject woman and the date the test was performed into formatted results for interoperable transfer to a computing device configured to interpret and store electronic personal health information 4009. Such step optionally takes place in accordance with or by otherwise utilizing an application, optionally the Patient-Facing Application, as described elsewhere herein.

Transferring each collected result in an interoperable format either individually or in combination with one or more additional results associated with the same subject woman 4010. Such step optionally takes place in accordance with or by otherwise utilizing the Patient-Facing Application, the Healthcare Professional-Facing Application and/or the Telemedicine System as described elsewhere herein.

Identifying one or more trends associated with the undesirable absence of at least one hormone or hormonal analyte during a specified timeframe as indicated by a plurality of stored results each generated by a lateral flow assay test 4011. Such step optionally takes place in accordance with or by otherwise utilizing the Fertility Tracking System as described elsewhere herein.

Determining a prescribed action plan to correct the undesirable absence of at least one hormone or hormonal analyte or associated trends 4012. Such step optionally takes place in accordance with or by otherwise utilizing the Seed Consumption System as described elsewhere herein.

Communicating the prescribed action plan to the subject woman 4013. Such step optionally takes place in accordance with or by otherwise utilizing an application, optionally the Patient-Facing Application, as described elsewhere herein. Optionally, the prescribed action plan comprises a specified suggested change in diet, specifically commencing the consumption of certain seeds or products containing portions of the certain seeds, optionally the once daily consumption of pumpkin seeds optionally in the amount of 1 tablespoon and flax seeds optionally in the amount of 1 tablespoon, and optionally in snack bar form, once daily upon the start of menstruation, or optionally once daily following the first indication in a single menstrual cycle for the presence of FSH on a diagnostic test 100 performed on the subject woman's urine, and then subsequently changing to instead engage in daily consumption of sesame seeds optionally in the amount of 1 tablespoon and sunflower seeds optionally in the amount of 1 tablespoon, and optionally in snack bar form, following the first indication of a positive LH result on a diagnostic test 100 performed on the subject woman's urine, or optionally in accordance with or by otherwise utilizing the Seed Consumption System as described elsewhere herein.

Suggesting a telemedicine consultation with a healthcare professional following the identification of one or more trends associated with the undesirable absence of at least one hormone or hormonal analyte as indicated on one or more appropriately configured diagnostic test(s) during a specified timeframe 4015. Such step optionally takes place in accordance with or by otherwise utilizing the Telemedicine System as described elsewhere herein. The one or more such trends may consist of the undesirable absence of pregnanediol glucuronide as indicated by the stored results as indicated on one or more appropriately configured diagnostic test(s) associated with any of the dates occurring from 7-10 days past the subject woman's ovulation date. Such step optionally takes place in accordance with or by otherwise utilizing the Fertility Testing System as described elsewhere herein.

The determining a result step takes place in various embodiments by photographing, via a camera integrated within a smart phone, the diagnostic test 4020. Such step optionally takes place in accordance with or by otherwise utilizing the application, camera and/or smart phone as described elsewhere herein.

Orienting the photograph of the diagnostic test to determine the locations of the one or more result indication lines of the diagnostic test 4021, optionally by first identifying the end of the diagnostic test 100 and aligning it with a graphical user interface element. Such step optionally takes place in accordance with or by otherwise utilizing the camera and smart phone 600 as described elsewhere herein.

Identifying the specific color intensity, optionally a specific color intensity correlating to a specific level of analyte and/or hormone as described elsewhere herein, associated within the color detected by the camera within a result indication line of the lateral flow assay test 4022. Such step optionally takes place in accordance with or by otherwise utilizing the Fertility Testing System as described elsewhere herein.

Comparing the intensity of the color detected by the camera within the result indication line of the diagnostic test 100 with a pre-defined threshold intensity, optionally in association with a color intensity key 800, associated with the presence or absence of the hormone or analyte at a specific concentration to generate a result comprising an estimate of the concentration of the hormone or analyte and optionally an interpretation of what such concentration of the hormone or analyte signifies 4023, as further described elsewhere herein. Such step optionally takes place in accordance with or by otherwise utilizing the Fertility Testing System as described elsewhere herein.

The diagnostic test comprising a lateral flow assay test may consist of a single test, such as the diagnostic test as described elsewhere herein, configured to simultaneously or near-simultaneously detect for the presence or absence of a plurality of hormones or hormonal analytes selected from the group consisting of pregnanediol glucuronide, luteinizing hormone, estrogen, estradiol, progesterone and human chorionic gonadotropin. The method may further comprise triggering a delivery of additional lateral flow assay tests following the usage of a quantity of lateral flow assay tests correlative to one menstrual cycle 4024. Such step optionally takes place in accordance with or by otherwise utilizing the Fertility Testing System as described elsewhere herein.

In an example the method further comprises depicting the results and/or interpretations onto a display, optionally via a graphical user interface, featuring a calendar 5000 with the result of each test displayed on in association with the date each diagnostic test 100 was performed within the displayed calendar. Such step optionally takes place in accordance with or by otherwise utilizing the calendar and graphical user interface as described elsewhere herein. In various examples, the results are displayed via a positivity scale 5685 as described elsewhere herein.

The fertility tracking system in certain configurations is more precisely described as a "predicting fertile window system." The present inventor has recognized that aspects of the invention described herein provide unique benefits to persons wishing to enhance the likelihood of conception by more clearly identifying the opening date and closing date of the fertile window, as indicated by the presence of certain hormones and analytes in urine. In one example, the system is configured to provide prompts via the graphical user interface not only signaling that a certain hormone is present or absent in a sample evaluated with a diagnostic test as described herein, but also an interpretation of the relevance of that hormone or analyte to the certain user. For instance, in a configuration intended to assist a woman to become pregnant, the detection of E3G or FSH in urine at a threshold in association with the utilization of an appropriately configured diagnostic test as described herein may prompt the system to display a message indicating that the subject woman's fertile period has begun and that she should engage in intercourse to achieve pregnancy.

In an example, diagnostic tests configured to detect for the presence or absence of hCG at a threshold, optionally in association with the detection of other hormones in a single test, are utilized in association with the predicting fertile window system. In such diagnostic tests, a result indicating the presence of hCG at a threshold indicates pregnancy. Likewise in such diagnostic tests, a result indicating the absence of hCG at a threshold indicates that the subject woman is not pregnant. Therefore, in an example, following such result, a message is displayed in the graphical user interface that pregnancy has been achieved and that the woman can optionally cease testing, or continue testing especially for PdG on an ongoing basis to ensure that the woman's progesterone levels remain sufficient to support a pregnancy (as indicated by a positive PdG result on a diagnostic test as described herein). In a situation where a diagnostic test indicates a positive result for hCG at a threshold in a tested bodily fluid and testing of the same sample of bodily fluid indicates a result of the absence of PdG at a threshold, an interpretation comprising an indication that the subject woman has likely not produced enough progesterone to sustain pregnancy. Likewise, in a situation where a diagnostic test indicates a positive result for hCG at a threshold in a tested bodily fluid and testing of the same sample of bodily fluid indicates a result of the presence of PdG at a threshold, an interpretation comprising an indication that the subject woman has likely produced enough progesterone to sustain pregnancy. In various embodiments messages intended to convey the above results and/or interpretations are delivered via components of the system as described elsewhere herein.

In an embodiment, the system described herein is configured as a system to predict the fertile window of a patient user. In one aspect, the system may be configured for use with both diagnostic tests configured to detect for the presence or absence of PdG at a threshold in urine and separately diagnostic tests configured to detect for the presence or absence of LH at a threshold in urine. In another aspect, the system may be configured for use with diagnostic tests configured to detect for at least both the presence or absence of PdG at a threshold in urine and for the presence or absence of LH at a threshold in urine within a single diagnostic test. In accordance with the predicting fertile window system, it may be advantageous for the user to perform the diagnostic test at least once daily throughout the course of the menstrual cycle.

Likewise, the present inventor has recognized that aspects of the invention described herein provide unique benefits to persons wishing to avoid conception and avoid pregnancy by more clearly identifying especially the closing date of the fertile window. In an embodiment, the system described herein is configured as a system to allow a patient user to avoid pregnancy. In such embodiment, the present inventor has identified a context for use of the system as a form of birth control. In one example, the system is configured to provide prompts via the graphical user interface not only signaling that PdG is present at a threshold correlating to ovulation in a sample evaluated with a diagnostic test as described herein, but also an interpretation of the relevance of the presence of PdG in the sample to a user, namely that she has ovulated and that her infertile period has begun or that she may engage in sexual intercourse without the risk of becoming pregnant. Thus, it is a teaching of an example of the invention to confirm ovulation, which is applied as an aid to the avoidance of unwanted pregnancy.

It is a teaching in association with the associated applications, and in one embodiment, the predicting fertile window system, to trigger the recurring purchase and delivery of a quantity of diagnostic tests configured to detect both the absence or presence of PdG at a threshold and the presence or absence of LH at a threshold in urine following a period correlating to a woman's menstrual cycle, optionally via Amazon, and optionally as a component of the Patient-Facing Application. The present inventor has recognized that the system configured to trigger such purchase and delivery on a recurring basis provides value especially to women who wish to avoid pregnancy by ensuring a supply of the diagnostic tests as further described herein needed for utilization in association with teachings of the system.

The invention, including its methods of use, disclosed herein may comprise one or more steps or actions for achieving the described method. The method steps and/or actions may be interchanged with one another without departing from the scope of the claims. The order and/or use of specific steps and/or actions may be modified without departing from the scope of the claims.

Skilled artisans will appreciate that elements in the figures are illustrated for simplicity and clarity and have not necessarily been drawn to scale. For example, the dimensions of some of the elements in the figures may be exaggerated relative to other elements to help improve understanding of various embodiments. In addition, the description and drawings do not necessarily require the order illustrated. It will be further appreciated that certain actions and/or steps may be described or depicted in a particular order of occurrence while those skilled in the art will understand that such specificity with respect to sequence is not actually required.

Apparatus and method components have been represented where appropriate by conventional symbols in the drawings, showing only those specific details that are pertinent to understanding the various embodiments so as not to obscure the disclosure with details that will be readily apparent to those of ordinary skill in the art having the benefit of the description herein. Thus, it will be appreciated that for simplicity and clarity of illustration, common and well-understood elements that are useful or necessary in a commercially feasible embodiment may not be depicted in order to facilitate a less obstructed view of these various embodiments.

In the foregoing specification, specific embodiments have been described. However, one of ordinary skill in the art appreciates that various modifications and changes can be made without departing from the scope of the disclosure as set forth in the claims to follow in a subsequent disclosure. Accordingly, the specification and figures are to be regarded in an illustrative rather than a restrictive sense, and all such modifications are intended to be included within the scope of present teachings. To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

The benefits, advantages, solutions to problems, and any element(s) that may cause any benefit, advantage, or solution to occur or become more pronounced are not to be construed as a critical, required, or essential features or elements of any or all subsequent claims.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The terms "coupled," "connected" and "linked" as used herein is defined as connected, although not necessarily directly and not necessarily mechanically. A device or structure that is "configured" in a certain way is configured in at least that way, but may also be configured in ways that are not listed. Also, the sequence of steps in a flow diagram or elements in the claims, even when preceded by a letter does not imply or require that sequence. Any noun in the singular is also intended to encompass the noun in the plural and vice versa, unless specifically stated as otherwise intended. Any pronoun or other identifier in the female form is also intended to encompass the pronoun or other identifier in the male form and vice versa, unless specifically stated as otherwise intended.

While the foregoing is directed to aspects of the present disclosure, other and further aspects of the disclosure may be devised without departing from the basic scope thereof.

This invention was made with United States Government support under Agreement No. FA8649-20-9-9107, awarded by the United States Government. The United States Government has certain rights in the invention.

I claim:

1. A fertility tracking system for evaluating a menstrual cycle, comprising:
   a plurality of diagnostic tests, wherein each diagnostic test comprises:
      a sample pad configured to collect an applied sample,
      a conjugate pad comprising one or more antibodies conjugated with one or more visual labels,
      one or more testing zones, positioned downstream from the one or more antibodies, wherein each testing zone is configured to evaluate the applied sample for the presence or absence of one or more hormones and/or analytes by binding to the one or more antibodies in a sandwich or competitive assay format, as indicated by the presence or absence of the one or more visual labels at one or more result indication lines in each testing zone after the applied sample has passed through each testing zone, wherein at least one of the plurality of diagnostic tests is configured to evaluate for the presence or absence of pregnanediol glucuronide (PdG) at a threshold selected from 3 µg/mL-20 µg/mL in an applied fluid, and wherein said diagnostic test for evaluating for PdG comprises monoclonal anti-PdG antibodies of an isotype selected from the group consisting of IgG1, IgG1 Kappa, IgG2a, IgG2b, and/or the IgG2c isotype;

at least one of the plurality of diagnostic tests is configured to evaluate for the presence or absence of luteinizing hormone (LH) at a threshold selected from 15 mIU/mL-50 mIU/mL, and wherein said diagnostic test for evaluating for LH comprises anti-LH antibodies, and at least one of the plurality of diagnostic tests is configured to evaluate for the presence or absence of estrogen or a metabolite of estrogen; and an application configured to:

determine which of the testing zones of each diagnostic test is associated with the evaluation of PdG or LH, based on the location of each result indication line, the sequence of each result indication line or the specific color of the visual label at each result indication line, capture an image or plurality of images of each diagnostic test following the application of the sample to each diagnostic test, at least one of the images capturing a diagnostic test configured to evaluate for the presence or absence of pregnanediol glucuronide in an applied fluid at a time following a separate earlier result on a diagnostic test configured to evaluate for the presence or absence of luteinizing hormone performed earlier in said menstrual cycle of the subject wherein the diagnostic test to evaluate for the presence or absence of luteinizing hormone indicated the opening of a fertile window of the subject, interpret a result or a plurality of results for each of the images by detecting the color intensity within the one or more testing zones for each of the images of diagnostic tests and correlating the detected color intensity or color intensities with a result, and display the result or the plurality of results indicated by the image of a diagnostic test or the plurality of images each of a diagnostic test on a graphical user interface.

2. The fertility tracking system of claim 1, further comprising at least one diagnostic test configured to evaluate for the presence or absence of FSH.

3. The fertility tracking system of claim 1, the application further configured to simultaneously evaluate one diagnostic test or a plurality of diagnostic tests for the presence or absence of LH and E3G.

4. The fertility tracking system of claim 1, further configured to allow the capture of an image of a diagnostic test only following an indication that the brightness in the environment of the diagnostic test is within the acceptable range.

5. The fertility tracking system of claim 1, further configured to allow the capture of an image of a diagnostic test only following an indication that the sharpness of the image is within a requisite range determined by the application.

6. The fertility tracking system of claim 1, wherein, at least one of the plurality of diagnostic tests comprises a plurality of testing zones, and wherein the application is configured to determine which of the testing zones on each diagnostic test is associated with the evaluation of PdG or LH, and the application configured to interpret a result based on the indications provided in each of the plurality of testing zones on each photographed test and display the result on the graphical user interface of a smart device.

7. The fertility tracking system of claim 1, at least one of the diagnostic tests comprising a testing zone configured to evaluate the applied sample for pregnanediol glucuronide and additionally comprising a testing zone configured to evaluate the applied sample for a metabolite of estrogen, the application further configured to determine which testing zone is configured to evaluate an applied fluid for the presence or absence with pregnanediol glucuronide and which testing zone is configured to evaluate an applied fluid for the presence or absence the metabolite of estrogen based on the location of each result indication line, the sequence of each result indication line or the specific color of the visual label at each result indication line.

8. The fertility tracking system of claim 4, each diagnostic test further comprising a testing zone configured to evaluate an applied fluid for its concentration of a metabolite of estrogen and provide a result comprising a color intensity, the color intensity correlating to a concentration of the metabolite of estrogen in the applied fluid, and the application further configured to determine which of the testing zones on each diagnostic test is associated with the evaluation of the metabolite of estrogen based on the location of each result indication line, the sequence of each result indication line or the specific color of the visual label at each result indication line.

9. The fertility tracking system of claim 1, the application configured to display a prompt on the graphical user interface, the prompt comprising a message selected from the group consisting of:

an instruction to commence testing for FSH, by utilizing a single diagnostic test from a plurality of diagnostic tests each configured to evaluate for the presence of FSH on a date selected from the range of 2-7 days following the onset of menstruation;

an instruction to commence testing for estrogen by utilizing a single diagnostic test from a plurality of diagnostic tests each configured to evaluate for the presence of estrogen following at least a 1.5-fold decrease from one diagnostic test configured to evaluate for the presence of estrogen to another diagnostic test configured to evaluate for the presence of estrogen performed on a different day in the same menstrual cycle;

an instruction to commence testing for LH by utilizing a single diagnostic test from a plurality of diagnostic tests each configured to evaluate for the presence or absence of LH at a threshold following at least an 1.5 fold increase from one diagnostic test configured to evaluate for the presence of estrogen to another diagnostic test configured to evaluate for the presence of estrogen performed on a different day in the same menstrual cycle;

an instruction to commence testing for PdG by utilizing a single diagnostic test from a plurality of diagnostic tests each configured to evaluate for the presence of PdG at a threshold following a positive result for LH on a diagnostic test obtained within the same menstrual cycle;

an indication that a follicle has been selected following a result of a 1.5-fold decrease in FSH interpreted by the application within a single menstrual cycle;

an indication of the fertile window opening and the appropriate time to engage in intercourse for conception following a result of a 1.5-fold decrease in FSH interpreted by the application within a single menstrual cycle;

an indication to commence testing for the estrogen following a result of a 1.5-fold decrease in FSH interpreted by the application within a single menstrual cycle, or on the eighth day of the menstrual cycle, whichever occurs first;

an indication that it is the appropriate time to discontinue testing for FSH and to commence testing for estrogen and an instruction to discontinue testing for FSH and to commence testing for estrogen, following a result of a 1.5-fold decrease in FSH interpreted by the application within a single menstrual cycle;

the interpretation comprising an indication of the likelihood of onset of menopause, following a result of a persistently high level of FSH interpreted by the application;

an indication of the likelihood of that ovulation may not occur this cycle or a high risk of anovulation, following a result of a persistently high level of FSH interpreted by the application;

an indication that a follicle has matured, following a result of a 1.5 fold increase in estrogen interpreted by the application, within a single menstrual cycle;

an interpretation comprising an indication of the fertile window opening, following a result of a 1.5 fold increase in estrogen within a single menstrual cycle interpreted by the application;

an indication of the follicle secreting estrogen, following a result of a 1.5 fold increase in an estrogen within a single menstrual cycle interpreted by the application;

an indication that it is the appropriate time to commence testing for LH and an instruction to commence testing for LH, following a result of a 1.5 fold increase in an estrogen within a single menstrual cycle interpreted by the application;

an indication that it is the start of the fertile window and the appropriate time to engage in intercourse for conception, following a result of a 1.5 fold increase in estrogen within a single menstrual cycle interpreted by the application;

an indication that the subject woman will not ovulate during the menstrual cycle, following a result of a persistently low level of estrogen interpreted by the application;

an indication that the subject woman is likely not fertile during the menstrual cycle, following a result of a persistently low level of estrogen interpreted by the application;

an interpretation comprising an indication that ovulation is imminent, following a result of the presence of LH at a threshold interpreted by the application;

an interpretation comprising an indication of elevated fertility or peak fertility, following a result of the presence of LH at a threshold interpreted by the application;

an interpretation comprising an indication that the subject woman should engage in sexual intercourse to conceive, following a result of the presence of LH at a threshold interpreted by the application;

an interpretation comprising an indication of the likelihood that ovulation is insufficient in this menstrual cycle for the subject woman to conceive, following a result of a persistently low level of LH interpreted by the application;

an indication that it is the appropriate time to commence testing for PdG and an instruction to commence testing for PdG, following a result of the presence of LH at a threshold interpreted by the application;

an interpretation comprising an indication that the subject woman has sufficiently ovulated, following a result of the presence of PdG at a threshold interpreted by the application on at least two tests each on separate days during the period of 7-10 days past ovulation;

an indication that ovulation has occurred, following a result of the presence of PdG at a threshold interpreted by the application;

an indication that the subject woman may engage in sexual intercourse with a low risk of conceiving until the onset of menstruation in the subsequent menstrual cycle, following a result of the presence of PdG at a threshold interpreted by the application;

an interpretation the woman has not sufficiently ovulated, following at least one result of the absence of PdG at a threshold interpreted by the application on one or more tests performed on the days selected from the range inclusive of 7-10 days past ovulation;

an interpretation comprising an indication of pregnancy, following a result of the presence of hCG at a threshold interpreted by the application;

an indication that the subject woman is not pregnant, following a result of the absence of hCG at a threshold interpreted by the application; and an indication that the subject woman has likely not produced enough progesterone to sustain pregnancy and that the subject woman should receive progesterone supplementation, following a result of the presence of hCG at a threshold and a result of the absence of PdG at a threshold interpreted by the application.

10. The fertility tracking system of claim 1, further comprising:

at least one food item comprising pumpkin seeds and flax seeds and at least one food item comprising sesame seeds and sunflower seeds, and a recurring instruction delivered via the graphical user interface application during the menstrual cycle of the subject to consume pumpkin seeds and flax seeds until the occurrence of a diagnostic test result indicating the presence of LH at a threshold on any day during the cycle, and following the occurrence of a diagnostic test result indicating the presence of LH at a threshold on any day during the cycle, a recurring instruction delivered via the graphical user interface of the application to consume sesame seeds and sunflower seeds until the onset of menstruation.

11. The fertility tracking system of claim 1, the application further configured to instruct a user on the graphical user interface to perform a diagnostic test configured to evaluate for the presence or absence of pregnanediol glucuronide at a threshold on each of the days during a range of days 7-10 following the first result on a diagnostic test indicating the presence of LH at a threshold performed earlier on the sample during the subject's same menstrual cycle, and, calculate an ovulation score based upon the number of days during the range of days 7-10 following the first result on a diagnostic test indicating the presence of LH at a threshold performed earlier on the sample during the menstrual cycle of the subject that a diagnostic test configured to evaluate for the presence or absence of pregnanediol glucuronide at a threshold indicates the presence of pregnanediol glucuronide at a threshold.

12. The fertility tracking system of claim 1, further comprising:

a progesterone supplement; and an instruction delivered via the graphical user interface to consume the progesterone supplement during the subsequent menstrual cycle following an indication of the absence of PdG at a threshold in the applied sample on any date following a positive result on a diagnostic test configured to evaluate for the presence or absence of LH in the said subsequent menstrual cycle of the subject.

13. The fertility tracking system of claim 1, further comprising a diagnostic test key displayed upon the graphical user interface and configured to provide a visual relationship of a color intensity of a result indicated on an image of a diagnostic test to a concentration of a hormone or analyte correlating to the color intensity.

14. The fertility tracking system of claim 1, configured to provide an indication that said fertile window has opened following the application's first interpretation of a diagnostic test indicating the presence of luteinizing hormone at a threshold in a menstrual cycle of the subject, and further configured to provide an indication that the fertile window has closed following the application's first interpretation of a diagnostic test indicating the presence of pregnanediol glucuronide at a threshold in the sample of a subject.

15. The fertility tracking system of claim 1, wherein the applied sample comprises urine of the subject.

16. The fertility tracking system of claim 1, wherein the visual label comprises colloidal gold.

17. The fertility tracking system of claim 1, wherein the visual label comprises latex beads.

* * * * *